US009896429B2

(12) United States Patent
Dull et al.

(10) Patent No.: US 9,896,429 B2
(45) Date of Patent: Feb. 20, 2018

(54) NICOTINE SALTS, CO-CRYSTALS, AND SALT CO-CRYSTAL COMPLEXES

(71) Applicant: R.J. Reynolds Tobacco Company, Winston-Salem, NC (US)

(72) Inventors: Gary M. Dull, Lewisville, NC (US); Andrew Carr, Cambridge (GB); Emma Sharp, Cambridgeshire (GB)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 0 days.

(21) Appl. No.: 14/951,939

(22) Filed: Nov. 25, 2015

(65) Prior Publication Data

US 2016/0185750 A1   Jun. 30, 2016

Related U.S. Application Data

(63) Continuation-in-part of application No. 14/721,283, filed on May 26, 2015, now Pat. No. 9,738,622.

(60) Provisional application No. 62/003,295, filed on May 27, 2014.

(51) Int. Cl.
*C07D 401/04* (2006.01)
*C07D 239/52* (2006.01)
*A24F 47/00* (2006.01)
*A24B 13/00* (2006.01)
*A24B 15/24* (2006.01)
*C07C 57/15* (2006.01)
*A61M 15/06* (2006.01)
*A61M 11/04* (2006.01)
*A61K 9/00* (2006.01)

(52) U.S. Cl.
CPC ............ *C07D 401/04* (2013.01); *A24B 13/00* (2013.01); *A24B 15/243* (2013.01); *A24F 47/008* (2013.01); *C07C 57/15* (2013.01); *C07D 239/52* (2013.01); *A61K 9/0056* (2013.01); *A61K 9/0073* (2013.01); *A61M 11/042* (2014.02); *A61M 15/06* (2013.01); *A61M 2205/8206* (2013.01)

(58) Field of Classification Search
CPC .................................................. C07D 401/04
USPC ........................................ 546/279.4; 514/343
See application file for complete search history.

(56) References Cited

U.S. PATENT DOCUMENTS

| | | | |
|---|---|---|---|
| 2,033,909 A | 3/1936 | Cox et al. | |
| 2,822,306 A | 2/1958 | Thienemann et al. | |
| 4,153,063 A | 5/1979 | Roselius et al. | |
| 4,830,028 A | 5/1989 | Lawson et al. | |
| 4,967,771 A | 11/1990 | Fagg et al. | |
| 5,031,646 A | 7/1991 | Lippiello et al. | |
| 7,008,742 B2 | 3/2006 | Molaire | |
| 7,452,555 B2 | 11/2008 | Childs | |
| 7,650,891 B1 | 1/2010 | Groves et al. | |
| 7,927,613 B2 | 4/2011 | Almarsson et al. | |
| 7,935,817 B2 | 5/2011 | Blazecka et al. | |
| 8,058,437 B2 | 11/2011 | Bauer | |
| 8,163,790 B2 | 4/2012 | Childs | |
| 8,173,625 B2 | 5/2012 | Brittain et al. | |
| 8,197,592 B2 | 6/2012 | Thompson et al. | |
| 8,212,079 B2 | 7/2012 | Childs | |
| 8,241,371 B2 | 8/2012 | Hanna et al. | |
| 8,350,085 B2 | 1/2013 | Childs | |
| 8,415,507 B2 | 4/2013 | Schultheiss et al. | |
| 8,466,280 B2 | 6/2013 | Grunenberg et al. | |
| 8,470,832 B2 | 6/2013 | George et al. | |
| 8,513,236 B2 | 8/2013 | Schultheiss et al. | |
| 8,999,405 B1 | 4/2015 | Bachman | |
| 2002/0048610 A1 | 4/2002 | Cima et al. | |
| 2003/0224006 A1 | 12/2003 | Zaworotko et al. | |
| 2006/0018840 A1 | 1/2006 | Lechuga-Ballesteros et al. | |
| 2007/0287194 A1 | 12/2007 | Childs et al. | |
| 2008/0280858 A1 | 11/2008 | Hanna et al. | |
| 2008/0302377 A1 | 12/2008 | Nauryzbaev et al. | |
| 2010/0204204 A1 | 8/2010 | Zaworotko et al. | |
| 2011/0152266 A1 | 6/2011 | Grunenberg et al. | |
| 2011/0174323 A1 | 7/2011 | Coleman, III et al. | |
| 2011/0236478 A1 | 9/2011 | Dokou et al. | |
| 2011/0251426 A1 | 10/2011 | Childs et al. | |
| 2011/0257430 A1 | 10/2011 | Childs | |
| 2011/0259353 A1 | 10/2011 | Coleman, III et al. | |
| 2011/0268809 A1 | 11/2011 | Brinkley et al. | |
| 2012/0022117 A1 | 1/2012 | Gruss et al. | |
| 2012/0028930 A1 | 2/2012 | Kalofonos et al. | |
| 2012/0028998 A1 | 2/2012 | Sansone et al. | |
| 2012/0192880 A1 | 8/2012 | Dube et al. | |

(Continued)

FOREIGN PATENT DOCUMENTS

WO    WO 03/101454    12/2003
WO    WO 2014/182736    11/2014

OTHER PUBLICATIONS

Stahly, "Diversity in Single-, etc.", Crystal Growth & Design, 7 (6), 2007, 1007-1026.*

(Continued)

*Primary Examiner* — Patricia L Morris
(74) *Attorney, Agent, or Firm* — Womble Bond Dickinson (US) LLP

(57) ABSTRACT

The invention provides certain nicotine salts, co-crystals, and salt co-crystals and provides novel polymorphic forms of certain nicotine salts. In particular, nicotine salts with orotic acid are described. The invention further provides methods of preparation and characterization of such nicotine salts. In addition, tobacco products, including smoking articles, smokeless tobacco products, and electronic smoking articles comprising nicotine salts, co-crystals, and/or salt co-crystals are also provided.

7 Claims, 42 Drawing Sheets

(56) References Cited

U.S. PATENT DOCUMENTS

| | | |
|---|---|---|
| 2012/0192882 A1 | 8/2012 | Dube et al. |
| 2012/0211016 A1 | 8/2012 | Byrd, Jr. et al. |
| 2012/0258170 A1 | 10/2012 | Kruthiventi et al. |
| 2013/0040970 A1 | 2/2013 | Cosgrove et al. |
| 2013/0072440 A1 | 3/2013 | Dokou et al. |
| 2013/0203806 A1 | 8/2013 | Chorlton et al. |
| 2013/0274296 A1 | 10/2013 | Jackson et al. |
| 2014/0088044 A1 | 3/2014 | Rigas et al. |
| 2017/0035108 A1 | 2/2017 | Zinovik et al. |

OTHER PUBLICATIONS

Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Seddon "Pseudopolymorph . . . " Crystal Growth & design v.4(6) p. 1087 (2004) (2 pages from internet).*
Ivanisevic et al., "Use of X-ray . . . " Pharm. Sci. Encycl. p. 1-42 (2010).*
Ivanisevic et al., "Uses of X-ray, etc.," Pharm. Form. Qual. 2011, pp. 30-33.*
Bhattacharya et al., "Thermoanalytical and Crystallographic Methods" in Brittain H. ed., 2nd ed. Informa Healthcare:NY 2009 p. 318-335.*
Aakeroy, "Crystal Engineering, etc.," Acta Cryst. (1997) B53, 569-586.*
Sekhon BS, "Pharmaceutical co-cyrstals, etc." Ars Pharm., 50(2): 99-117 (2009).*
Kirk-Othmer Encyclopedia of Chemical Technology, 8, pp. 95-147 (2002).*
Halebian et al., Pharmaceutical Applications, etc., Pharmaceutical Sciences 58(8), 1969, 911-929.*
www.jce.divched.org "Nicotine Volatilization in Tobacco Matrix," *Journal of Chemical Education*, 2005, vol. 82, No. 10, pp. 1577-1578.
http://www.fda.gov/Drugs/GuidanceComplianceRegulatoryInformation/Guidance/default.htm; "Guidance for Industry, Regulatory Classification of Pharmaceutical Co-Crystals," U.S. Department of Health and Human Services, Food and Drug Administration, Center for Drug Evaluation and Research, (CDER), Apr. 2013, pp. 1-5.
Challener, "API Synthesis & Manufacturing: Scientific Advances in Cocrystals are Offset by Regulatory Uncertainty," *Pharmaceutical Technology*, May 2014, pp. 42-45. www.PharmTech.com.
Dezelic et al. "Nicotine Compounds with Aromatic Acids," *Kem. Vjestnik*, 17, 1943, 39-57.
Dezelic et al., "Nicotine Compounds with Aromatic Acids. Part II," *Glasnik Drustva Hemicara Technol. NR Bosne Hercegovine*, 1961, vol. 10, pp. 55-62.
Dezelic et al., "Determination of the Composition and the Molecualar Weights of Some Salts of Heterocyclic Bases from the UV Spectra" *Glasnik Hemicara i Tehnologa BiH, Sarajevo*, 1964-1965, 13-14, 27-36.
Dezelic et al., "Determination of Structure of Some Salts of Nicotine, pyridine and N-Methylpyrrolidine on the Basis of Their Infra-Red Spectra," *Spectrochimica Acta, Part A: Molecular and Biomolecular Spectroscopy* (1967), 23(A), 1149-53.
Kim et al., "The Crystal Structure of a 1:1 Nicotine-Salicylic Acid Complex (Nicotinyl Salicylate)," *Acta Cryst.*, 1971, B27, pp. 1123-1131.
Lasslo et al., "Salts of p-Acetamidobenzoic Acid," *J. Amer. Pharm. Assoc.* (1912-1977), 1959, 48, 345-7.
Nikolin et al., "Structure of Some Nicotine Salts and Their Fungicidal Action," *Glasnik Hemicara i Tehnologa BiH, Sarajevo*, 18, (1970) pp. 17-24.
Perfetti, "Structural Study of Nicotine Salts," *Beitrage Tabakforschung Int.*, vol. 12, No. 2, 43-54 (1983).
Perfetti, "The Transfer of Nicotine from Nicotine Salts to Mainstream Smoke," *Beitrage Tabakforschung Int.,Contributions to Tobacco Research*, vol. 19, No. 3, 2000, pp. 141-158.
Seeman et al., "The Form of Nicotine in Tobacco. Thermal Transfer of Nicotine and Nicotine Acid Salts to Nicotine in the Gas Phase," *J. Agric. Food Chem.* 1999, vol. 47, pp. 5133-5145.

* cited by examiner

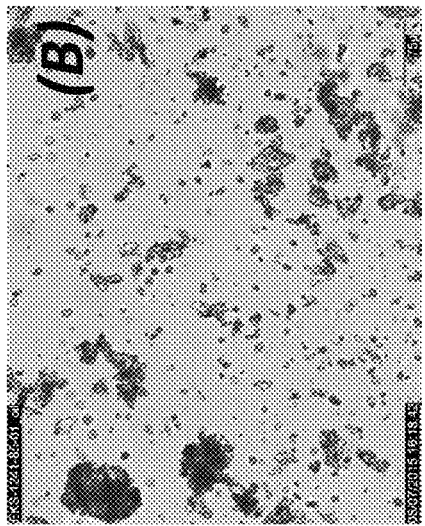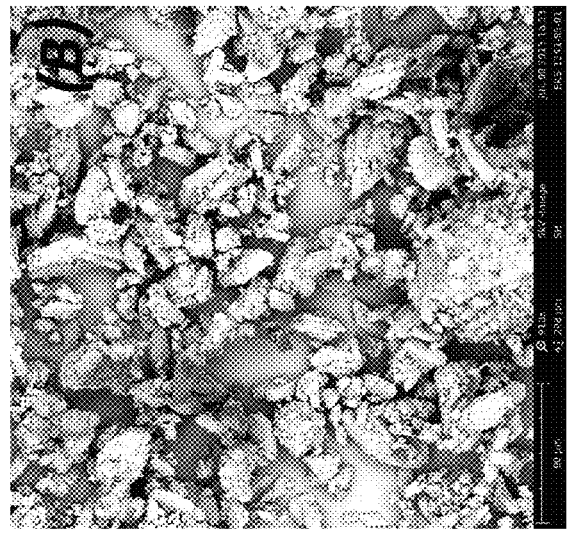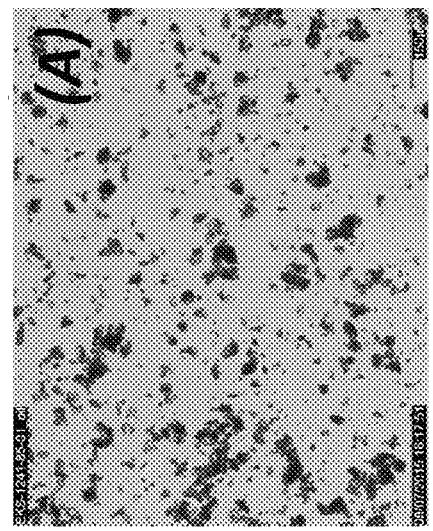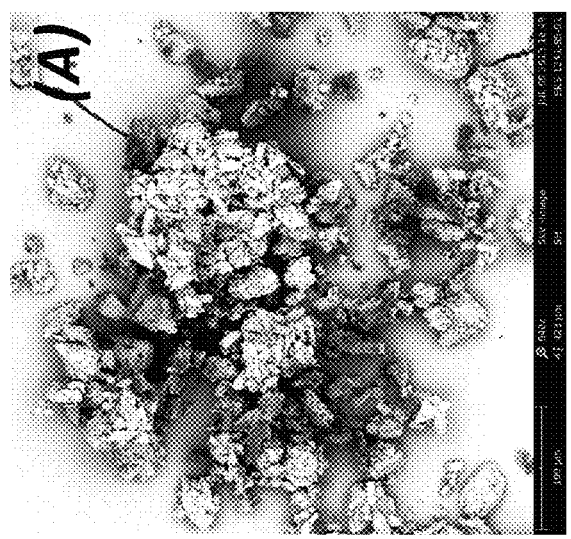
FIG. 19
FIG. 20

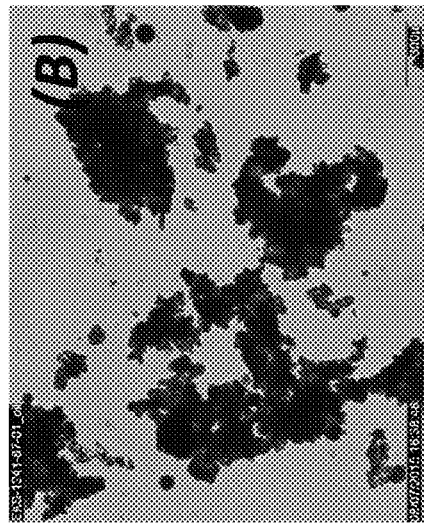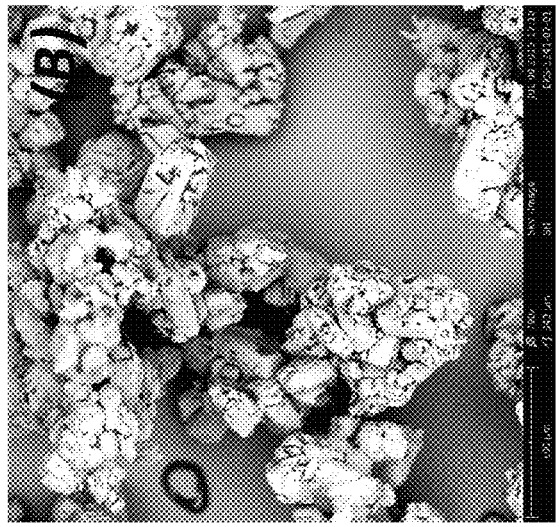
FIG. 40  FIG. 41
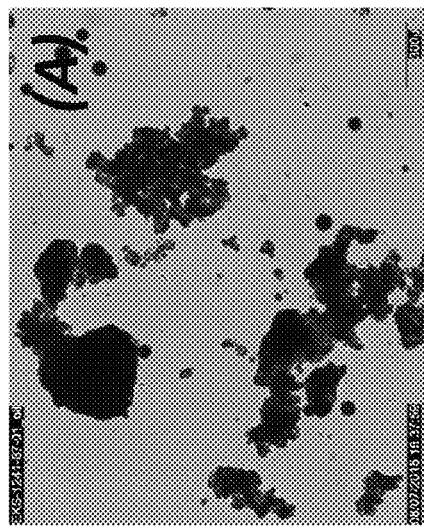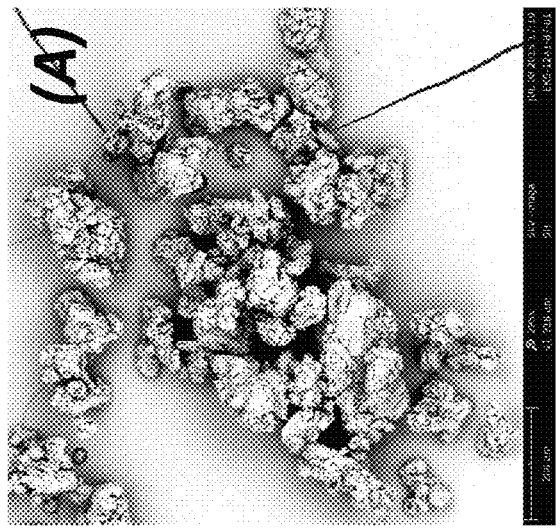

NICOTINE SALTS, CO-CRYSTALS, AND SALT CO-CRYSTAL COMPLEXES

CROSS-REFERENCE TO RELATED APPLICATIONS

The present application is a continuation-in-part of U.S. patent application Ser. No. 14/721,283, filed May 26, 2015, which claims priority to U.S. Provisional Patent Application No. 62/003,295, filed May 27, 2014, which are incorporated by reference herein.

FIELD OF THE INVENTION

The present invention relates to various salts, co-crystals, and salt co-crystals of nicotine and to compositions and products (e.g., tobacco products) into which such salts, co-crystals, and salt co-crystals can be incorporated.

BACKGROUND OF THE INVENTION

Cigarettes, cigars and pipes are popular smoking articles that employ tobacco in various forms. Such smoking articles are used by heating or burning tobacco, and aerosol (e.g., smoke) is inhaled by the smoker. Electronic smoking articles are a further type of tobacco product, which comprise a reservoir and heating system for the delivery of aerosolizable materials. Tobacco also may be enjoyed in a so-called "smokeless" form. Particularly popular smokeless tobacco products are employed by inserting some form of processed tobacco or tobacco-containing formulation into the mouth of the user.

Various types of cigarette components, including tobacco types, tobacco blends, top dressing and casing materials, blend packing densities and types of paper wrapping materials for tobacco rods, are set forth in the art. See, for example, the various representative types of cigarette components, as well as the various cigarette designs, formats, configurations and characteristics, that are set forth in Johnson, Development of Cigarette Components to Meet Industry Needs, 52$^{nd}$ T.S.R.C. (September 1998); U.S. Pat. No. 5,101,839 to Jakob et al.; U.S. Pat. No. 5,159,944 to Arzonico et al.; U.S. Pat. No. 5,220,930 to Gentry and U.S. Pat. No. 6,779,530 to Kraker; US Pat. App. Pub. Nos. 2005/0016556 to Ashcraft et al.; 2005/0066986 to Nestor et al.; 2005/0076929 to Fitzgerald et al.; 2006/0272655 to Thomas et al.; 2007/0056600 to Coleman, III et al.; and 2007/0246055 to Oglesby, each of which is incorporated herein by reference.

Exemplary smokeless tobacco formulations, ingredients, and processing methodologies are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0196730 to Engstrom et al.; 2008/0209586 to Neilsen et al.; 2008/0305216 to Crawford et al.; 2009/0065013 to Essen et al.; 2009/0293889 to Kumar et al.; 2010/0291245 to Gao et al. and 2011/0139164 to Mua et al.; PCT WO 04/095959 to Amarp et al. and WO 2010/132444 A2 to Atchley; each of which is incorporated herein by reference. Exemplary smokeless tobacco products that have been marketed include those referred to as CAMEL Snus, CAMEL Orbs, CAMEL Strips and CAMEL Sticks by R. J. Reynolds Tobacco Company; GRIZZLY moist tobacco, KODIAK moist tobacco, LEVI GARRETT loose tobacco and TAYLOR'S PRIDE loose tobacco by American Snuff Company, LLC; KAYAK moist snuff and CHATTANOOGA CHEW chewing tobacco by Swisher International, Inc.; REDMAN chewing tobacco by Pinkerton Tobacco Co. LP; COPENHAGEN moist tobacco, COPENHAGEN Pouches, SKOAL Bandits, SKOAL Pouches, RED SEAL long cut and REVEL Mint Tobacco Packs by U.S. Smokeless Tobacco Company; and MARLBORO Snus and Taboka by Philip Morris USA.

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. Pub. No. 2013/0255702 to Griffith Jr. et al., U.S. Pat. Pub. Nos. 2014/0000638 to Sebastian et al., 2014/0060554 to Collett et al., 2014/0060555 to Chang et al., 2014/0096781 to Sears et al., 2014/0096782 to Ampolini et al., and 2015/0059780 to Davis et al., which are incorporated herein by reference in their entireties.

Certain of these types of smoking articles, smokeless tobacco products, and electronic smoking articles comprise a tobacco extract, which in some products may be purified such that the extract is comprised primarily of nicotine. However, tobacco extracts comprising a high percentage of nicotine (including extracts comprising at least about 90%, at least about 95%, and at least about 99% nicotine by weight) are typically in oil form. As such, nicotine extracts can be difficult to handle and incorporate into certain tobacco products.

It would be desirable to provide such nicotine-based extracts in a form that is amenable to incorporation in tobacco products. It would further be desirable to incorporate such extracts into an enjoyable form of a tobacco product and to provide processes for preparing such forms of nicotine-based extracts as well as for preparing various types of compositions and products incorporating such forms of nicotine-based extracts.

SUMMARY OF THE INVENTION

The present invention provides various forms of nicotine that can be applicable to a wide range of products, including tobacco products. Particularly, the present application describes nicotine salts, co-crystals, and salt co-crystals and the preparation of such nicotine salts, co-crystals, and salt co-crystals. It also describes the incorporation of such nicotine salts, co-crystals, and/or salt co-crystals into various products including tobacco products (e.g., smoking articles, smokeless tobacco products, and electronic smoking articles) and pharmaceutical products.

In a first aspect of the invention is provided a salt of nicotine and orotic acid. In some embodiments, the salt is a bis-orotic acid salt-co-crystal. The bis-orotic acid salt-co-crystal can, in certain embodiments, be in hemi-hydrate form. In some embodiments, the salt is a mono-orotic acid salt.

Advantageously, in some embodiments, a given percentage of the salt or salt-co-crystal is in crystalline form. For example, in various embodiments at least about 50% of the salt or salt-co-crystal is in crystalline form. In other embodiments, at least about 80 or at least about 90% of the salt or salt-co-crystal is in crystalline form.

The orotate salts or salt-co-crystals can, in some embodiments, be characterized as having particular peaks in X-ray powder diffraction patterns obtained therefrom. For example, one salt can be characterized by an X-ray powder diffraction pattern having peaks at one or more of the following 2-theta diffraction angles: 8.8, 13.4, 17.7, 26.5, and 29.3. As another example, one salt can be characterized by an X-ray powder diffraction pattern having peaks at one or more of the following 2-theta diffraction angles: 9.1, 14.7, 15.4, 17.3, 25.0, 25.4, and 27.0.

The invention also provides nicotine fumarate salts and certain forms thereof, and products incorporating such salts.

The nicotine salts, co-crystals, and salt co-crystals described in the present application are generally applicable for use in a range of products including, but not limited to, smoking articles, electronic smoking articles, smokeless tobacco products (e.g., lozenges and gums), pharmaceutical products, and the like. Accordingly, in another aspect of the invention is provided a product incorporating one or more nicotine salts, co-crystals, and/or salt co-crystals as described herein. In various embodiments, electronic smoking articles, smokeless tobacco products, and/or pharmaceutical products incorporating one or more of the salts, co-crystals, and/or salt co-crystal complexes disclosed herein are provided.

For example, in one aspect, the disclosure provides an electronic smoking article comprising an inhalable substance medium contained within a cartridge body and a heating member positioned to provide heat to at least a portion of the inhalable substance medium, wherein the inhalable substance medium comprises nicotine fumarate or a salt or salt-co-crystal of nicotine and orotic acid. The inhalable substance medium can further comprise, for example, one or more of glycerin, water, and a flavorant. The amount of nicotine fumarate or salt or salt-co-crystal of nicotine and orotic acid incorporated can vary and, in some embodiments, can be that amount sufficient to provide nicotine in an amount of about 0.01 mg to about 0.5 mg, about 0.05 mg to about 0.3 mg, or about 0.1 mg to about 0.2 mg per puff on the article.

In another aspect, the disclosure provides a smokeless tobacco product comprising nicotine fumarate or a salt or salt-co-crystal of nicotine and orotic acid. Exemplary smokeless tobacco products include, but are not limited to, loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; and capsule-like materials possessing an outer shell and an inner region.

In a further aspect, the disclosure provides a pharmaceutical product comprising a nicotine salt or crystalline polymorphic form as described herein (e.g., nicotine fumarate or a salt or salt-co-crystal of nicotine and orotic acid). Such products can be, for example, in a form selected from the group consisting of a pill, tablet, lozenge, capsule, caplet, pouch, gum, inhaler, solution, and cream. One exemplary lozenge formulation comprises one or more of the nicotine salts or crystalline polymorphic forms disclosed herein and at least about 50% by weight isomalt.

Additionally, in a still further aspect, the disclosure provides methods of preparing certain nicotine salts, salt-co-crystals, and crystalline polymorphic forms. For example, the disclosure provides methods of preparing nicotine orotate salts or salt-co-crystals. In one embodiment, the disclosure provides a method of preparing a salt or salt-co-crystal of nicotine and orotic acid, comprising combining nicotine and orotic acid to form a solid and isolating the solid. In certain embodiments, the combining comprises grinding the nicotine and orotic acid or comprises mixing the nicotine and orotic acid in neat nicotine or in a solvent selected from the group consisting of water, MEK, IPA, ethyl acetate and mixtures thereof, and wherein the solid is a mono-orotate salt (which can be in hemihydrate form). In certain embodiments, the combining comprises mixing the nicotine and orotic acid in THF, ethanol, or a mixture thereof, and wherein the solid is a bis-orotate salt-co-crystal (which can be non-solvated).

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

FIGS. 19(A) and 19(B) are microscopy images for a scaled up material prepared from nicotine and orotic acid in THF (exhibiting XRPD Orotate Pattern 1);

FIGS. 20(A) and 20(B) are scanning electron microscopy (SEM) images for scaled up material prepared from nicotine and orotic acid in THF (exhibiting XRPD Orotate Pattern 1);

FIGS. 40(A) and 40(B) are microscopy images of a scaled up material prepared from nicotine and fumaric acid in THF;

FIGS. 41(A) and 41(B) are SEM images for a scaled up material prepared from nicotine and fumaric acid in THF;

DETAILED DESCRIPTION OF THE PREFERRED EMBODIMENTS

Figure 1:
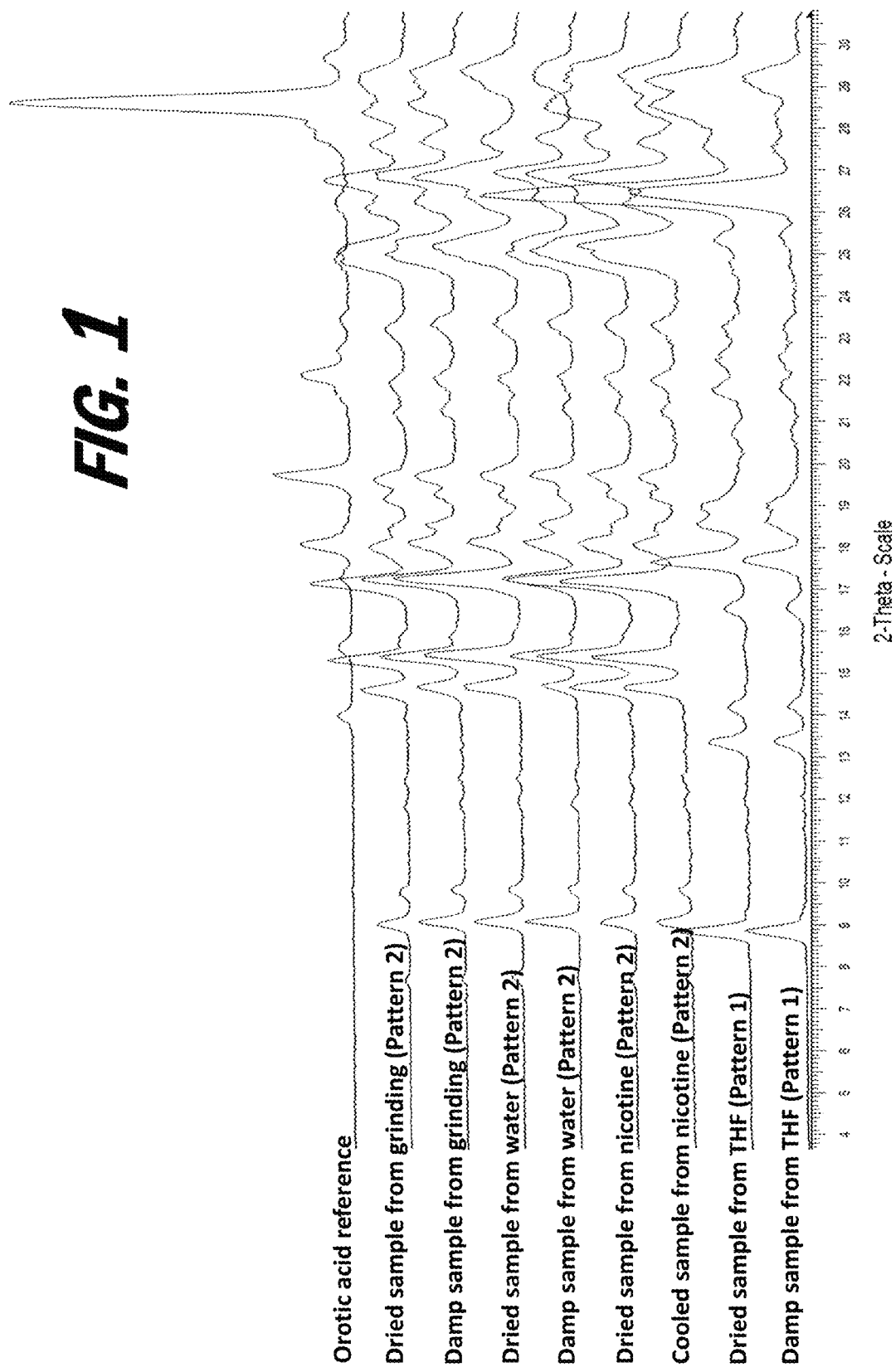
FIG. 1 provides XRPD diffractograms of solid materials prepared from nicotine and orotic acid by various methods.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present invention relates to nicotine salts, co-crystals, and salt co-crystals and methods of preparation thereof. It also relates to products (including tobacco products and pharmaceutical products) that comprise one or more nicotine salts, co-crystals, and/or salt co-crystals. In certain embodiments, nicotine provided in one or more such forms can advantageously be isolated in a physical form that is an improvement over neat nicotine, which is a hygroscopic, oily liquid. For example, in certain embodiments, nicotine salts, co-crystals, and/or salt co-crystals as described herein can be in an easier to handle form than neat nicotine (e.g., a solid or semi-solid form), can be provided in a higher purity form than neat nicotine, and/or can exhibit greater thermodynamic, physical, and/or chemical stability (e.g., a higher resistance to oxidation, reduced risk of hydrate formation, and/or a longer shelf life) than neat nicotine. In some embodiments, nicotine salts, co-crystals, and/or salt co-crystals can provide increased stability in the presence of relevant excipients in the product into which the salt, co-crystal, and/or salt co-crystal will be incorporated, as compared to neat nicotine. In some embodiments, nicotine salts, co-crystals, and salt co-crystals can exhibit a significant degree of water-solubility, rendering them applicable for incorporation within a wide range of compositions and products.

Nicotine itself can be isolated and/or treated such that it is in one of two enantiomeric forms or it may be provided in racemic form. Nicotine is naturally occurring in levorotatory, (L)-nicotine form (also known as (−)-nicotine or S-nicotine). In the salts, co-crystals, and salt co-crystals provided herein, the nicotine is generally in the form of (L)-nicotine, although this disclosure is not intended to preclude the preparation and application of dextrorotatory ((D)-nicotine) salts, co-crystals, and salt co-crystals or racemic forms of nicotine in the disclosed salts, co-crystals, and salt co-crystals. Accordingly, nicotine salts, co-crystals, and salt co-crystals can be in an enantiomerically highly pure form (i.e., (L)- or (D)-form) or in racemic form as described herein.

A "nicotine salt" is a form of nicotine characterized by the interaction between nicotine in ionic form and a coformer in ionic form (e.g., an acid) via the transfer of one or more protons from the coformer donor to the nicotine acceptor. The structure of nicotine is such that it comprises two nitrogen atoms that are capable of accepting protons from a coformer and, accordingly, it can be present in non-protonated, mono-protonated, and/or di-protonated form in a given sample.

Certain nicotine salts are presently known. For example, nicotine sulfate has been sold as a pesticide and nicotine bitartrate dihydrate (also known as nicotine hydrogen tartrate) is a commercially available, water-soluble nicotine salt. Various other salts have been studied, including a nicotine acetic acid salt (which forms a viscous oil) as well as, for example, nicotine citrates and nicotine malates. See, for example, the types of ingredients and techniques set forth in U.S. Pat. No. 2,033,909 to Cox et al. and Perfetti, *Beitrage Tabakforschung Int.*, 12, 43-54 (1983). Additionally, certain salts of nicotine have been available from sources such as Pfaltz and Bauer, Inc. and K&K Laboratories, Division of ICN Biochemicals, Inc. Exemplary known nicotine salts include nicotine salts such as nicotine tartrate and nicotine bitartrate, nicotine chloride (e.g., nicotine hydrochloride and nicotine dihydrochloride), nicotine sulfate, nicotine perchlorate, nicotine ascorbate, nicotine fumarate, nicotine citrate, nicotine malate, nicotine lactate, nicotine aspartate, nicotine salicylate, nicotine tosylate, nicotine succinate, nicotine pyruvate, and nicotine salt hydrates (e.g., nicotine zinc chloride monohydrate). A nicotine salt with levulinic acid is discussed in US Pat. App. Pub. No. 2011/0268809 and Int. App. Pub. No. PCT/US2011/033928, both to Brinkley et al., which are incorporated herein by reference. See also, for example, U.S. Pat. No. 4,830,028 to Lawson et al. and U.S. Pat. No. 5,031,646 to Lippiello et al. and Leonard, Ind. Eng. Chem. 48: 1331-1341 (1956). However, certain previously disclosed nicotine salts of organic acids are not commonly crystalline and can exhibit a range of stoichiometries, which may make them unsuitable for use in certain applications.

A "nicotine co-crystal" is a form of nicotine comprising nicotine and at least one other component ("coformer"), both in neutral form. Co-crystals are typically characterized by a crystalline structure, which is generally held together by freely reversible, non-covalent interactions. Co-crystals are typically made up of nicotine and at least one other component in a defined stoichiometric ratio. In some embodiments, co-crystals can encompass hydrates, solvates, and clathrates. Co-crystals can comprise nicotine in combination with an organic and/or an inorganic component. Co-crystals can generally be distinguished from salts by the absence of a proton transfer between the components (i.e., the nicotine and the one or more coformers) in a co-crystal. According to the U.S. Food and Drug Administration's Guidance for Industry (April 2013), a co-crystal is defined as a solid that is a crystalline material composed of two or more molecules in the same crystal lattice, where the components are in a neutral state and interact via nonionic interactions. See U.S. Department of Health and Human Services, Food and Drug Administration, Guidance for Industry: Regulatory Classification of Pharmaceutical Co-Crystals (April 2013), which is incorporated herein by reference.

A "nicotine salt co-crystal" is a type of hybrid structure with both salt and co-crystal characteristics. Typically, a nicotine molecule within a salt co-crystal is associated with at least two coformers (which may be the same or different), wherein one coformer is in ionic form (e.g., an acid) and transfers a proton to the nicotine molecule and wherein a second coformer does not transfer a proton to the nicotine molecule.

The stoichiometry of the salts, co-crystals, and salt co-crystals described herein can vary. For example, in certain embodiments, where two components (i.e., nicotine and one coformer) are present, the nicotine:coformer stoichiometry can range in certain embodiments from about 5:1 to about 1:5 nicotine:coformer. Where more than one coformer is used to form a nicotine salt, co-crystal, or salt co-crystal, the ratios of the coformers with respect to both the nicotine and to one another can also vary. In preferable embodiments, a given sample of the salts, co-crystals, and salt co-crystals provided according to the present disclosure exhibit substantially one single stoichiometry.

The salts, co-crystals, and salt co-crystals described herein can, in some embodiments, exist in various polymorphic and pseudopolymorphic forms. Polymorphism is the ability of a crystalline material to exist in more than one form or crystal structure. Polymorphism can result, e.g., from the existence of different crystal packing structures (packing polymorphism) or from the existence of different conformers of the same molecule (conformational polymorphism). Pseudopolymorphism is the result of hydration or solvation of a material and is also referred to as solvomorphism.

The salts, co-crystals, and salt co-crystals of the present disclosure can incorporate nicotine derived from some form of a plant of the *Nicotiana* species (e.g., some form of tobacco). The nicotine can be, for example, in the form of a highly purified tobacco extract. Various methods are known for the isolation and purification of nicotine from tobacco (including, but not limited to, extraction from tobacco with water; extraction from tobacco with organic solvents; steam distillation from tobacco; or pyrolytic degradation of tobacco and distillation of nicotine therefrom). For exemplary extraction methods, see for example, U.S. Pat. Nos. 2,822,306 and 4,153,063 to Roselius et al. and US Pat. App.

Pub. No. 2008/0302377 to Kauryzbaev et al., which are incorporated herein by reference.

The selection of the plant from the *Nicotiana* species (from which such extracts and other tobacco materials that can be combined with the salts, co-crystals, and/or salt co-crystals described herein are obtained) can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. *Nicotiana* species can be derived using genetic-modification or crossbreeding techniques (e.g., tobacco plants can be genetically engineered or crossbred to increase or decrease production of or to other change certain components, characteristics or attributes). Additional information on types of *Nicotiana* species suitable for use in the present invention can be found in US Pat. App. Pub. No. 2012/0192880 to Dube et al., which is incorporated by reference herein. Tobacco plants can be grown in greenhouses, growth chambers, or outdoors in fields, or grown hydroponically.

The portion or portions of the plant of the *Nicotiana* species used according to the present invention can vary. For example, virtually all of the plant (e.g., the whole plant) can be harvested, and employed as such. Alternatively, various parts or pieces of the plant can be harvested or separated for further use after harvest. For example, the leaves, stem, stalk, roots, lamina, flowers, seed, and various portions and combinations thereof, can be isolated for further use or treatment. The plant material of the invention may thus comprise an entire plant or any portion of a plant of the *Nicotiana* species. See, for example, the portions of tobacco plants set forth in US Pat. App. Pub. Nos. 2011/0174323 to Coleman, III et al. and 2012/0192880 to Dube et al., which are incorporated by reference herein.

The plant of the *Nicotiana* species can be employed in either an immature or mature form, and can be used in either a green form or a cured form, as described in 2012/0192880 to Dube et al., which is incorporated by reference herein. The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. Exemplary processing techniques are described, for example, in US Pat. App. Pub. Nos. 2009/0025739 to Brinkley et al. and 2011/0174323 to Coleman. III et al., which are incorporated by reference herein. At least a portion of the plant of the *Nicotiana* species can be treated with enzymes and/or probiotics before or after harvest, as discussed in US Pat. App. Pub. Nos. 2013/0269719 to Marshall et al. and 2014/0020694 to Moldoveanu, which are incorporated herein by reference.

A harvested portion or portions of the plant of the *Nicotiana* species can be physically processed. A portion or portions of the plant can be separated into individual parts or pieces (e.g., roots can be removed from stalks, stems can be removed from stalks, leaves can be removed from stalks and/or stems, petals can be removed from the remaining portion of the flower). The harvested portion or portions of the plant can be further subdivided into parts or pieces (e.g., shredded, cut, comminuted, pulverized, milled or ground into pieces or parts that can be characterized as filler-type pieces, granules, particulates or fine powders). The harvested portion or portions of the plant can be subjected to external forces or pressure (e.g., by being pressed or subjected to roll treatment). When carrying out such processing conditions, the harvested portion or portions of the plant can have a moisture content that approximates its natural moisture content (e.g., its moisture content immediately upon harvest), a moisture content achieved by adding moisture to the harvested portion or portions of the plant, or a moisture content that results from the drying of the harvested portion or portions of the plant. As such, harvested portion or portions of the plant can be used as such as components of tobacco products, or processed further.

To provide a nicotine extract, the plant of the *Nicotiana* species or portions thereof is typically subjected to one or more types of processing conditions. Typical separation processes can include one or more process steps (e.g., solvent extraction using polar solvents, organic solvents, and/or supercritical fluids), chromatography, distillation, filtration, recrystallization, and/or solvent-solvent partitioning. Exemplary extraction and separation solvents or carriers include water, alcohols (e.g., methanol or ethanol), hydrocarbons (e.g., heptane and hexane), halogenated hydrocarbons (e.g., monofluorotrichloromethane (Freon 11), dichlorotrifluoroethane (Freon 123), and the like), diethyl ether, methylene chloride, and supercritical carbon dioxide. See, for example, the description of isolated tobacco components and techniques for isolation in U.S. Pat. No. 4,967,771 to Fagg et al., US Pat. App. Pub. Nos. 2011/0174323 to Coleman, III et al.; 2011/0259353 to Coleman, III et al.; 2012/0192880 to Dube et al.; 2012/0192882 to Dube et al.; and 2012/0211016 to Byrd, Jr. et al., which are incorporated by reference herein.

Although the nicotine incorporated within the salts, co-crystals, and salt co-crystals of the present disclosure are commonly derived from some form of a plant of the *Nicotiana* species as outlined above, the source of the nicotine is not limited thereto. For example, in some embodiments, nicotine may be provided synthetically. In some embodiments, nicotine may be obtained from another source (e.g., another type of plant).

Nicotine is typically isolated (e.g., as described above) in neat (liquid) form. According to the present invention, nicotine is modified such that it is provided in other forms by incorporating the nicotine as a component of a salt, co-crystal, or salt co-crystal, e.g., in the form of an oil, solid, semi-solid, etc. In some embodiments, certain salts, co-crystals, and salt co-crystals are desirably provided in solid form, e.g., solid, crystalline form. Advantageously (although not necessarily), coformers (including acids) that are combined with nicotine to form such nicotine salts, co-crystals, or salt co-crystals are "GRAS" (Generally Regarded As Safe) according to the U.S. Food and Drug Administration. Furthermore, it is beneficial (although again, not necessary) for the nicotine salts, co-crystals, and/or salt co-crystals produced thereby to also be GRAS.

In one embodiment, a salt or salt-co-crystal of nicotine and orotic acid is provided. The stoichiometry of the orotate salts and salt-co-crystals provided herein can vary. For example, in certain embodiments, a nicotine orotate salt or salt-co-crystal is provided having a stoichiometry of between about 1:2 nicotine:acid and about 1:1 nicotine:acid (i.e., having at least about 1 equivalent of acid per nicotine).

In certain embodiments, the nicotine orotate salt or salt-co-crystals disclosed herein are provided in solid form and may be in crystalline and/or amorphous form. In one form, the nicotine orotate (believed to be a bis-orotate salt-co-crystal) can be described as exhibiting an XRPD pattern (referred to herein as "Orotate Pattern 1") with peaks at one or more of the following 2-theta angles: 8.8, 13.4, 17.7, 26.5, and 29.3. Although not intending to be limited by theory, the relative pKa values of nicotine and orotic acid suggest that only one of the orotic acid molecules is likely to be deprotonated, marking this material as a salt/co-crystal hybrid. Full characterization data, including a table of all relevant peaks in the x-ray diffraction pattern is provided in Example 1. See also FIGS. 14-21, providing the results of various methods of characterization of a scaled up sample of this (Orotate Pattern 1/bis-orotate salt-co-crystal) material.

Figure 29:
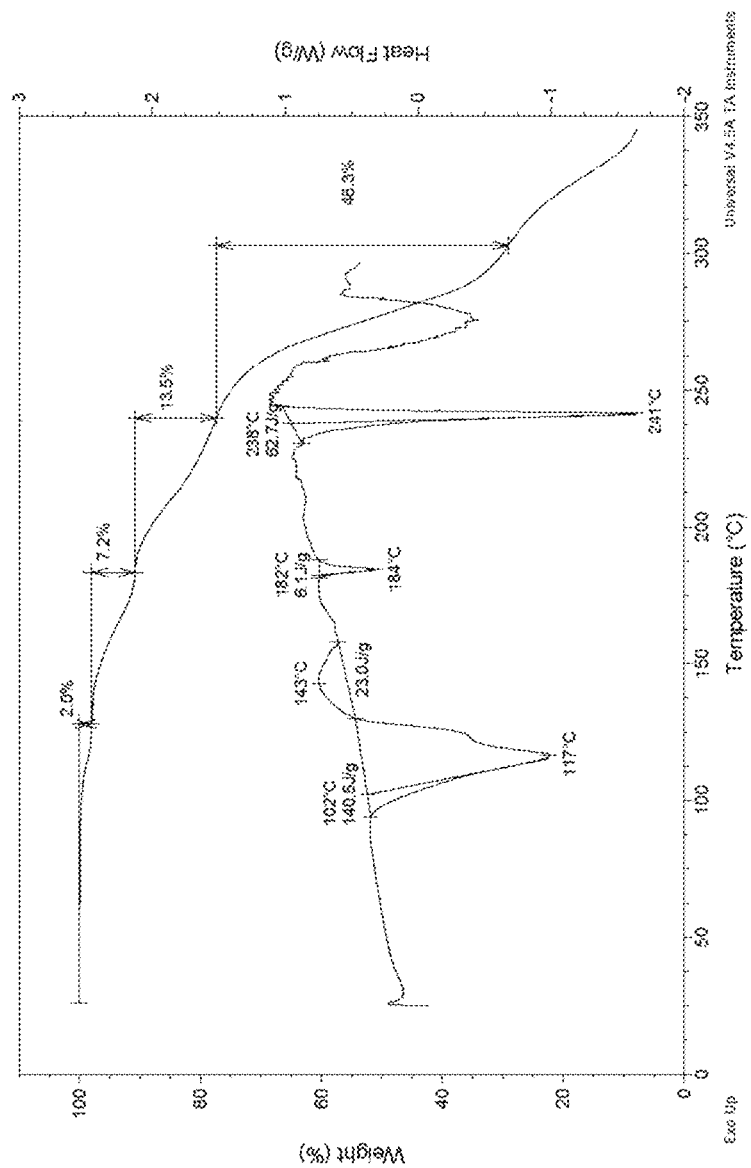
FIG. 29 provides an overlay of TGA and DSC thermograms for a scaled up material prepared from nicotine and orotic acid in EtOAc (exhibiting XRPD Orotate Pattern 2)
Figure 30:
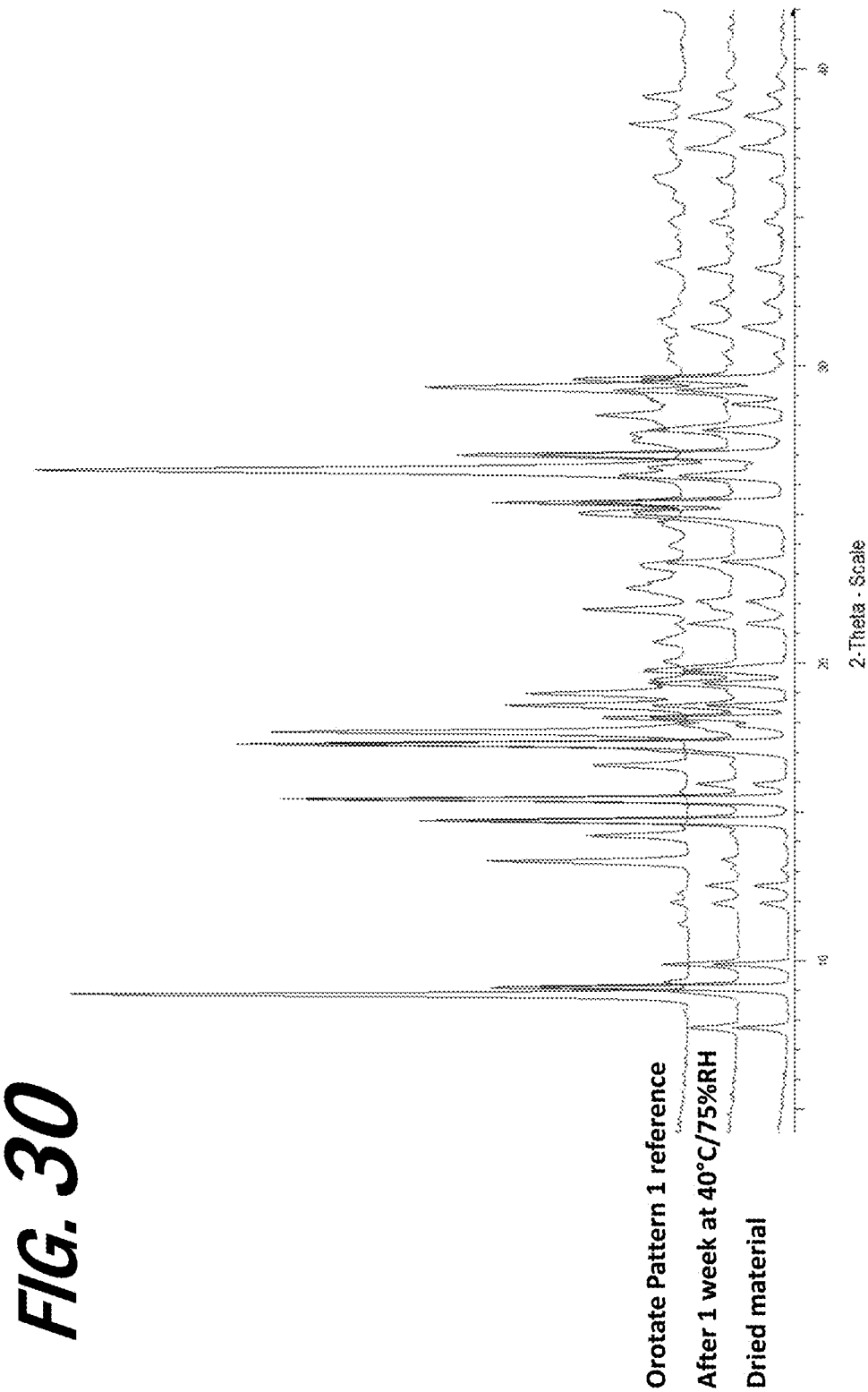
FIG. 30 is an XRPD diffractogram for a static stability test with a scaled up material prepared from nicotine and orotic acid in EtOAc (exhibiting XRPD Orotate Pattern 2)

In another form, the nicotine orotate (believed to be a mono-orotate hemi-hydrate salt) can be described as exhibiting an XRPD pattern (referred to herein as "Orotate Pattern 2") with peaks at one or more of the following 2-theta angles: 9.1, 14.7, 15.4, 17.3, 25.0, 25.4, and 27.0. Full characterization data, including a table of all relevant peaks in the x-ray diffraction pattern is provided in Example 1. See also FIGS. 22-30, providing the results of various methods of characterization of a scaled up sample of this (Orotate Pattern 2/mono-orotate hemihydrate salt) material. It is noted that a variable temperature XRPD experiment conducted with this material showed a conversion of Orotate Pattern 2 to Pattern 1 on heating (liberating water and nicotine). A first endotherm seen in the DSC is the melt of Pattern 2, with the release of the water and an exotherm seen is the re-crystallization of Pattern 1, with associated loss of nicotine (second weight loss in the TGA). No change was seen in the diffractogram or visually at 180-200° C.; as such, the cause of this endotherm in the DSC (but repeat DSC experiments showed that it is reproducible). The final endotherm and associated weight loss is the dissociation of the mono-salt and release of the remainder of the nicotine to leave orotic acid. See FIG. 29. This was confirmed by a $^1$H NMR experiment with the residue, which was consistent with orotic acid.

Figure 2:
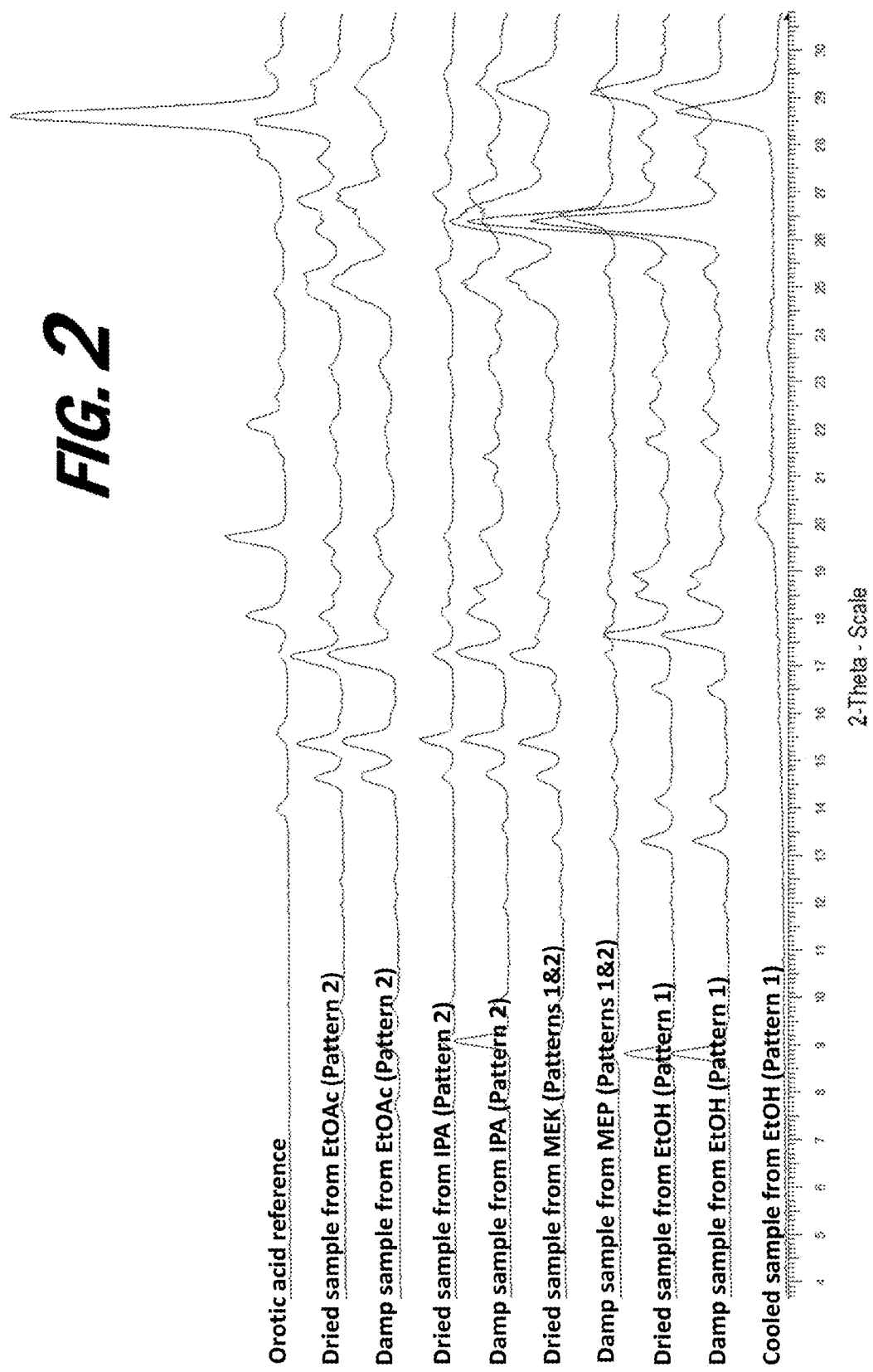
FIG. 2 provides additional XRPD diffractograms of solid materials prepared from nicotine and orotic acid by various methods.
Figure 3:
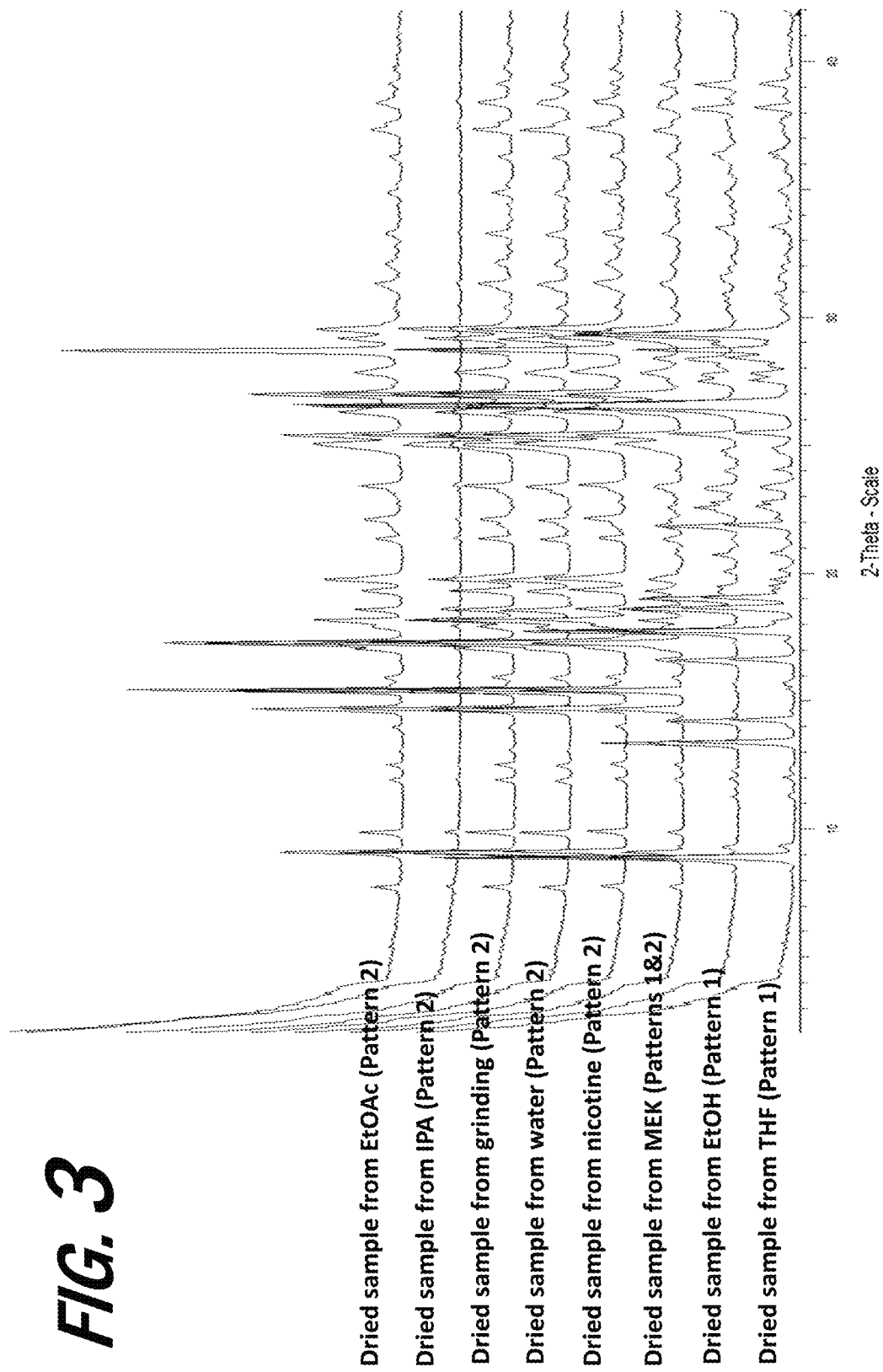
FIG. 3 provides high resolution XRPD diffractograms of solid materials prepared from nicotine and orotic acid by various methods.
Figure 4:
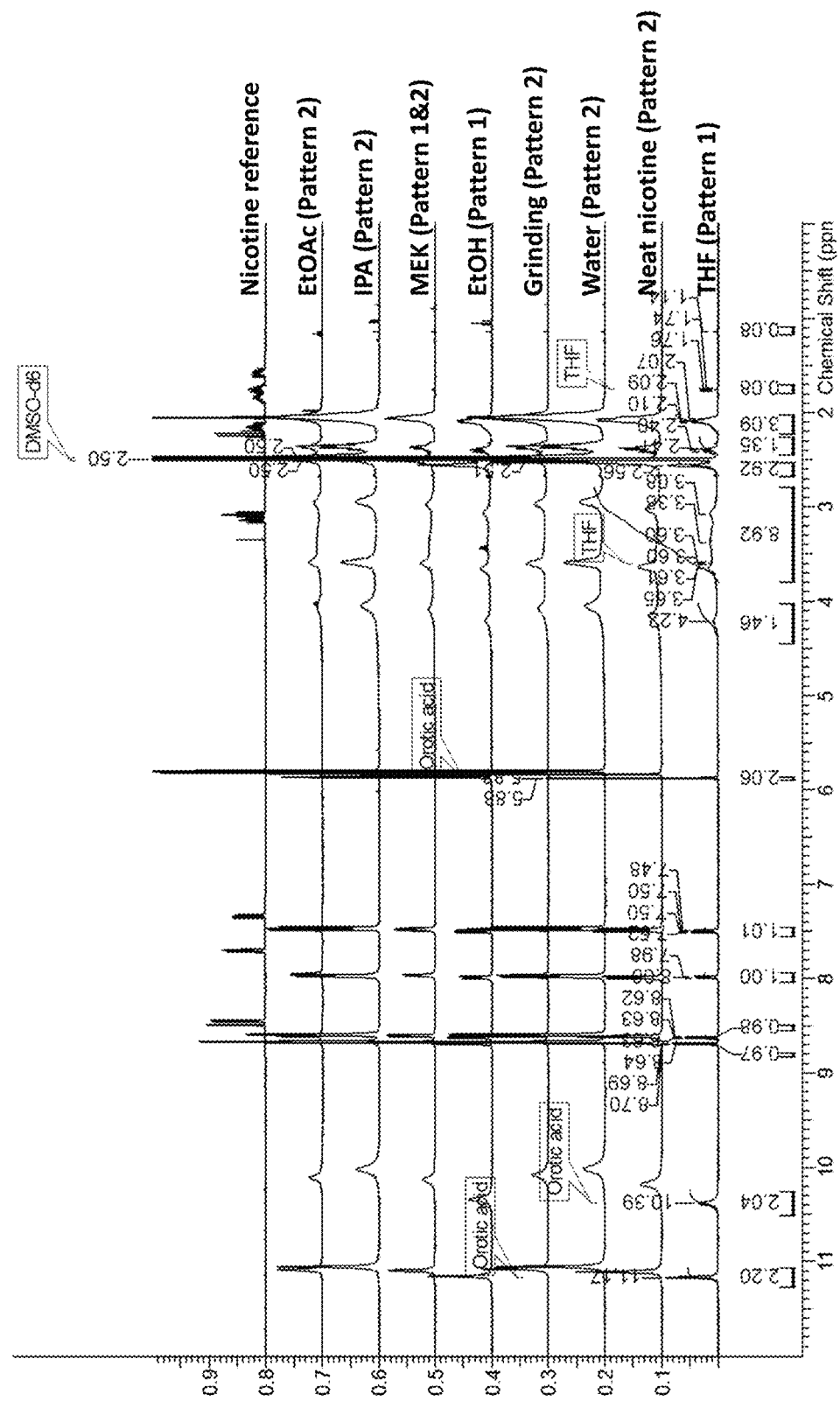
FIG. 4 provides $^1$H NMR spectra of solid materials prepared from nicotine and orotic acid by various methods.
Figure 5:
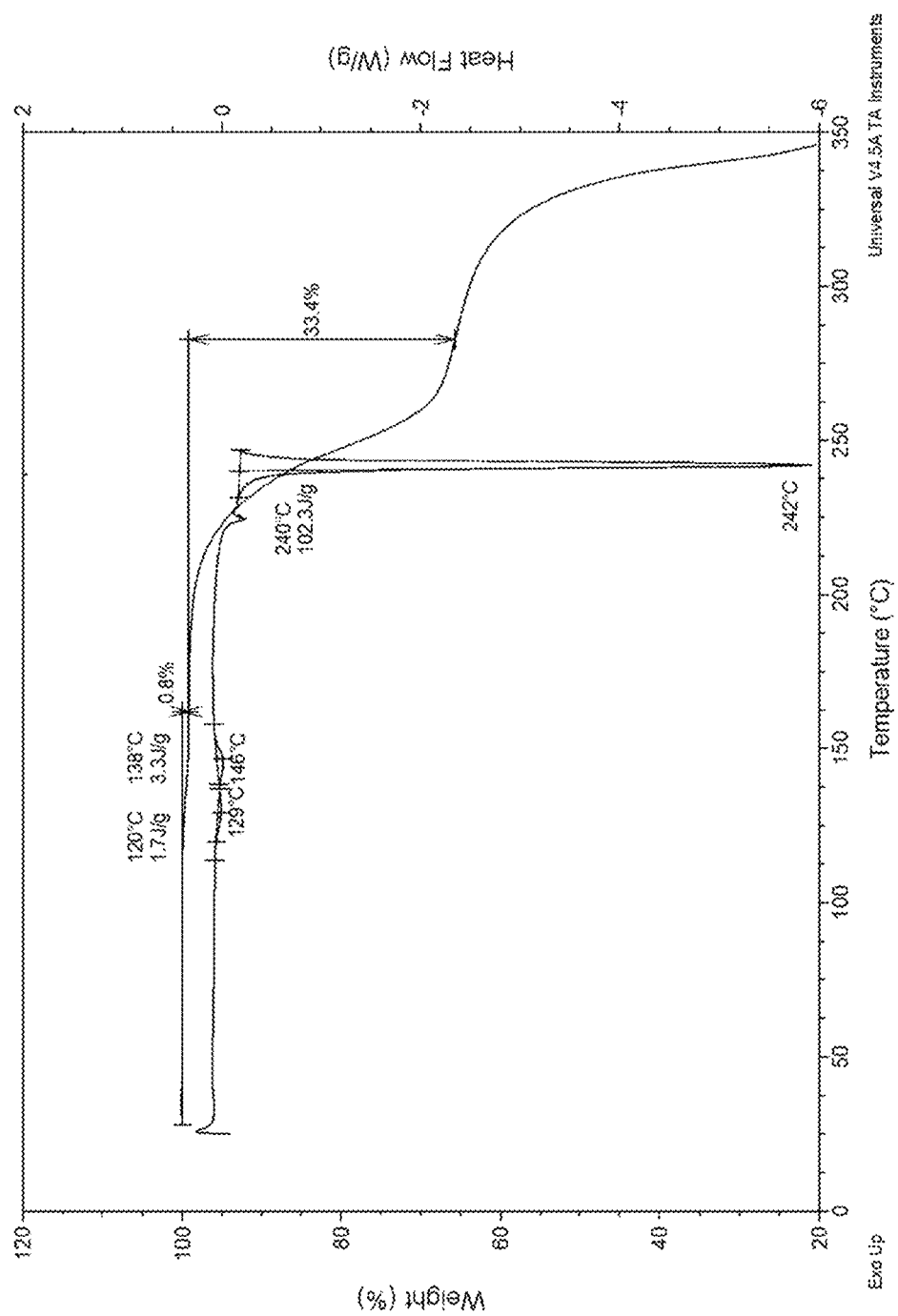
FIG. 5 provides an overlay of thermogravimetric analysis (TGA) and differential scanning calorimetry (DSC) thermograms for a material prepared from nicotine and orotic acid in THF.
Figure 6:
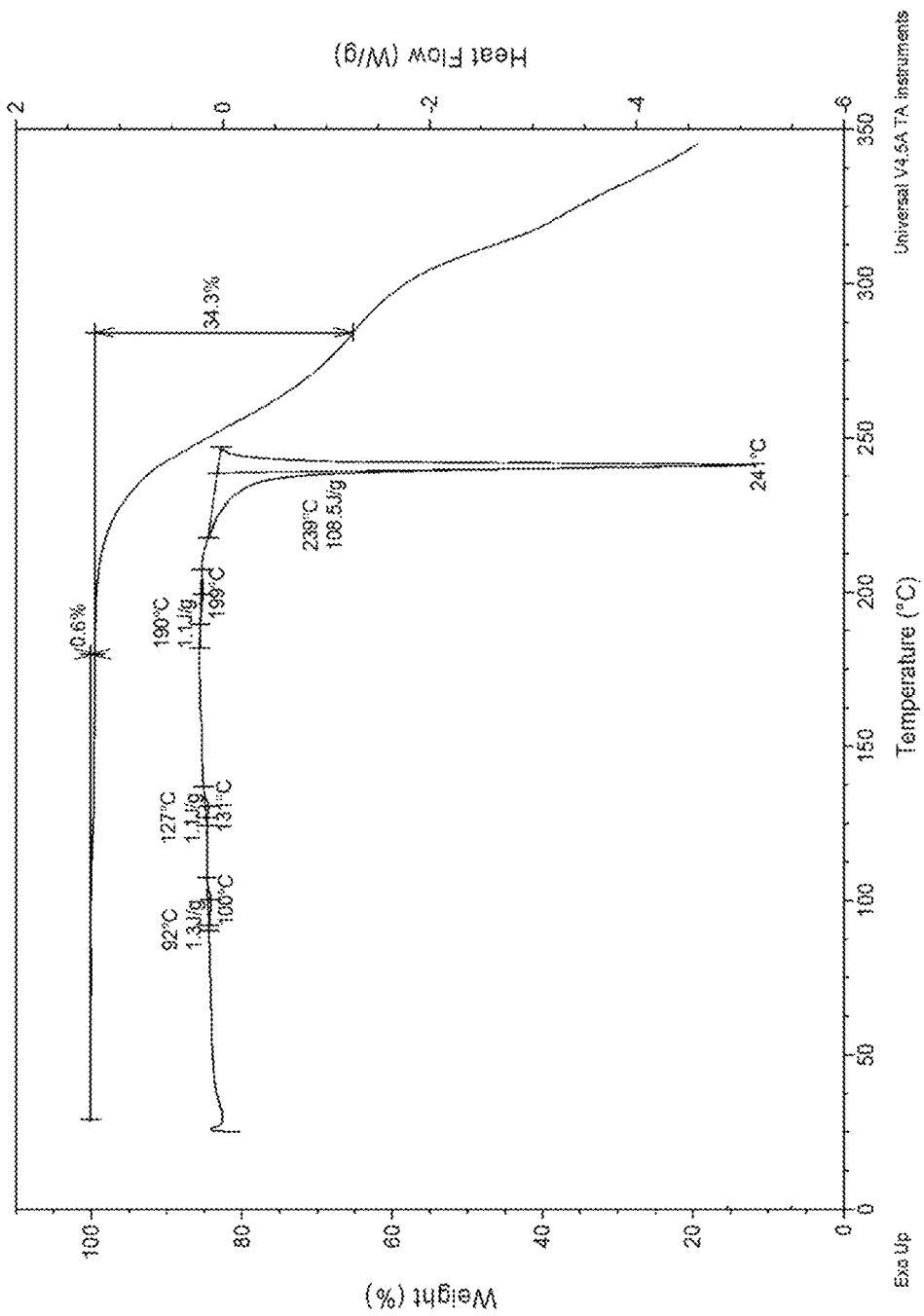
FIG. 6 provides an overlay of TGA and DSC thermograms for a material prepared from nicotine and orotic acid in ethanol (EtOH)
Figure 7:
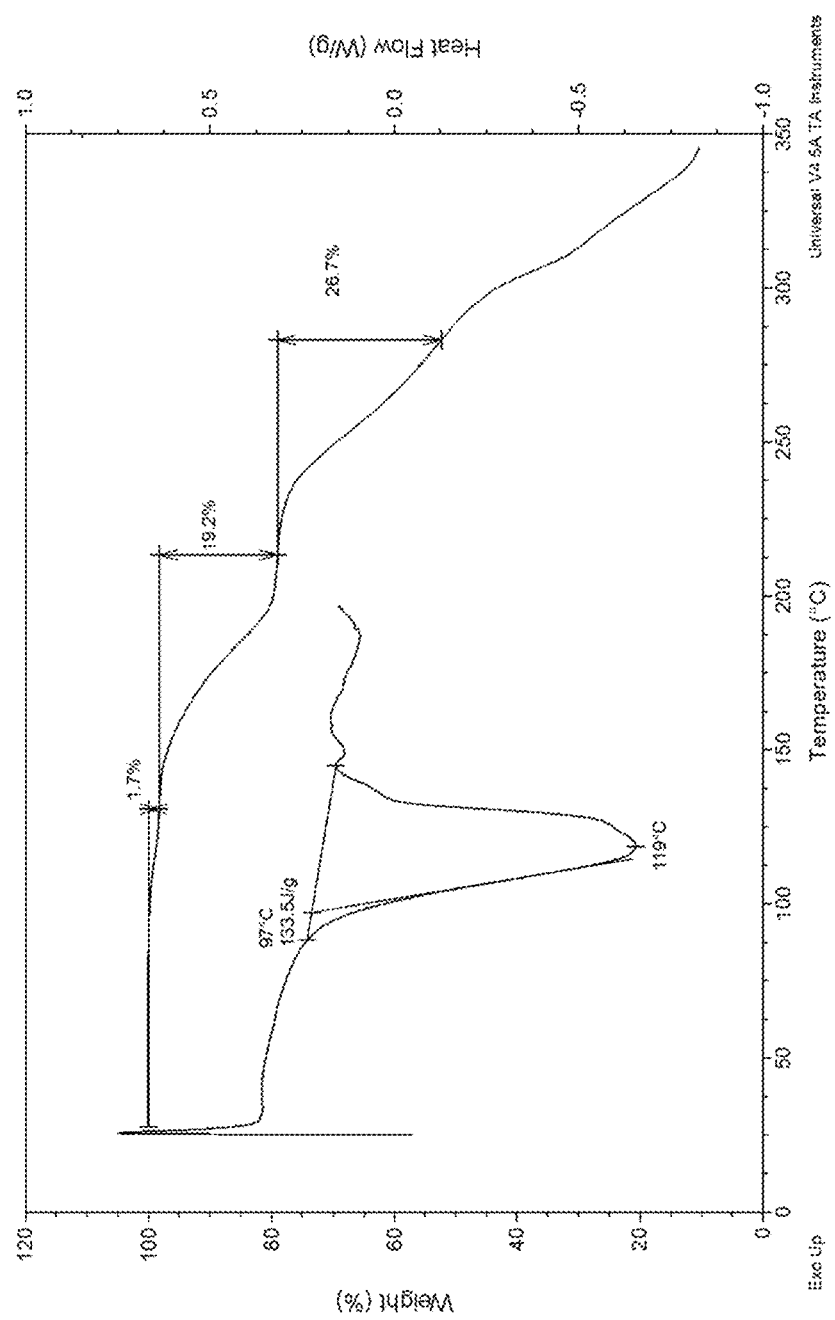
FIG. 7 provides an overlay of TGA and DSC thermograms for a material prepared from nicotine and orotic acid in neat nicotine.
Figure 8:
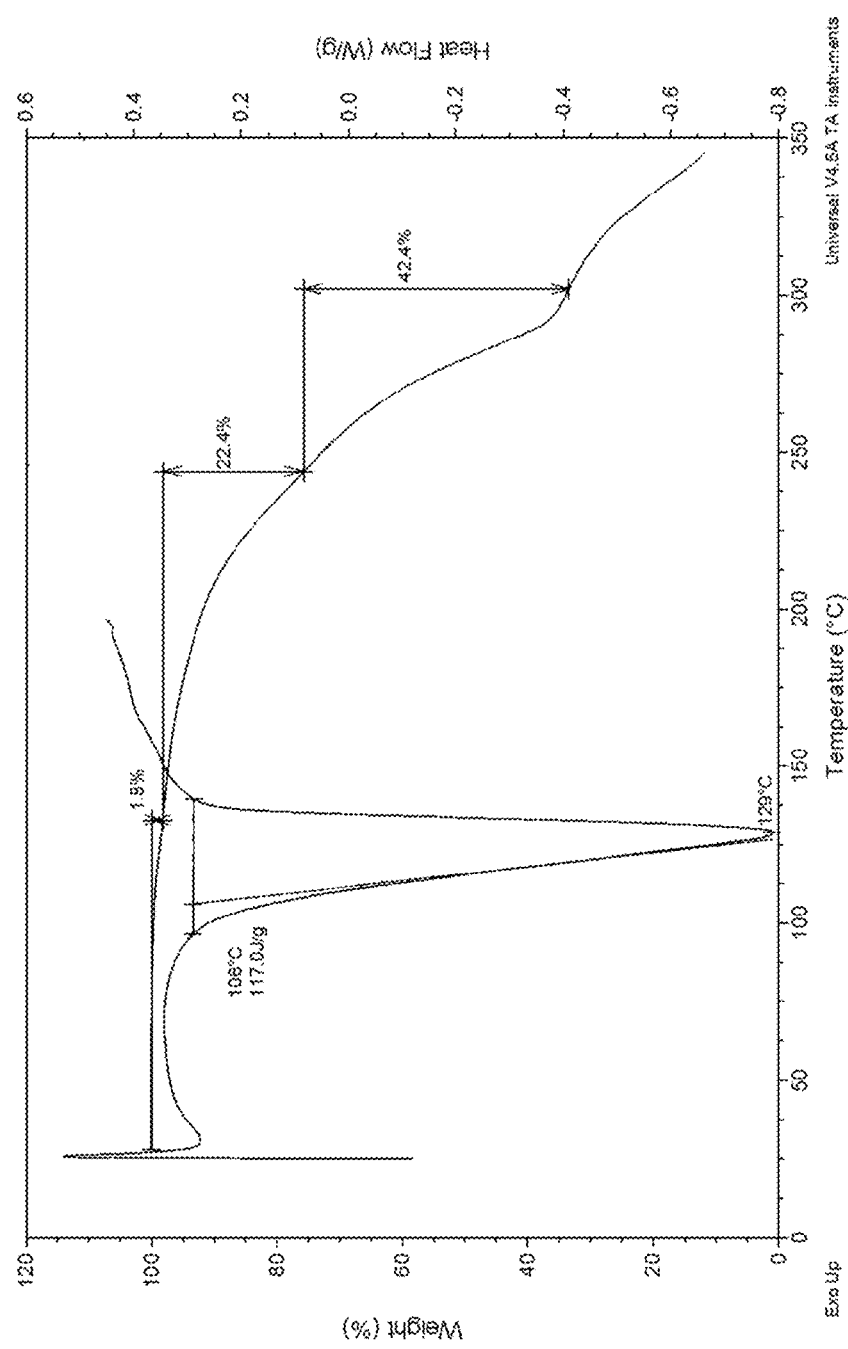
FIG. 8 provides an overlay of TGA and DSC thermograms for a material prepared from nicotine and orotic acid in water.
Figure 9:
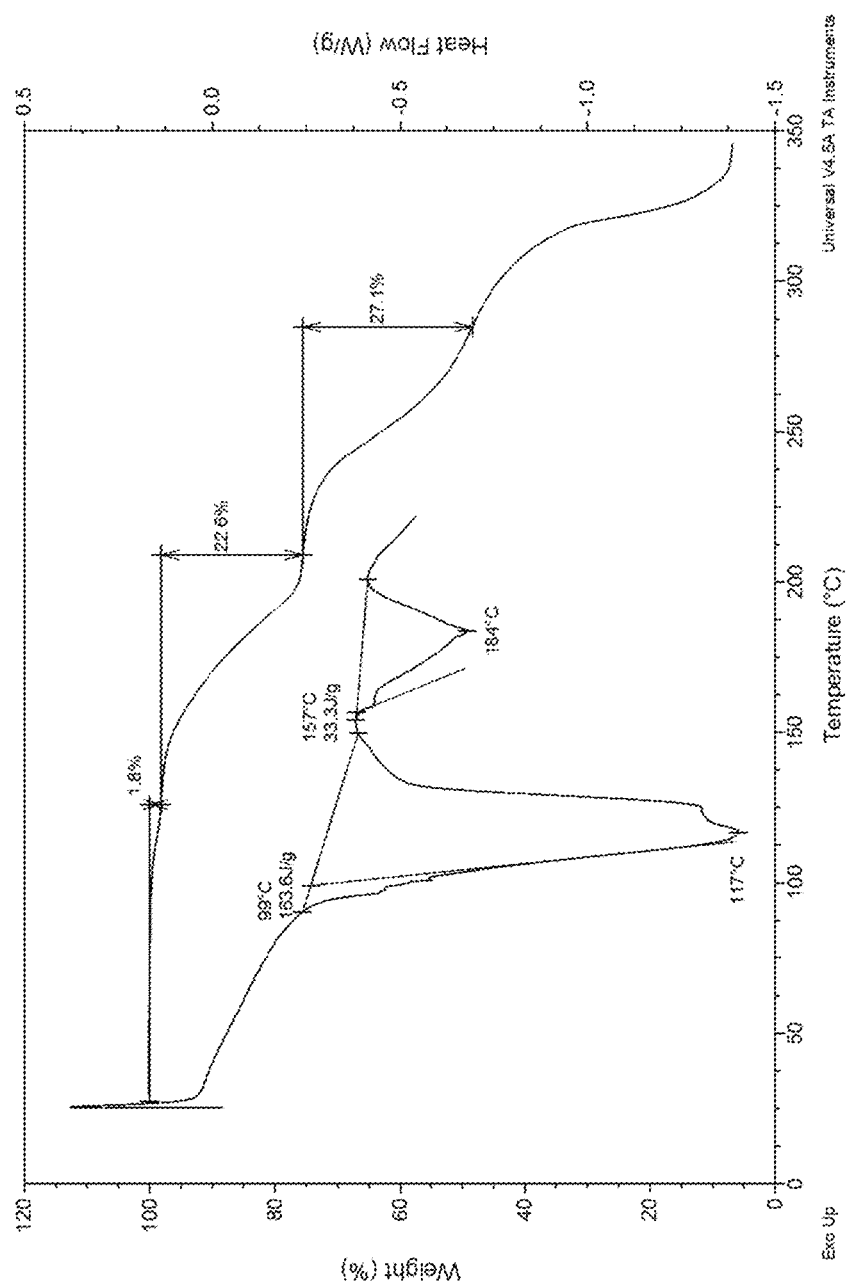
FIG. 9 provides an overlay of TGA and DSC thermograms for a material prepared from nicotine and orotic acid via grinding.
Figure 10:
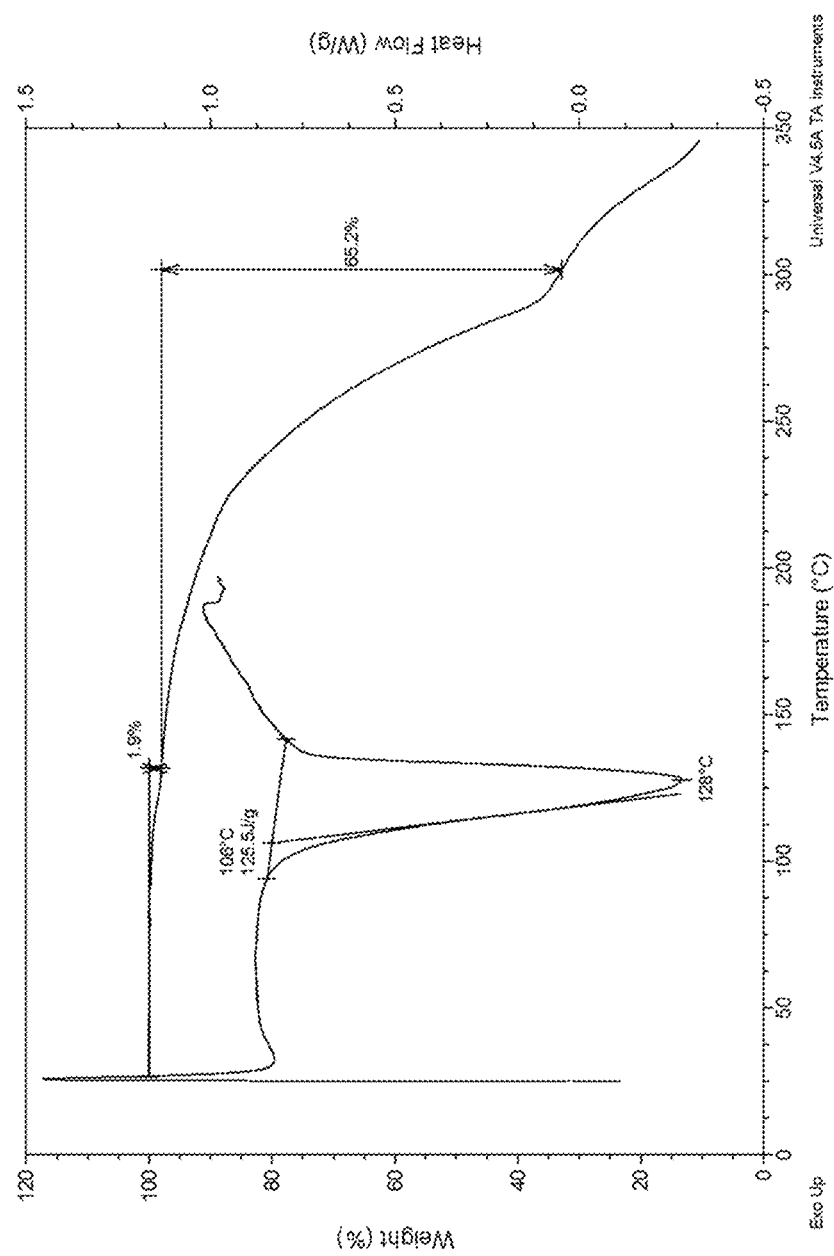
FIG. 10 provides an overlay of TGA and DSC thermograms for a material prepared from nicotine and orotic acid in a mixture of propan-2-ol (IPA) and water (80/20, v/v)
Figure 11:
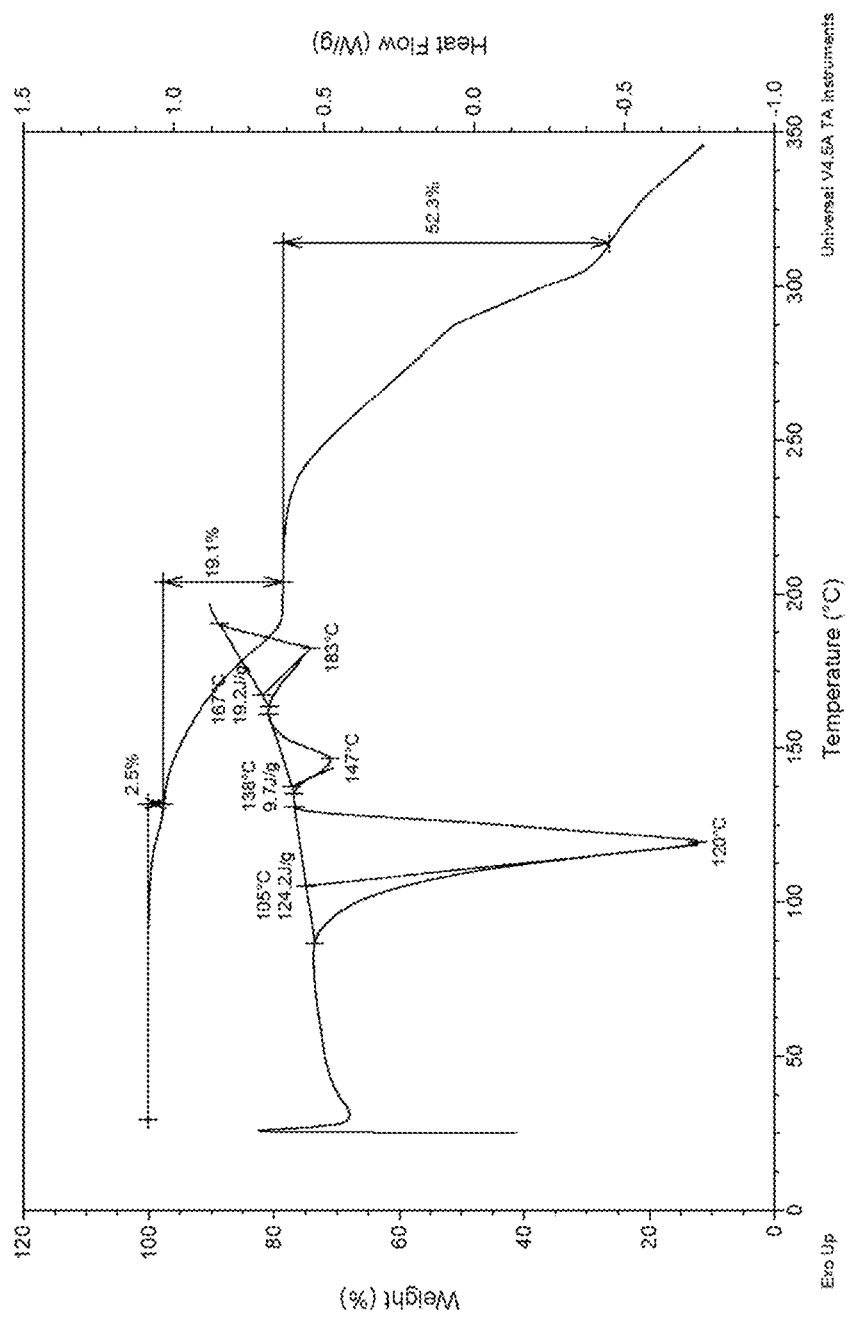
FIG. 11 provides an overlay of TGA and DSC thermograms for a material prepared from nicotine and orotic acid in ethyl acetate (EtOAc)
Figure 12:
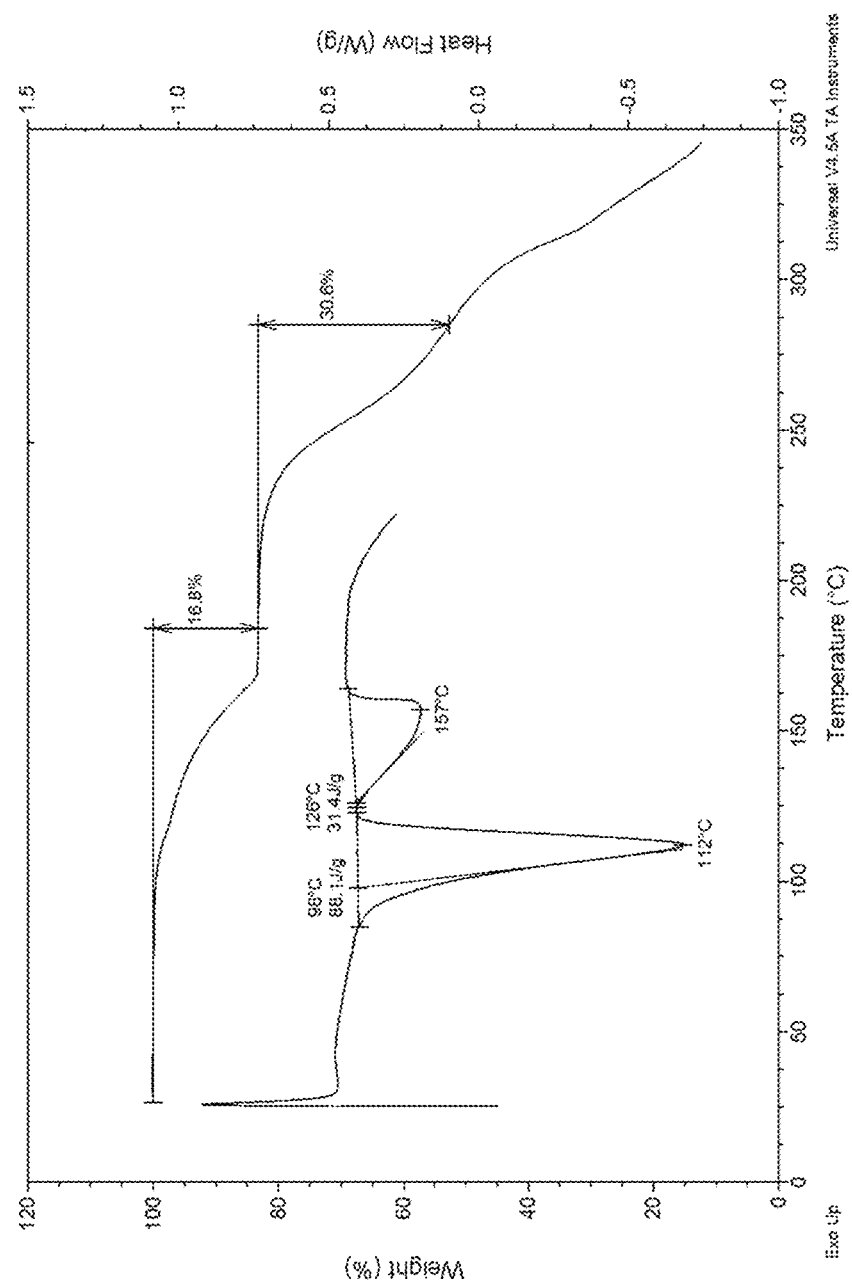
FIG. 12 provides an overlay of TGA and DSC thermograms for a material prepared from nicotine and orotic acid in methyl ethyl ketone (MEK)
Figure 13:
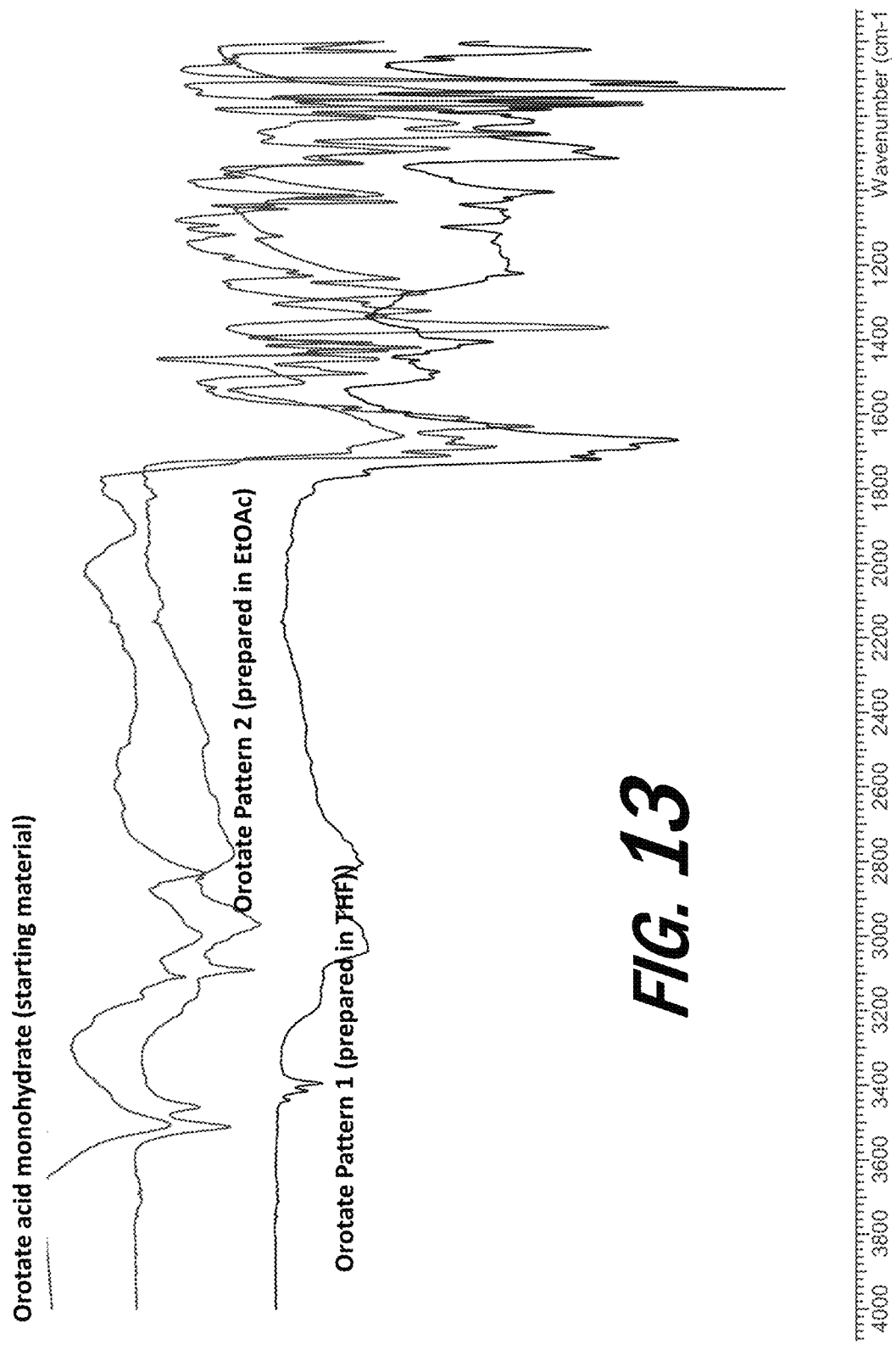
FIG. 13 provides an overlay of FT-IR spectra of nicotine orotate salts exhibiting XRPD Patterns 1 and 2 and orotic acid.

In certain embodiments, the specific form of nicotine orotate can be affected by the solvent in which it is prepared. For example, a material prepared in THF or EtOAc was found to produce a material exhibiting Orotate Pattern 1, whereas a material prepared in neat nicotine, water, IPA/water, EtOAc, or by grinding was found to produce a material exhibiting Orotate Pattern 2. See FIGS. 1-3 for XRPD traces comparing solid materials obtained through various solvent screen studies, described in greater detail in Example 1. FIG. 4 provides $^1$H NMR spectra comparing the materials. FIGS. 5-12 provide overlays of TGA and DSC thermograms of materials obtained in various solvents. Orotate Patterns 1 and 2 have a complex relationship; during crystallization studies, Pattern 1 was observed to precipitate initially and then convert to Pattern 2 upon stirring at 5° C. or on addition of excess nicotine.

Figure 14:
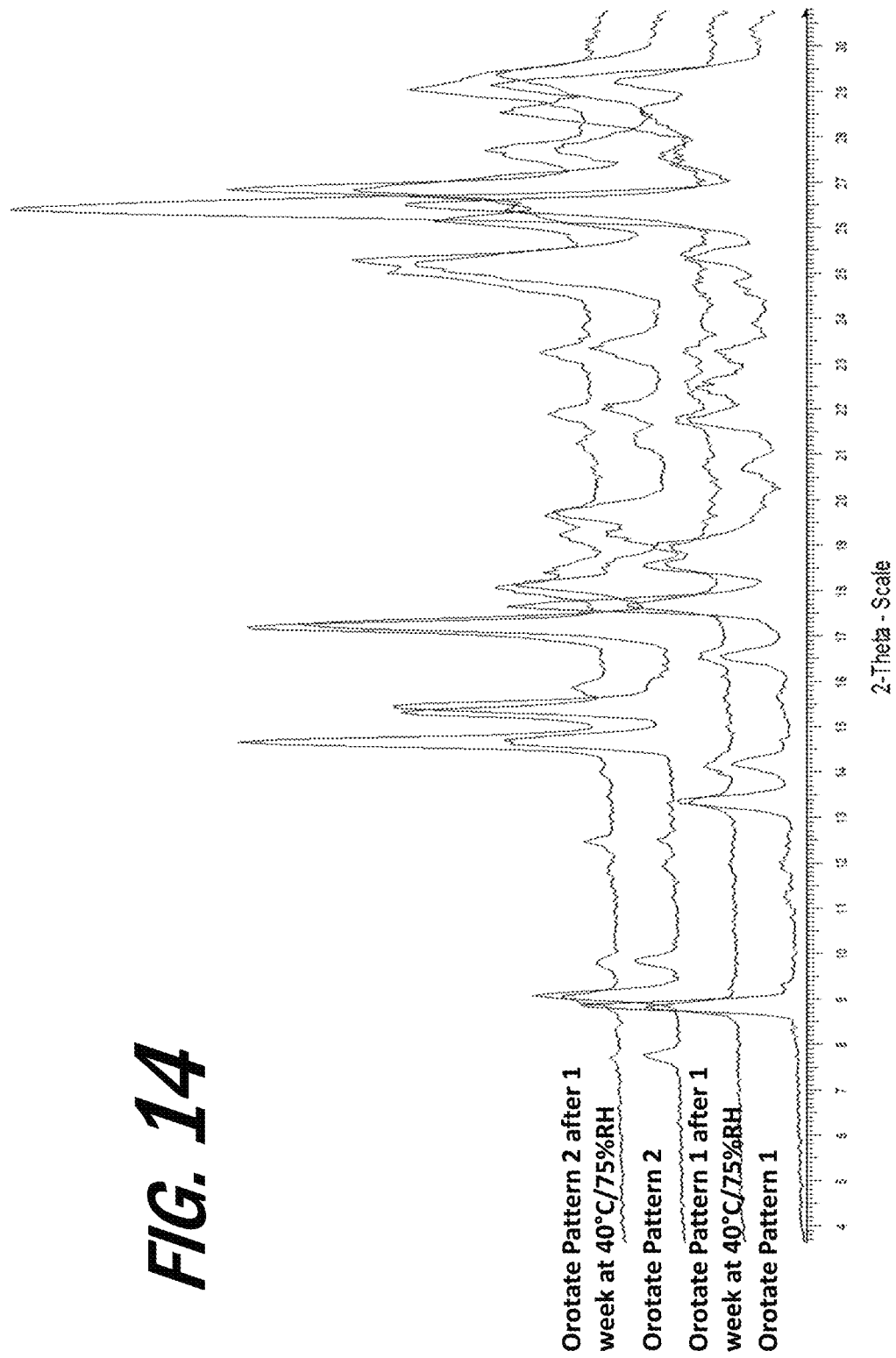
FIG. 14 provides XRPD diffractograms from materials prepared from nicotine and orotic acid by various methods, evaluating static stability of the salts.
Figure 15:
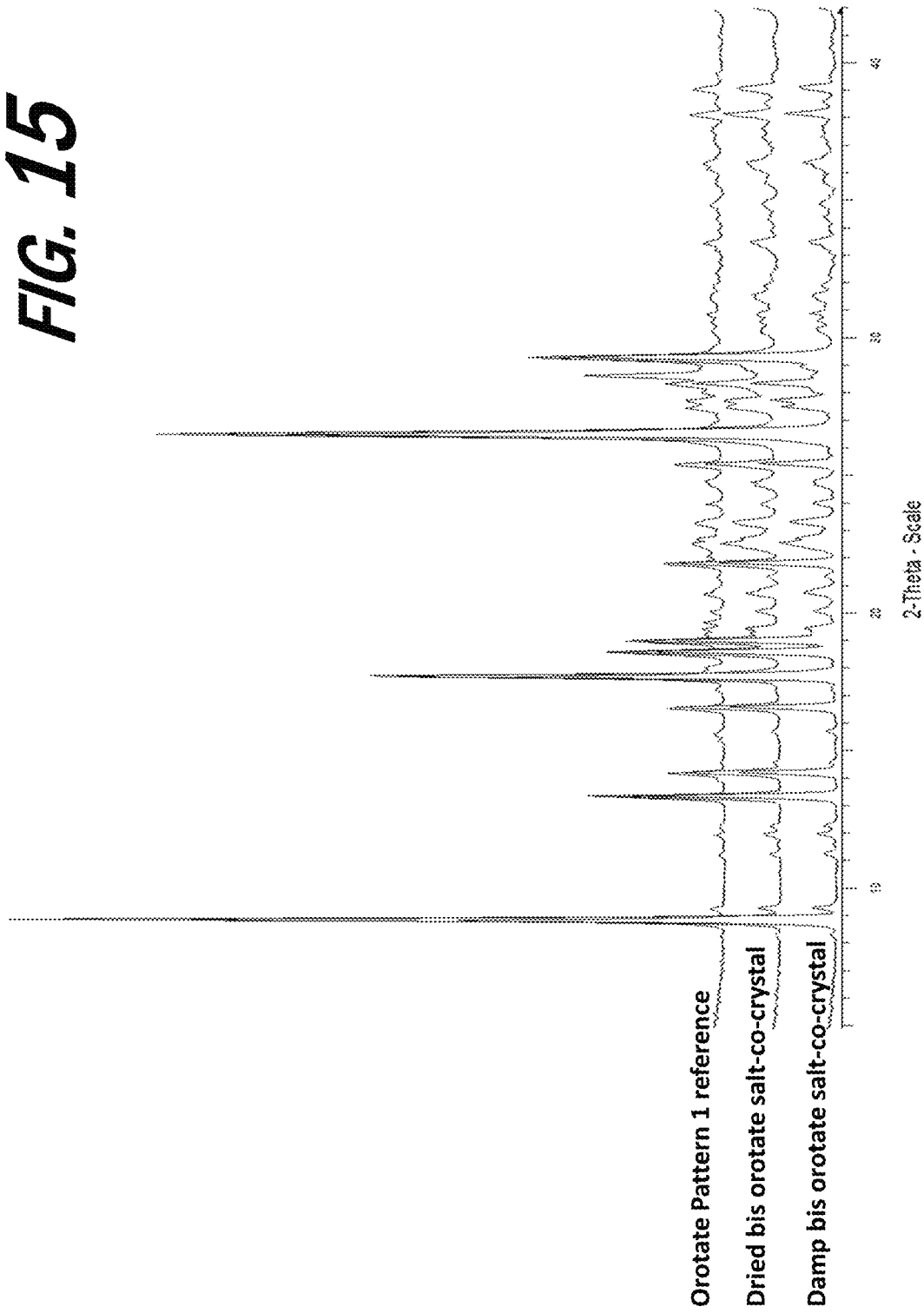
FIG. 15 provides XRPD diffractograms for scaled up material prepared from nicotine and orotic acid in THF (exhibiting XRPD Orotate Pattern 1, indicating a bis-orotate salt-co-crystal)
Figure 16:
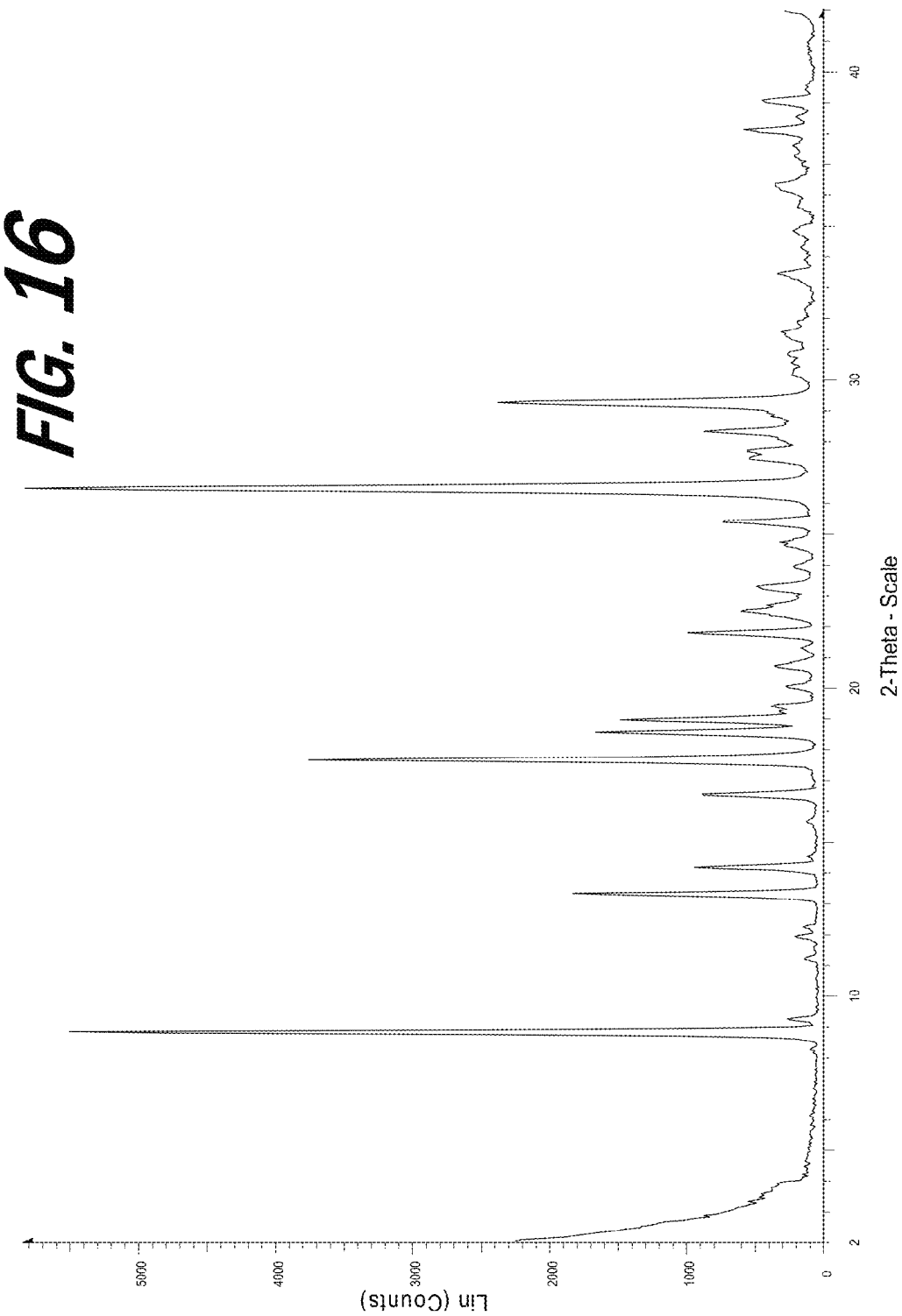
FIG. 16 provides a high-resolution XRPD reference diffractogram for scaled up material prepared from nicotine and orotic acid in THF (exhibiting XRPD Orotate Pattern 1)
Figure 17:
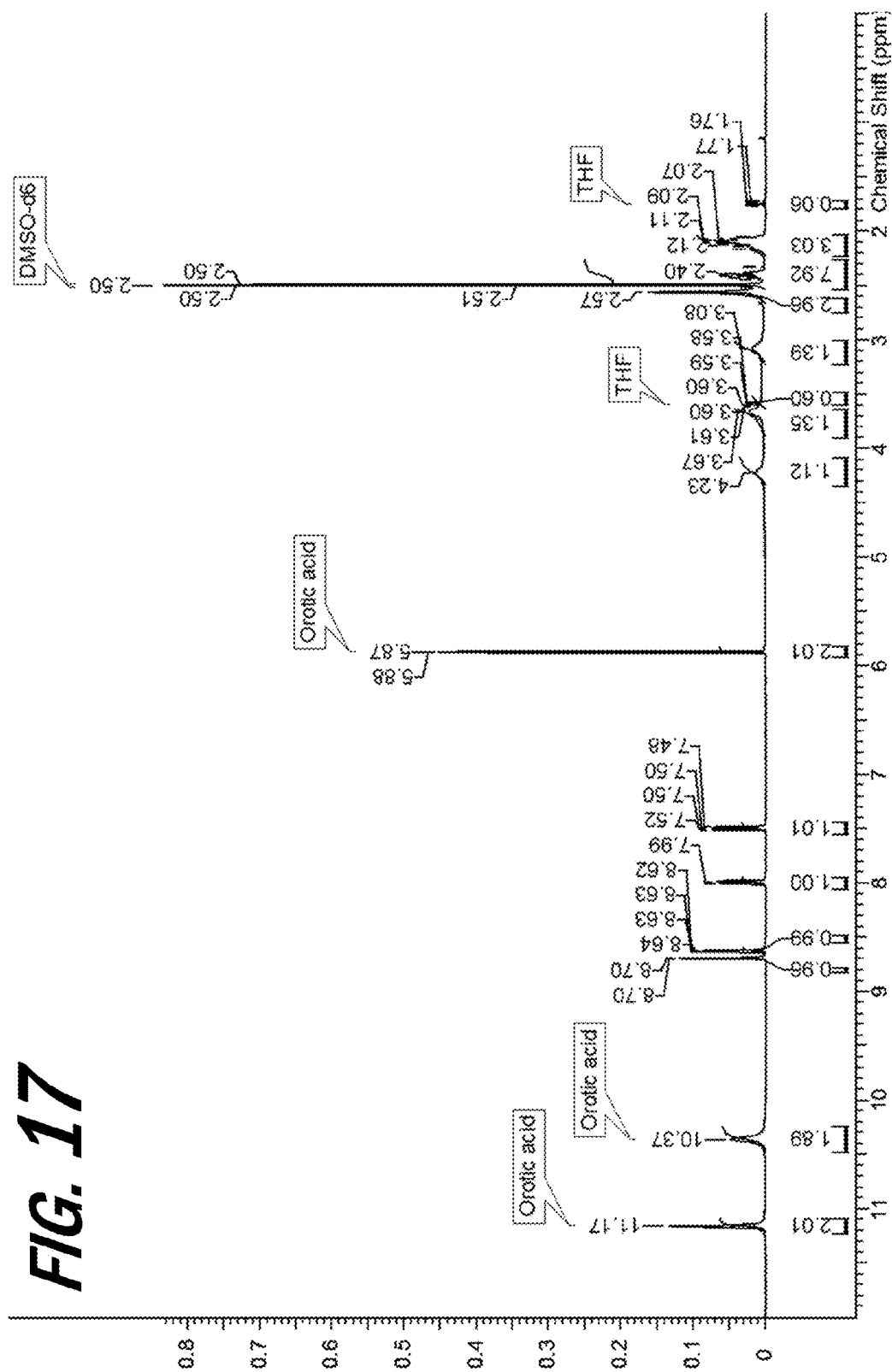
FIG. 17 provides a $^1$H NMR spectrum for scaled up material prepared from nicotine and orotic acid in THF (exhibiting XRPD Orotate Pattern 1)
Figure 18:
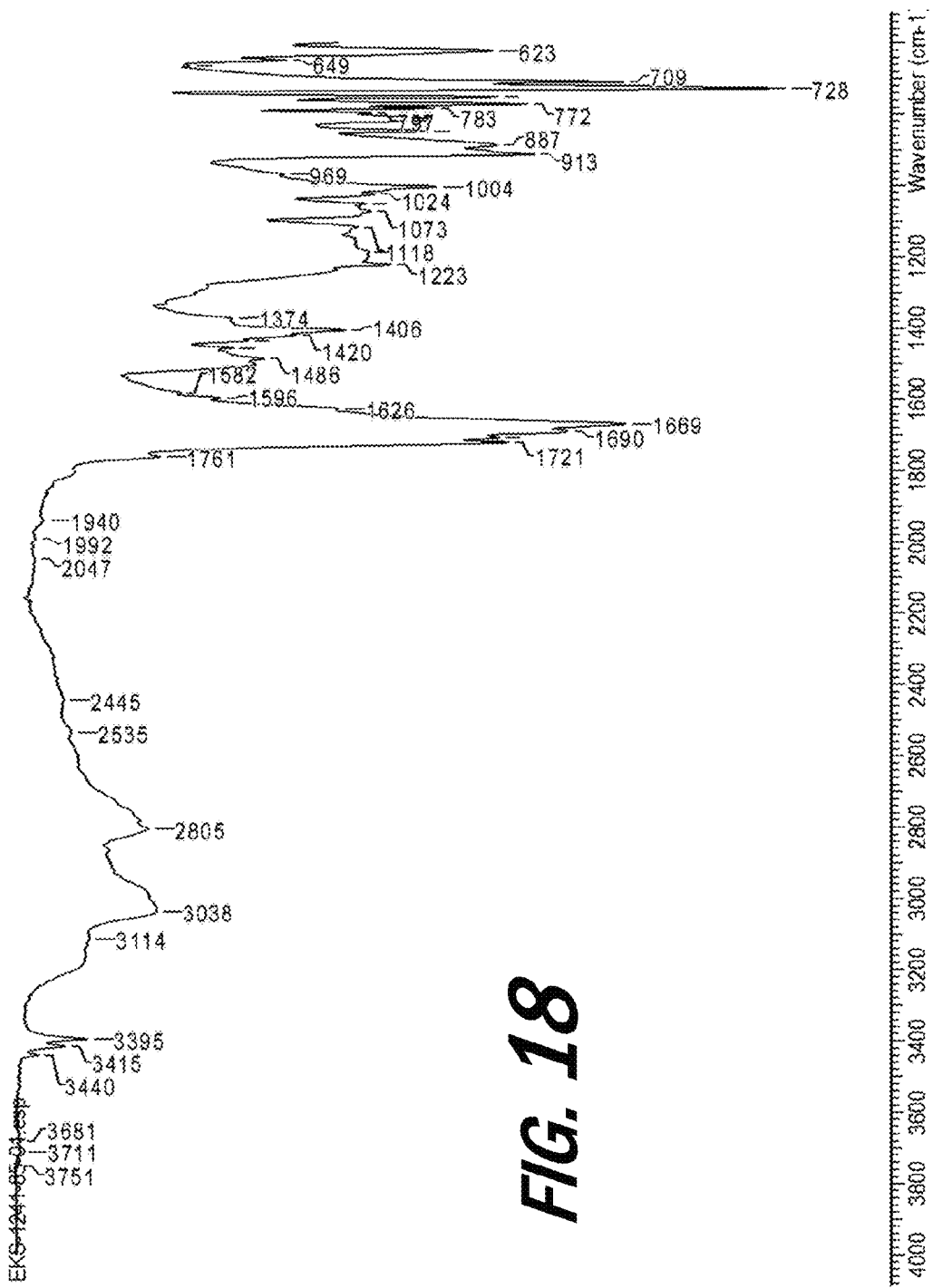
FIG. 18 provides an FTIR spectrum of a scaled up material prepared from nicotine and orotic acid in THF (exhibiting XRPD Orotate Pattern 1)
Figure 21:
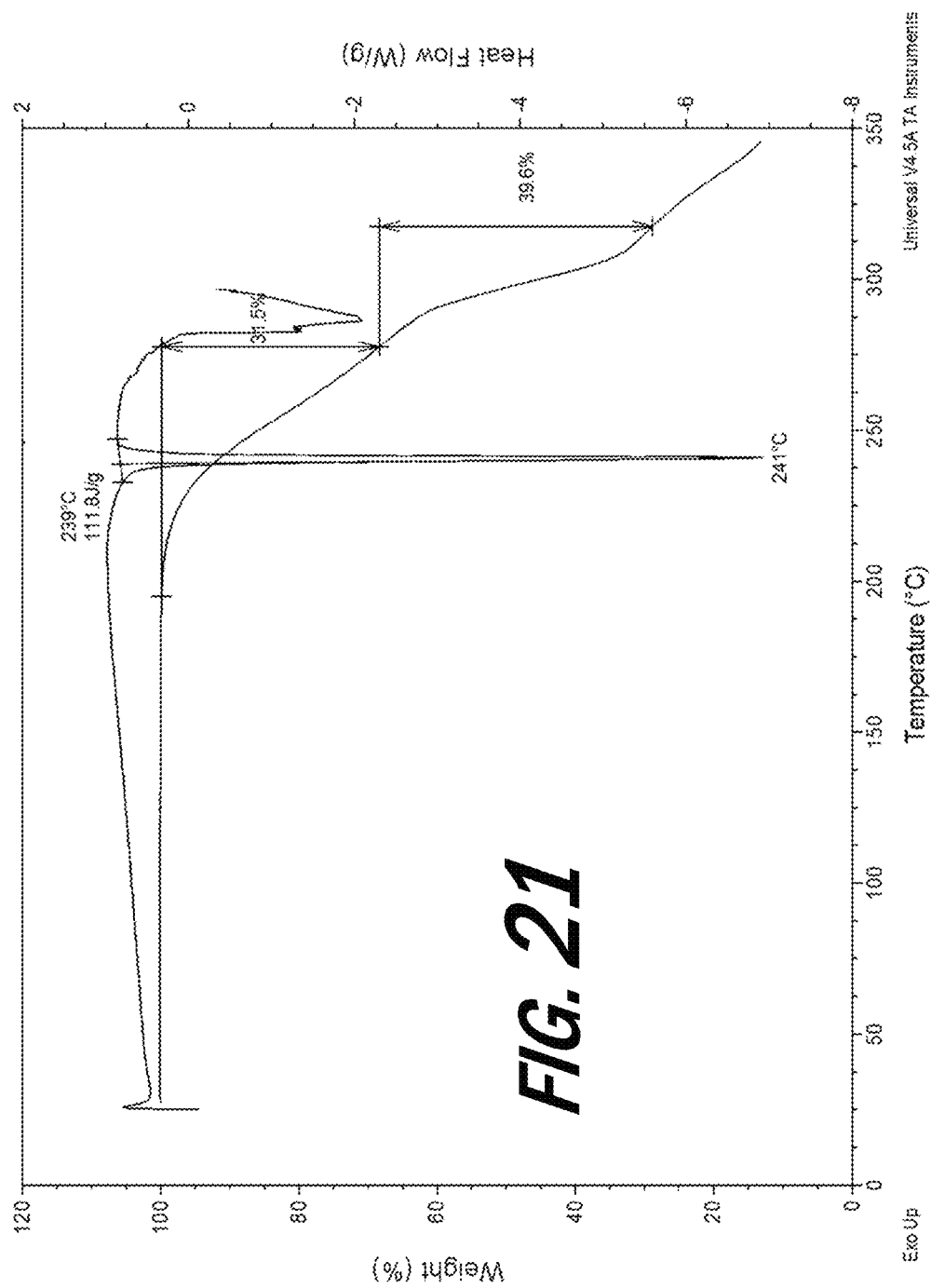
FIG. 21 provides an overlay of TGA and DSC thermograms for a scaled up material prepared from nicotine and orotic acid in THF (exhibiting XRPD Orotate Pattern 1)
Figure 22:
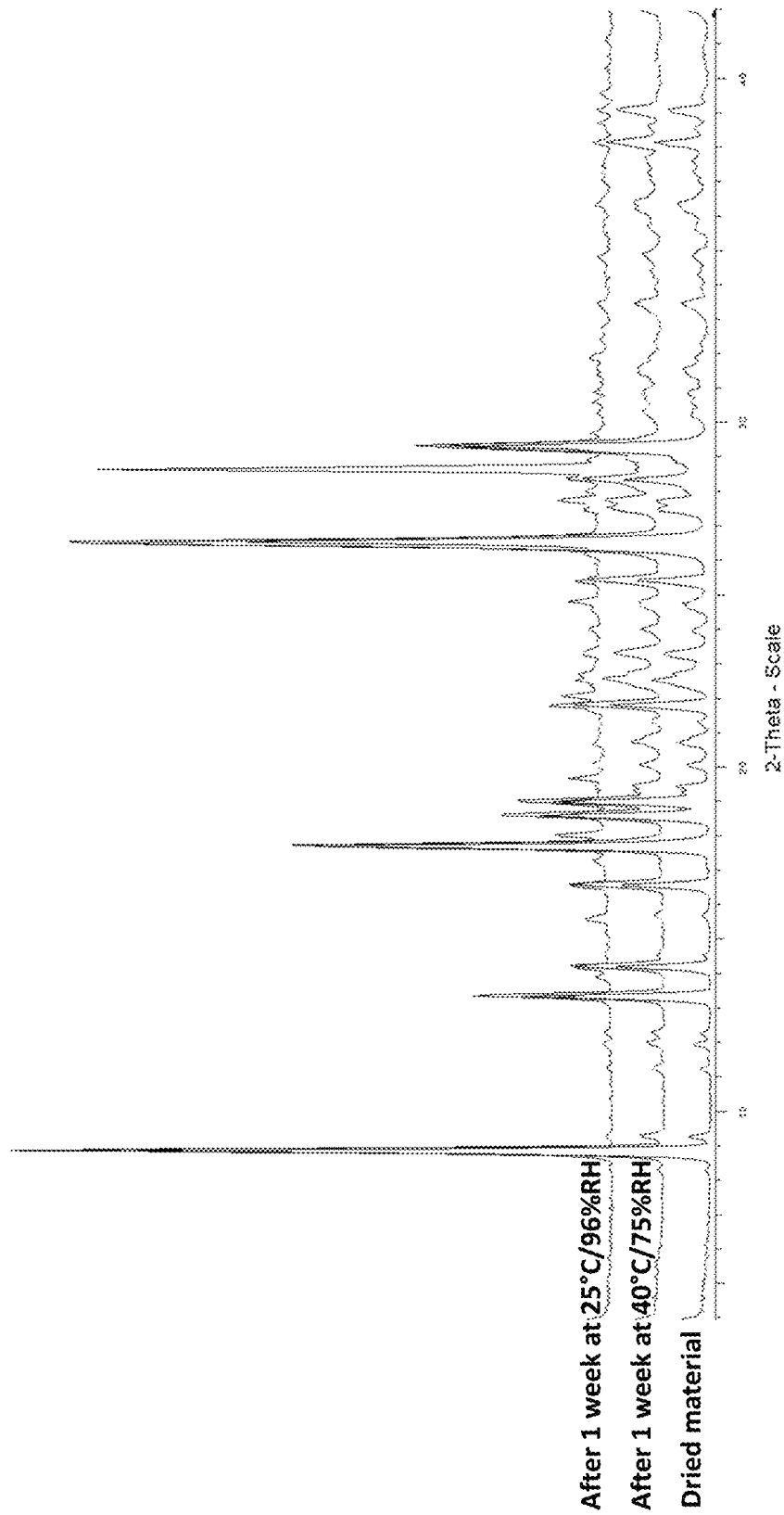
FIG. 22 provides XRPD diffractograms for a static stability test with scaled up material prepared from nicotine and orotic acid in THF (exhibiting XRPD Orotate Pattern 1)
Figure 23:
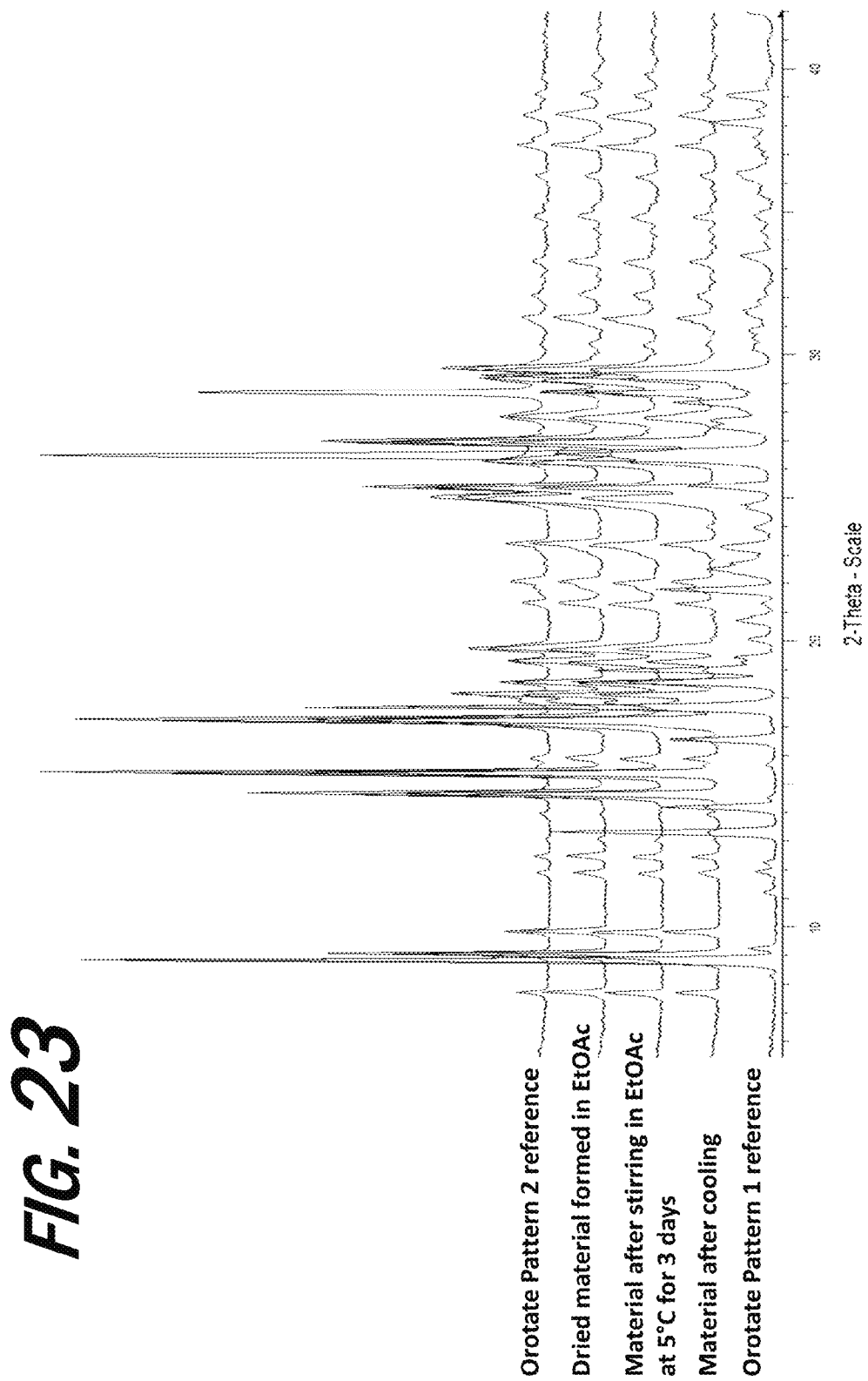
FIG. 23 provides high resolution XRPD diffractograms for a scaled up material prepared from nicotine and orotic acid in EtOAc, compared against a reference Orotate Pattern 1 XRPD diffractogram and a reference Orotate Pattern 2 XRPD diffractogram.
Figure 24:
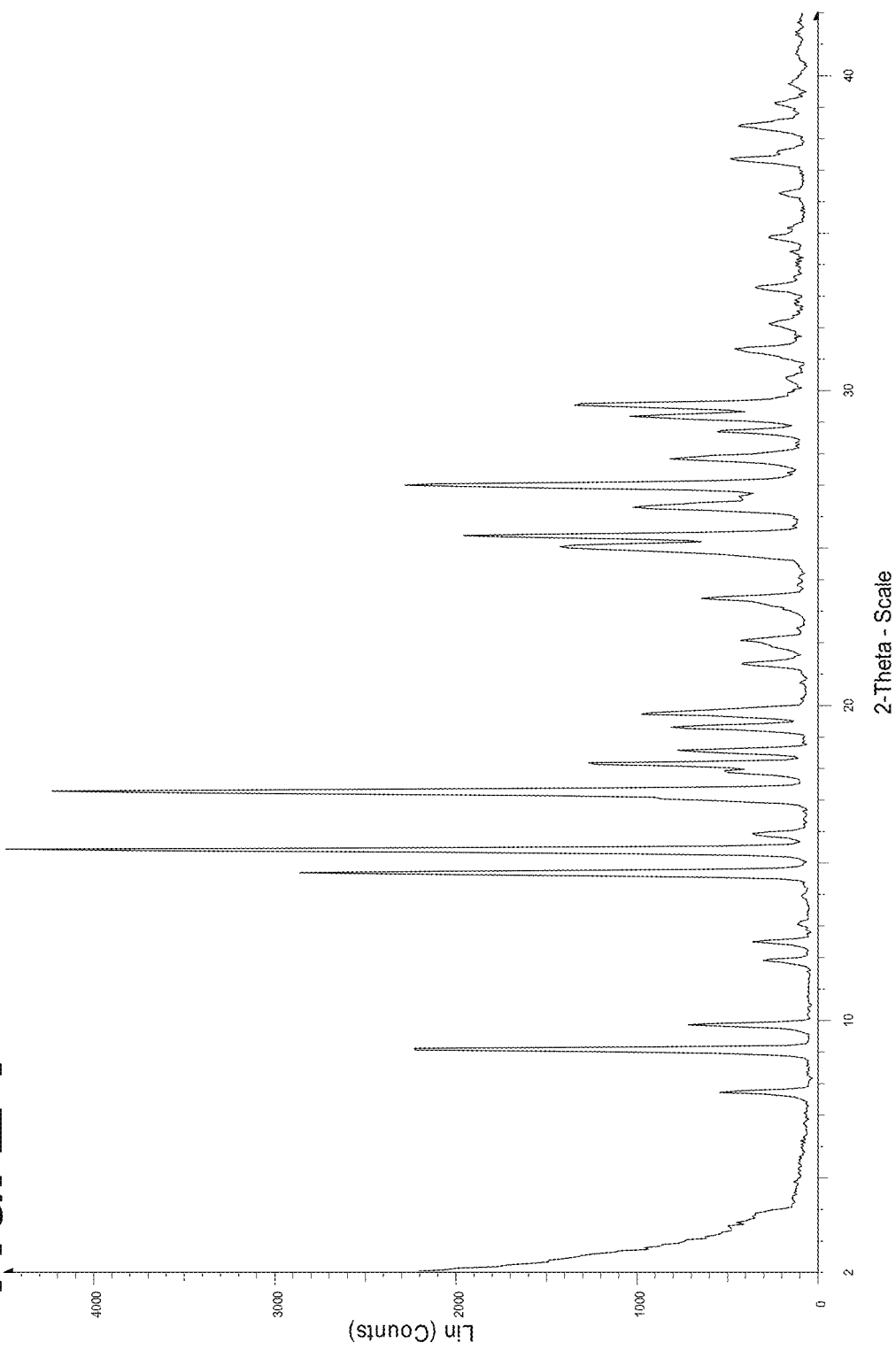
FIG. 24 provides a further high resolution XRPD reference diffractogram for a scaled up material prepared from nicotine and orotic acid in EtOAc (exhibiting XRPD Pattern 2, indicating a mono-orotate hemi-hydrate salt)
Figure 25:
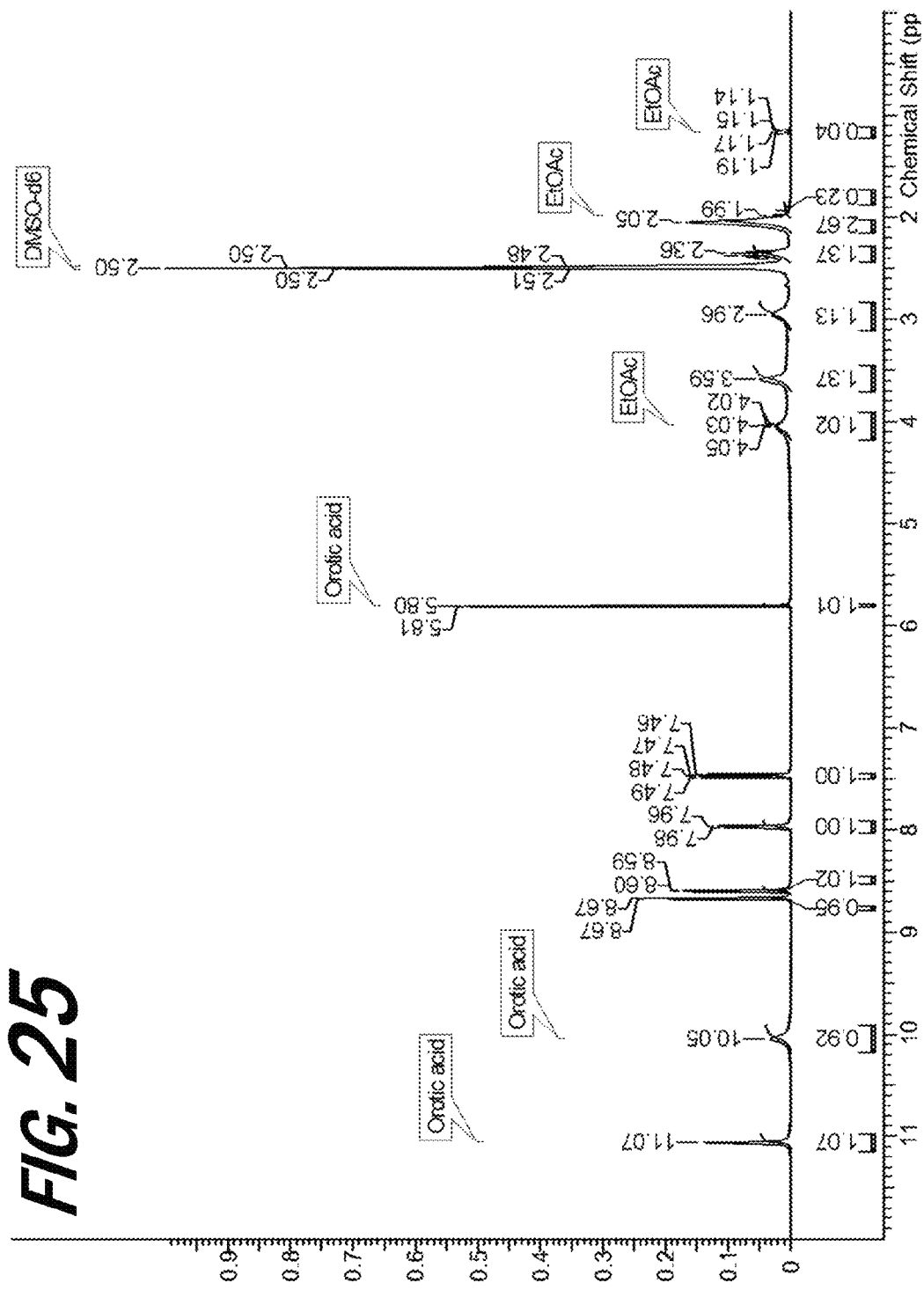
FIG. 25 provides $^1$H NMR spectra for a scaled up material prepared from nicotine and orotic acid in EtOAc (exhibiting XRPD Orotate Pattern 2)
Figure 26:
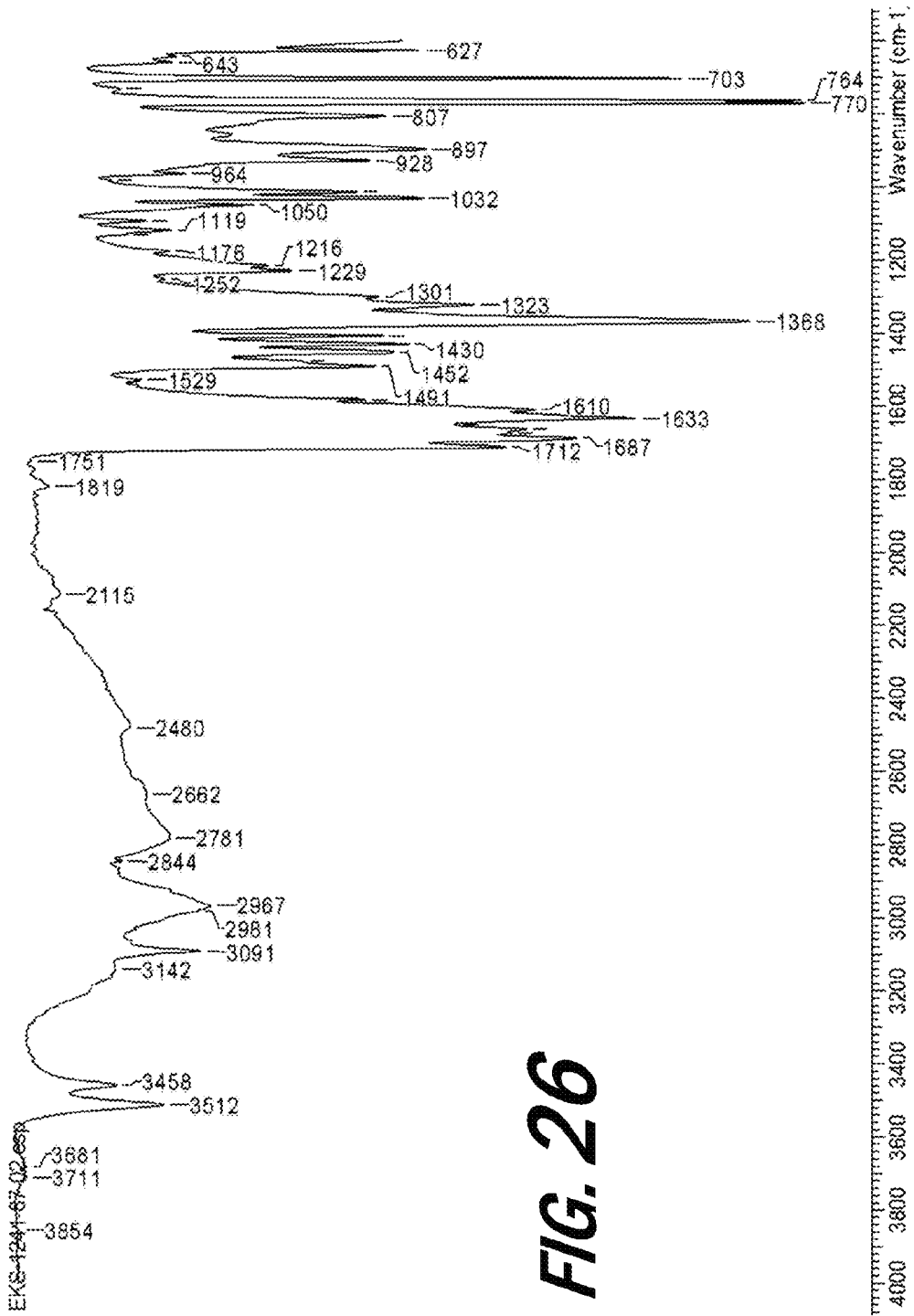
FIG. 26 provides an FT-IR spectrum of a scaled up material prepared from nicotine and orotic acid in EtOAc (exhibiting XRPD Orotate Pattern 2)
Figures 27, 28:
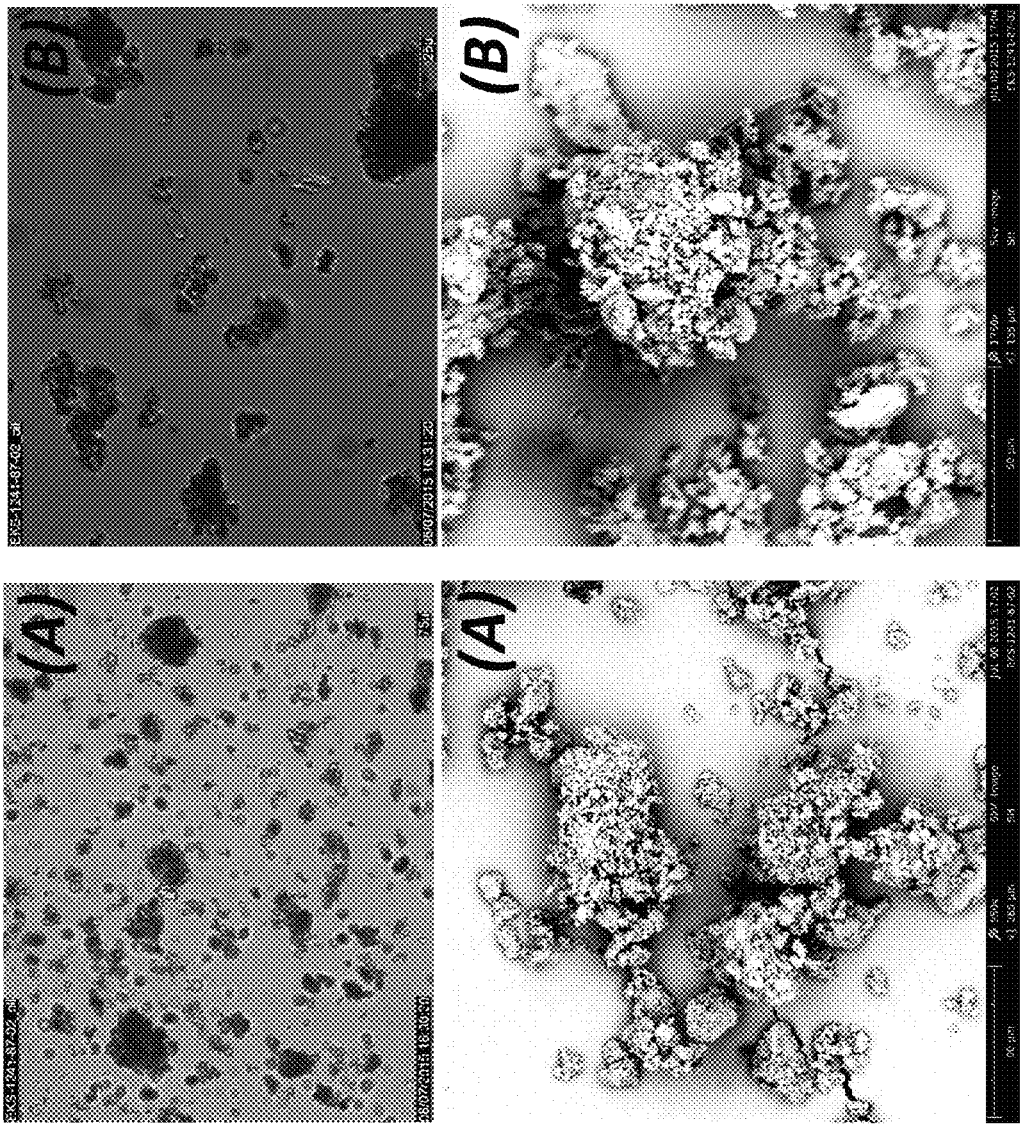
FIGS. 27(A) and 27(B) are microscopy images of a scaled up material prepared from nicotine and orotic acid in EtOAc (exhibiting XRPD Orotate Pattern 2)
FIGS. 28(A) and 28(B) are SEM images for a scaled up material prepared from nicotine and orotic acid in EtOAc (exhibiting XRPD Orotate Pattern 2)

The stabilities of these two solid forms of nicotine orotate (exhibiting XRPD Orotate Pattern 1 and Orotate Pattern 2) are analyzed by XPRD in dry form and after 1 week at 40° C./75% relative humidity, as shown in FIG. 14. This study (and others) demonstrate that the bis-orotate salt-co-crystal is thermally stable (melting at 239° C.) and the bis-orotate salt-co-crystal was shown to only slightly hygroscopic in GVS experiments. However, longer exposure to high humidity (25° C./96% RH for 1 week) caused conversion to a runny material.

In another embodiment, a salt of nicotine and fumaric acid is provided. The stoichiometry of the fumarate salt provided herein can vary. For example, in certain embodiments, a nicotine orotate salt or salt-co-crystal is provided having a stoichiometry of between about 1:2 nicotine:acid and about 1:1 nicotine:acid (i.e., having at least about 1 equivalent of acid per nicotine).

Again, varying the method by which the fumaric acid and nicotine are combined (e.g., by combining in different solvents) can, in some embodiments, provide different forms. One particular form isolated according to the present disclosure (exhibiting an XRPD pattern referred to herein as "Fumarate Pattern 1") is a non-solvated mono-salt. See FIG. 39. This form can be prepared, e.g., in THF or by grinding. This nicotine fumarate can, in some embodiments, be described as exhibiting an XRPD pattern with peaks at one or more of the following 2-theta angles: 14.9, 18.4, 19.9, and 22.4. Full characterization data, including a table of all relevant peaks in the x-ray diffraction pattern is provided in Example 2. In certain embodiments, this nicotine fumarate salt form is prone to deliquescing at high humidity and may not re-crystallize when humidity is reduced. In other embodiments, a metastable polymorph of the mono-fumarate salt is provided. This form can be prepared, e.g., in neat nicotine.

In another embodiment, a salt of nicotine and pyroglutamic acid is provided, with further detail provided in Example 3. This material is believed to exhibit some degree of crystallinity.

One skilled in the art will understand that all diffraction pattern data provided herein should not be construed as absolute and, accordingly, the nicotine salts and salt co-crystals of the invention are not limited to particles having XRPD patterns identical to those in the referenced figures. Any nicotine salts, co-crystals, or salt co-crystals having XRPD patterns substantially the same as those of the relevant figures will be considered to fall within the scope of the invention. A person skilled in the art of X-ray powder diffraction is able to judge the substantial identity of X-ray powder diffraction patterns. Generally, a measurement error of a diffraction angle in an X-ray powder diffractogram is about 2-theta=0.5° or less (more suitably, about 2-theta=, 0.2° or less) and such degree of a measurement error should be taken into account when considering the X-ray powder diffraction pattern in the figures provided herewith and/or the peak values provided herein.

In other words, the peaks in the figures and the peak values given throughout the specification can be viewed, in certain embodiments, as being +/−0.5° or +/−0.2°. See Fundamentals of Powder Diffraction and Structural Characterization, Pecharsky and Zavalij, Kluwer Academic Publishers, 2003.

Other nicotine salts, co-crystals, and salt co-crystals are also encompassed by the present disclosure. For a list of pharmaceutically acceptable counter-ions, see Handbook of Pharmaceutical Salts—Properties, Selection, and Use, P. Heinrich Stahl, Camille G. Wermuth (Eds.) VHCA (Verlag Helvetica Chemica Acta—Zürich), Wiley-VCH (New York) 2002, which is incorporated herein by reference. For example, certain coformers useful for reaction with the nicotine, which may result in the formation of a salt, co-crystal, or salt co-crystal include, but are not limited to: acetic acid; adipic acid; ascorbic acid; capric (decanoic) acid; citric acid; D-glucuronic acid; D-gluconic acid; DL-lactic acid; L-lactic acid; galactaric (mucic) acid; hippuric (N-benzoylglycine) acid; hydrochloric acid; L-aspartic acid; L-glutamic acid; L-glutaric acid; glycerophosphoric acid;

glycolic acid; lauric acid; DL-malic acid; L-malic acid; DL-tartaric acid; L-tartaric acid; palmitic acid; phosphoric acid; sebacic (1,8-octanedicarboxylic) acid; stearic (octadecanoic) acid; succinic acid; sulfuric acid; and thiocyanic acid (HS—CN). Other exemplary coformers for reaction with the nicotine, which may result in the formation of a salt, co-crystal, or salt co-crystal include, but are not limited to, (+)-camphoric acid; 1,5-naphthalenedisulfonic acid; 1-hydroxy-2-naphthoic (xinafoic) acid; 2,5-dihydroxybenzoic (gentisic) acid; benzenesulfonic acid; benzoic acid; caprylic (octanoic) acid; cyclamic acid; ethanesulfonic acid; fumaric acid; D-glucoheptonic acid; 4-hydroxybenzoic acid; isobutyric acid; ketoglutaric (2-oxo-glutaric) acid; 2-ketobutyric acid; lactobionic acid; maleic acid; malonic acid; methanesulfonic acid; naphthalene-2-sulfonic acid; nicotinic acid; oleic (Z-octadecenoic) acid; orotic acid; oxalic acid; pamoic acid; pivalic acid; propionic acid; L-pyroglutamic acid; and p-toluenesulfonic acid.

Certain other types of coformers are generally associated with pharmacological effects and are not typically preferred for the preparation of salts, co-crystals, and salt co-crystals. Although complexes of nicotine with such coformers may not be preferred, in certain specialized embodiments, they may be reacted with nicotine to form salts, co-crystals, and/or salt co-crystals. Such coformers include, but are not limited to, (1S)-camphor-10-sulfonic acid; 4-acetamidobenzoic acid; 4-aminosalicylic acid, N-acetyl-4-aminosalicylic acid; caproic (hexanoic) acid; dichloroacetic acid; hydrobromic acid; DL-mandelic acid; L-mandelic acid; nitric acid; formic acid; salicylic acid; cinnamic (e.g., trans-cinnamic) acid; and undecylenic acid. Other exemplary coformers that may form salts, co-crystals, and/or salt co-crystals with nicotine include, but are not limited to, isothionic acid; lauric (dodecanoic) acid; 2-hydroxybenzoic acid; trans-2-hexanoic acid; trimesic acid; and 5-nitroisophthalic acid.

Various other coformers can be used to provide nicotine in the form of a salt, co-crystal, or co-crystal salt. Exemplary co-formers include, but are not limited to, L-proline, tromethamine; urea, xylitol; caffeine; glycine/glycine anhydride; vanillin; methyl 4-hydroxybenzoate (methylparaben); succinamide; L-alanine; mannitol; L-phenylalanine; saccharin; propylparaben; N-methylglucamine; L-tyrosine; gentisic acid; sorbic acid; benzoic acid; L-methionine; maltol; L-lysine, tromethamine; nicotinamide; isonicotinamide; phenylalanine; benzoquinone; terephthalaldehyde; 2,4-dihydroxybenzoic acid; and 4-hydroxybenzoic acid.

Additional coformers include pyruvic acid, 1-hydroxy-2-naphthoic acid, 4-aminobenzoic acid, 3,5-dihydroxybenzoic acid, 2,3-dihydroxybenzoic acid, 3,4-dihydroxybenzoic acid, 2,4-dihydroxybenzoic acid, vanillic acid, ethyl vanillin, isonicotinic acid, gallic acid, menthol (e.g., racemic menthol or (−)-menthol), paracetamol, aspirin, ibuprofen, naproxen, ketoprofen, flurbiprofen, glucose, serine, malic acid, acetamide, sulfacetamide, benzoic acid, 4-aminobenzoic acid, creatine, 2-hydroxyethanesulfonic acid, clofibric acid, taurine (tauric acid), iproniazid, L-histadine, L-arginine, L-asparagine, glutamine, L-cysteine, alanine, valine, isoleucine, leucine, morpholine, threonine, and N-methylglucamine.

Certain exemplary coformers that can provide a nicotine salt, co-crystal, or co-crystal salt are sugar-based acids (i.e., monosaccharides with a carboxyl group). Representative types of sugar acids include aldonic acids (e.g., glyceric acid, xylonic acid, gluconic acid, and ascorbic acid), ulosonic acids (e.g., neuraminic acid and ketodeoxyoctulosonic acid), uronic acids (e.g., glucuronic acid, galacturonic acid, and iduronic acid), and aldaric acids (e.g., tartaric acid, meso-galactaric acid/mucic acid, and D-glucaric acid/saccharic acid). In one preferred embodiment, the coformer or coformers used to provide a nicotine salt, co-crystal, or salt co-crystal according to the present disclosure is an aldaric acid, and in a particular preferred embodiment, the aldaric acid is mucic acid ((2S,3R,4S,5R)-2,3,4,5-tetrahydroxyhexanedioic acid, also referred to as galactaric or meso-galactaric acid).

Other exemplary coformers that can provide a nicotine co-crystal, salt, or co-crystal salt are polyfunctional aromatic acids. Polyfunctional aromatic acids often comprise a substituted or unsubstituted phenyl group as the aromatic component, but can alternatively comprise another aromatic moiety, e.g., pyridine, pyrazine, imidazole, pyrazole, oxazole, thiophene, naphthalene, anthracene, and phenanthrene. Substituents on the optionally substituted aromatic acids may be any type of substituent, including, but not limited to, halo (e.g., Cl, F, Br, and I); alkyl, halogenated alkyl (e.g., $CF_3$, 2-Br-ethyl, $CH_2F$, $CH_2Cl$, $CH_2CF_3$, or $CF_2CF_3$); alkenyl, hydroxyl; amino; carboxylate; carboxamido; alkylamino; arylamino; alkoxy; aryloxy; nitro; azido; cyano; thio; sulfonic acid: sulfate; phosphonic acid; phosphate; and phosphonate groups. Exemplary polyfunctional aromatic acids can be, for example:

substituted and unsubstituted aromatic dicarboxylic acids (e.g., 1,2-benzenedicarboxylic acid (phthalic acid), 1,3-benzenedicarboxylic acid (isophthalic acid), 1,4-benzenedicarboxylic acid (terephthalic acid), 2-iodo-1,3-benzenedicarboxylic acid, 2-hydroxy-1,4-benzenedicarboxylic acid, 2-nitro-1,4-benzenedicarboxylic acid, 3-fluoro-1,2-benzenedicarboxylic acid, 3-amino-1,2-benzenedicarboxylic acid, 3-nitro-1,2-benzenedicarboxylic acid, 4-bromo-1,3-benzenedicarboxylic acid, 4-hydroxy-1,3-benzenedicarboxylic acid, 4-amino-1,2-benzenedicarboxylic acid, 4-nitro-1,2-benzenedicarboxylic acid, 4-sulfo-1,2-benzenedicarboxylic acid, 4-amino-1,3-benzenedicarboxylic acid, 5-bromo-1,3-benzenedicarboxylic acid, 5-hydroxy-1,3-benzenedicarboxylic acid, 5-amino-1,3-benzenedicarboxylic acid, 5-nitro-1,3-benzenedicarboxylic acid, 5-ethynyl-1,3-benzenedicarboxylic acid, 5-cyano-1,3-benzenedicarboxylic acid, 5-nitro-1,3-benzenedicarboxylic acid, 2, 5-hydroxy-1,4-benzenedicarboxylic acid, and 2,3,5, 6-tetrafluoro-1,4-benzenedicarboxylic acid;

substituted and unsubstituted hydroxybenzoic acids (e.g., 2-hydroxybenzoic acid (salicylic acid), 3-hydroxybenzoic acid, 4-hydroxybenzoic acid, 2-methyl-4-hydroxybenzoic acid, 3-tert-butyl-4-hydroxybenzoic acid, 4-ethoxy-2-hydroxybenzoic acid, 3-chloro-5-hydroxybenzoic acid, 5-chloro-2-hydroxybenzoic acid, 3-bromo-4-hydroxybenzoic acid, 3-bromo-5-hydroxybenzoic acid, 4-bromo-2-hydroxybenzoic acid, S-bromo-2-hydroxybenzoic acid, 2-fluoro-5-hydroxybenzoic acid, 3-fluoro-4-hydroxybenzoic acid, 3-fluoro-2-hydroxybenzoic acid, 3-fluoro-5-hydroxybenzoic acid, 2-fluoro-6-hydroxybenzoic acid, 4-fluoro-3-hydroxybenzoic acid, 2-fluoro-4-hydroxybenzoic acid, 5-fluoro-2-hydroxybenzoic acid, 2-amino-3-hydroxybenzoic acid, 2-amino-5-hydroxybenzoic acid, 3-amino-2-hydroxybenzoic acid, 3-amino-4-hydroxybenzoic acid, 3-amino-5-hydroxybenzoic acid, 4-amino-2-hydroxybenzoic acid, 4-amino-3-hydroxybenzoic acid, 5-amino-2-hydroxybenzoic acid (mesalamine), 5-aminomethyl-2-hydroxybenzoic acid, 4-formyl-3-hydroxybenzoic acid, 3-formyl-4-hydroxybenzoic acid, 5-(acetylamino)-2-hydroxybenzoic acid), 4-nitro-2-hydroxybenzoic acid, 3,5-diethyl-4-hydroxybenzoic acid, 3,5-di-tert-butyl-4-hydroxybenzoic acid, 3,5-diisopropyl-2-hydroxybenzoic acid, 3,4-dimethoxy-4-hydroxybenzoic acid (syringic acid), 3,5-dichloro-2-hydroxybenzoic acid, 3,5-dichloro-4-hydroxybenzoic acid, 3,6-dichloro-2-hydroxybenzoic acid, 2,3-difluoro-4-hydroxybenzoic acid, 3,4-difluoro-2-hydroxybenzoic acid, 3,5-dibromo-2-hydroxybenzoic acid, 3,5-diodo-2-hydroxybenzoic acid, 4-amino-5-chloro-2-hydroxybenzoic acid, 3,5-dinitro-2-hydroxybenzoic acid, 2,4,6-tribromo-2-hydroxybenzoic acid, 2,3,5,6-tetrafluoro-4-hydroxybenzoic acid, and 2,3,4,5-tetrafluoro-6-hydroxybenzoic acid);

substituted and unsubstituted dihydroxybenzoic acids (e.g., 2,3-dihydroxybenzoic acid (pyrocatechuic acid/hypogallic acid), 2,4-dihydroxybenzoic acid (β-resorcylic acid), 2,5-dihydroxybenzoic acid (gentisic acid/hydroquinonecarboxylic acid), 2,6-dihydroxybenzoic acid (γ-resorcylic acid), 3,4-dihydroxybenzoic acid (protocatechuic acid), 3,5-dihydroxybenzoic acid (α-resorcylic acid), 4-hydroxy-3-methoxybenzoic acid (vanillic acid), 6-methyl-2,4-dihydroxybenzoic acid (orsellenic acid), 4-bromo-3,5-dihydroxybenzoic acid, 5-bromo-2,4-dihydroxybenzoic acid, 5-bromo-3,4-dihydroxybenzoic acid, 6-carboxymethyl-2,3-dihydroxybenzoic acid, 3,5-dibromo-2,4-dihydroxybenzoic acid, 3,5-dichloro-2,6-dihydroxybenzoic acid, and 5-amino-3-chloro-2,4-dihydroxybenzoic acid); and substituted and unsubstituted trihydroxybenzoic acids (e.g., 2,3,4-trihydroxybenzoic acid, 2,4,5-trihydroxybenzoic acid, 2,4,6-trihydroxybenzoic acid (phloroglucinol carboxylic acid), and 3,4,5-trihydroxybenzoic acid (gallic acid)).

substituted and unsubstituted aromatic tricarboxylic acids (e.g., 1,2,3-benzenetricarboxylic acid, 1,2,4-benzenetricarboxylic acid (trimellitic acid); and substituted and unsubstituted aromatic tetracarboxylic acids (e.g., 1,2,3,4-benzenetetracarboxylic acid (mellophanic acid) and 1,2,4,5-benzenetetracarboxylic acid (pyromellitic acid).

Other coformers useful in certain embodiments are flavor acids, including but not limited to, 3-hydroxy-2-oxopropionic acid; 2-oxobutyric acid (2-ketobutyric acid), 3-methyl-2-oxobutanoic acid; 3-methyl-2-oxopentanoic acid; 4-methyl-2-oxopentanoic acid; and 2-oxopentanedioic acid. Additional coformers can have higher molecular weights, such as 2-oxo-3-phenylpropionic acid; 5-oxooctanoic acid; and 5-oxodecanoic acid.

It is noted that certain coformers as described herein may contain one or more chiral centers, which may be either of the (R) or (S) configuration, or which may comprise a mixture thereof. As a result, various diastereomeric nicotine salts, co-crystals and salt co-crystals may be provided according to the present disclosure. The invention includes such diastereomers, either individually, or admixed in any proportions. Certain coformers as described herein may be geometric isomers, including but not limited to cis and trans isomers across a double bond. The invention includes all nicotine salts, co-crystals, and salt co-crystals prepared with such isomers, which may be provided in the form of pure isomers or in admixture with other isomers.

The method(s) by which the nicotine salts, co-crystals, and salt co-crystals described herein can be produced can vary. In some embodiments, no solvent (or a minimal amount of solvent) is used to prepare the nicotine salts, co-crystals, and salt co-crystals. Although in so-called "solventless" methods, a solvent is commonly not used, it is noted that one or more solvents may optionally be added (typically in a small amount) to the mixture to facilitate the formation of a nicotine salt, co-crystal, or salt co-crystal. In certain embodiments, the components (i.e., the nicotine and the one or more coformers) are combined in the absence of a solvent to form a slurry. Solids comprising nicotine salts, co-crystals, and/or salt co-crystals may be isolated therefrom via common methods (e.g., filtration). The slurry may be optionally heated such that the nicotine and one or more coformers interact in melted form to produce a salt, co-crystal, or salt co-crystal. In certain embodiments, physical methods are used to combine the components (i.e., the nicotine and the one or more coformers). For example, the nicotine and the coformer(s) can be ground together mechanically (e.g., using a mortar and pestle, ball mill, or vibratory mill).

In certain embodiments, a combination of nicotine and a coformer in a given solvent (or solvents) and evaporation of that solvent can provide the desired nicotine salt, co-crystal, or salt co-crystal. Typically, in such methods, the nicotine and coformer are provided in stoichiometric amounts (i.e., no excess nicotine or coformer is added). In such methods, selection of solvent is important, as the solvent (or solvents) in which the reaction is conducted can impact the intermolecular interactions. The evaporation of solvent can be done at a controlled rate (e.g., slowly) to encourage the preparation of a single nicotine salt, co-crystal, or salt co-crystal crystal for characterization. For example, the evaporation of solvent may be effected over the course of hours, days, weeks, or months.

In some embodiments, a combination of nicotine and a coformer in a given solvent (or solvents) and addition of a non-solvent can provide the desired nicotine salt, co-crystal, or salt co-crystal. Exemplary solvents and non-solvents that can be used for the preparation of nicotine salts, co-crystals, and salt co-crystals include, but are not limited to, water, alcohols (e.g., methanol, ethanol, n-butanol, isopropanol), ethers (e.g., diethyl ether, petroleum ether), ethyl acetate (EtOAc), acetone, tetrahydrofuran (THF), methylene chloride (DCM), chloroform, alkanes (e.g., pentane, hexane, heptane, octane, nonane, cyclohexane), benzene, toluene, 1,4-dioxane, and combinations thereof. In some embodiments, nicotine salts, co-crystals, and salt co-crystals can be prepared in supercritical fluids.

In other embodiments, the desired nicotine salt, co-crystal, or salt co-crystal can be prepared by freeze drying and subsequent maturation of a solution of nicotine and one or more coformers. For example, a solution may be prepared, frozen, and lyophilized to remove the solvent. A maturation solvent can then be added and the resulting solids can be obtained by common methods (e.g., filtration). Maturation solvents include, but are not limited, the types of solvents noted above.

The method of production of nicotine salts, co-crystals, and salt co-crystals as described herein may, in some embodiments, employ an excess of the coformer component. In such embodiments, it can advantageously be possible to purify the resulting salt, co-crystal, or salt co-crystal by removing excess coformer therefrom (i.e., that coformer which is not part of the structure of the salt, co-crystal, or salt co-crystal). Exemplary means for salt, co-crystal, or salt co-crystal formation that may, in certain embodiments, be applicable for the preparation of the nicotine salts, co-crystals, and salt co-crystals described herein are disclosed, for example, in U.S. Pat. No. 8,513,236 to Schultheiss et al.; U.S. Pat. No. 8,470,832 to George et al.; U.S. Pat. No. 8,466,280 to Grunenberg et al.; U.S. Pat. No. 8,415,507 to Schultheiss et al.; U.S. Pat. No. 8,350,085 to Childs; U.S. Pat. No. 8,241,371 to Hanna et al.; U.S. Pat. No. 8,212,079 to Childs; U.S. Pat. No. 8,173,625 to Brittain et al; U.S. Pat. No. 8,163,790 to Childs; U.S. Pat. No. 8,197,592 to Imamura et al.; U.S. Pat. No. 8,058,437 to Bauer et al.; U.S. Pat. No. 7,935,817 to Blazecka et al.; U.S. Pat. No. 7,927,613 to Almarsson et al.; U.S. Pat. No. 7,452,555 to Childs; U.S. Pat. No. 7,008,742 to Molaire; U.S. Pat. App. Pub. Nos. 2013/0203806 to Chorlton et al.; 2013/0072440 to Dokou et al.; 2013/0040970 to Cosgrove et al.; 2012/0258170 to Kruthiventi et al.; 2012/0028998 to Sansone et al.; 2012/0028930 to Kalofonos et al.; 2012/0022117 to Gruss et al.; 2011/0257340 to Childs; 2011/0251426 to Hanna et al.; 2011/0236478 to Dokou et al.; 2011/0152266 to Grunenberg et al.; 2010/0204204 to Zaworotko et al; 2008/0280858 to Hanna et al., 2007/0287194 to Childs et al.; 2003/0224006 to Zaworotko et al.; and 2002/0048610 to Cima et al., which are all incorporated herein by reference in their entireties. Other references that provide exemplary means for the formation of certain nicotine salts include M. Dezelic and B. Nikolin, "Nicotine Compounds with Aromatic Acids. Part II.," Glasnik Drustva Hemicara Technol. N. R. Bosne I Hercegovine, Sarajevo, 10 (1961) 55-62 and M. Dezelic and D. Tomic, "Nicotine Compounds with Aromatic Acids," Kerm. Vjestnik 17 (1943):39-57, which are incorporated herein by reference.

For the preparation of the nicotine salts, co-crystals, and salt-co-crystals disclosed herein, the product can, in some embodiments, be provided by combining an acid (e.g., orotic acid, fumaric acid, or pyroglutamic acid) and nicotine in the absence of solvent. In some embodiments, an excess of nicotine is added to the reaction mixture and, advantageously, excess nicotine is removed (e.g., by vacuum and/or by washing/filtration, such as with THF, heptane, and/or EtOAc). Although such slurry methods commonly employ no solvent, it is noted that, in some embodiments, some solvent can be added to facilitate the formation of a salt, co-crystal, or salt-co-crystal.

In some embodiments, a solvent is used to facilitate salt formation. For example, an acid can be dissolved in THF, nicotine can be added thereto, and the resulting mixture can be stirred/shaken to produce the salt, co-crystal, or salt-co-crystal. Although a single solvent can, in some embodiments, be sufficient to form the desired salt, co-crystal, or salt-co-crystal, in some embodiments, an anti-solvent is used to promote the formation of a solid material. The solvent can be removed (e.g., by evaporation) to provide the salt, co-crystal, or salt-co-crystal. In some embodiments, the solid is washed, e.g., with THF, heptane, and/or EtOAc. In some embodiments, mechanical grinding is used to promote the formation of the salt, co-crystal, or salt-co-crystal, as will be described further herein (see, e.g., the Examples).

Desirably, single crystal x-ray diffraction (SCXRD) can be used in some embodiments to determine the makeup of the solids (i.e., the nicotine salts, co-crystals, and salt co-crystals). However, suitable, x-ray quality crystals cannot always be readily produced. Therefore, a variety of other solid state spectroscopic techniques can be used including, but not limited to, x-ray powder diffraction (XRPD), Raman spectroscopy, FTIR spectroscopy, vibrational spectroscopy, polarized light microscopy (PLM), and solid state NMR. The nicotine salts, co-crystals, and salt co-crystals described herein may be further characterized, for example, using such techniques as $^{13}C$ NMR and $^1H$ NMR (in a suitable solvent, e.g., in $D_2O$ or DMSO-$d_6$) to evaluate the chemical structure, Gravimetric Vapor Sorption (GVS) to evaluate the hygroscopicity, thermogravimetric analysis (TGA) and differential scanning calorimetry (DSC) to evaluate the thermal properties, and/or chromatography (e.g., HPLC) in a suitable solvent to evaluate the purity. Products as described herein can be further analyzed via Karl Fischer Titration (KF) to determine the water content.

It is noted that, in certain cases, it is difficult to distinguish between co-crystals and salts. Typically, distinguishing a salt from a co-crystal requires evidence of proton transfer, which may not be straightforward to identify even with single crystal x-ray diffraction. In other terms, distinguishing a salt from a co-crystal generally requires evidence of ionic interactions, as opposed to merely non-ionic interactions. Accordingly, although the novel compositions described herein are described as salts, it is noted that in some embodiments, it may not be known whether a given product exists in salt, co-crystal, or salt co-crystal form or in some type of intermediate form (e.g., wherein the proton has not been transferred to a basic site, but may reside in space between the donor coformer and acceptor).

The nicotine salts, co-crystals, and salt co-crystals described herein can be incorporated into various products, including tobacco-containing products. The important characteristics of nicotine salts, co-crystals, and salt co-crystals for use in different types of products vary, as will be discussed in detail below.

The nicotine salts, co-crystals, and salt co-crystals provided herein can, in some embodiments, be used as compositions in the manufacture of smoking articles. For example, salts, co-crystals, and salt co-crystals prepared in accordance with the present invention can be mixed with casing materials and applied to tobacco as a casing ingredient or as a top dressing. Still further, salts, co-crystals, and salt co-crystals of the present disclosure can be incorporated into a cigarette filter (e.g., in the filter plug, plug wrap, or tipping paper) or incorporated into cigarette wrapping paper, preferably on the inside surface, during the cigarette manufacturing process. See, for example, the description and references related to tobacco isolates used in smoking articles set forth in US Pat. Pub. No. 2012/0192880 to Dube et al., which is incorporated by reference herein. Representative tobacco blends, non-tobacco components, and representative cigarettes manufactured therefrom are also set forth in the Dube et al. reference noted above.

Typically, the amount of nicotine salt, co-crystal, or salt co-crystal incorporated into a smoking article is that amount sufficient to provide the desired amount of free nicotine in the mainstream smoke produced therefrom. For example, in some embodiments, the smoking article may provide nicotine in an amount of about 0.1 mg to about 10 mg, about 0.5 mg to about 9 mg, or about 1 mg to about 8 mg. Accordingly, the amount of nicotine salt, co-crystal, or salt co-crystal incorporated into the smoking article can be, for example, that amount sufficient to produce these amounts of nicotine when the article is used.

Figure 43:
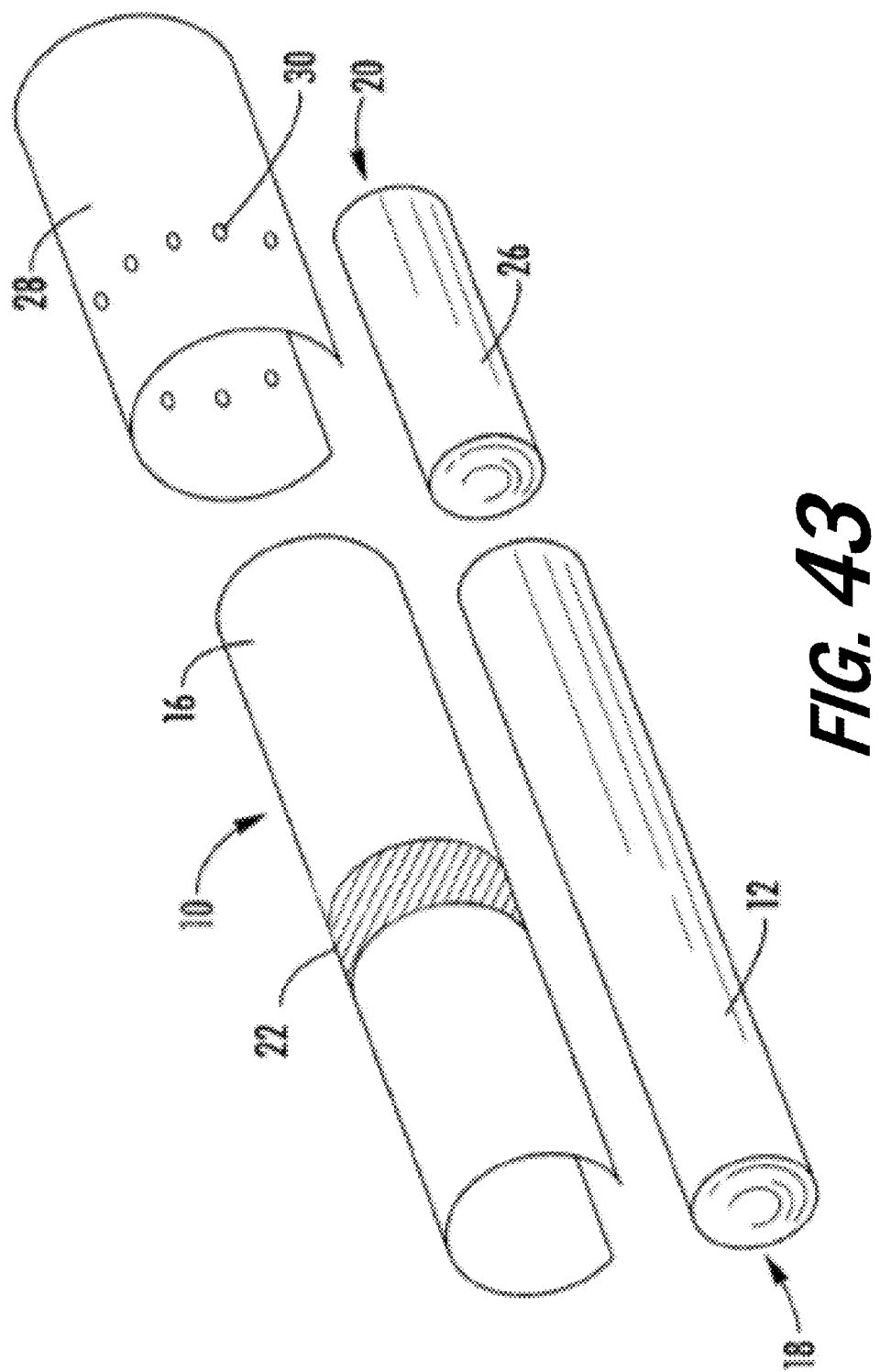
FIG. 43 is an exploded perspective view of a smoking article having the form of a cigarette, showing the smokable material, the wrapping material components, and the filter element of the cigarette.

Referring to FIG. 43, there is shown a smoking article 10 in the form of a cigarette and possessing certain representative components of a smoking article that can contain the formulation of the present invention. The cigarette 10 includes a generally cylindrical rod 12 of a charge or roll of smokable filler material (e.g., about 0.3 g to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the tipping material and plug wrap. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The salts of the invention can be incorporated within any of the components of a smoking article, including but not limited to, as a component of the tobacco charge, as a component of the wrapping paper (e.g., included within the paper or coated on the interior or exterior of the paper), as an adhesive, as a filter element component, and/or within a capsule located in any region of the smoking article.

The temperature at which nicotine, the coformer component (or components), and any degradation products thereof are released from a nicotine salt, co-crystal, or salt co-crystal can be a relevant consideration in the context of smoking articles. It is typically important that nicotine is released from the salt, co-crystal, or salt co-crystal (i.e., that the nicotine transfers to the mainstream smoke and is delivered to the user) at the burn temperature of the smoking article. It can also be important in some embodiments to ensure that certain undesirable coformers and/or degradation products thereof are not transferred to the mainstream smoke (and delivered to the user). The relevant temperature may vary slightly, depending upon the specific location(s) of the salt, co-crystal, or salt co-crystal within the smoking article. For example, in certain embodiments, the temperature at which a smoking article burns (and thus the temperature to which the salt is exposed) can be between at least about 100° C., at least about 200° C., or at least about 500° C., including between about 100° C. and about 500° C. in certain regions of a smoking article and between about 600° C. and about 900° C. in other regions of a smoking article. These considerations can impact selection of the salts, co-crystals, or salt co-crystals that are suitable for a particular application.

In other embodiments, the nicotine salts, co-crystals, and salt co-crystals disclosed herein can be incorporated within smokeless tobacco products. Representative smokeless tobacco compositions according to the present invention can have various types of formats and configurations, and as a result, the character, nature, behavior, consistency, shape, form, size and weight of the composition can vary. In some embodiments, the nicotine salts, co-crystals, and salt co-crystals disclosed herein can be incorporated into smokeless tobacco products, such as loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; or capsule-like materials possessing an outer shell and an inner region. The shape of a representative composition can be generally spherical, cylindrical (e.g., ranging from the general shape of a flattened disc to the general shape of a relatively long, slender stick), helical, obloid, square, rectangular, or the like; or the composition can have the form of a bead, granular powder, crystalline powder, capsule, film, strip, gel, or the like. The shape of the composition can resemble a wide variety of pill, tablet, lozenge, capsule, and caplet types of products. Various types of smokeless tobacco products are described or referenced in US Pat. Pub. Nos. 2013/0206150 to Duggins et al.; 2013/0074855 to Holton, Jr.; 2012/0118310 to Cantrell et al.; 2012/0138073 to Cantrell et al.; 2012/0138074 to Cantrell et al.; and 2012/0152265 to Dube et al., which are all incorporated herein by reference.

Figure 44:
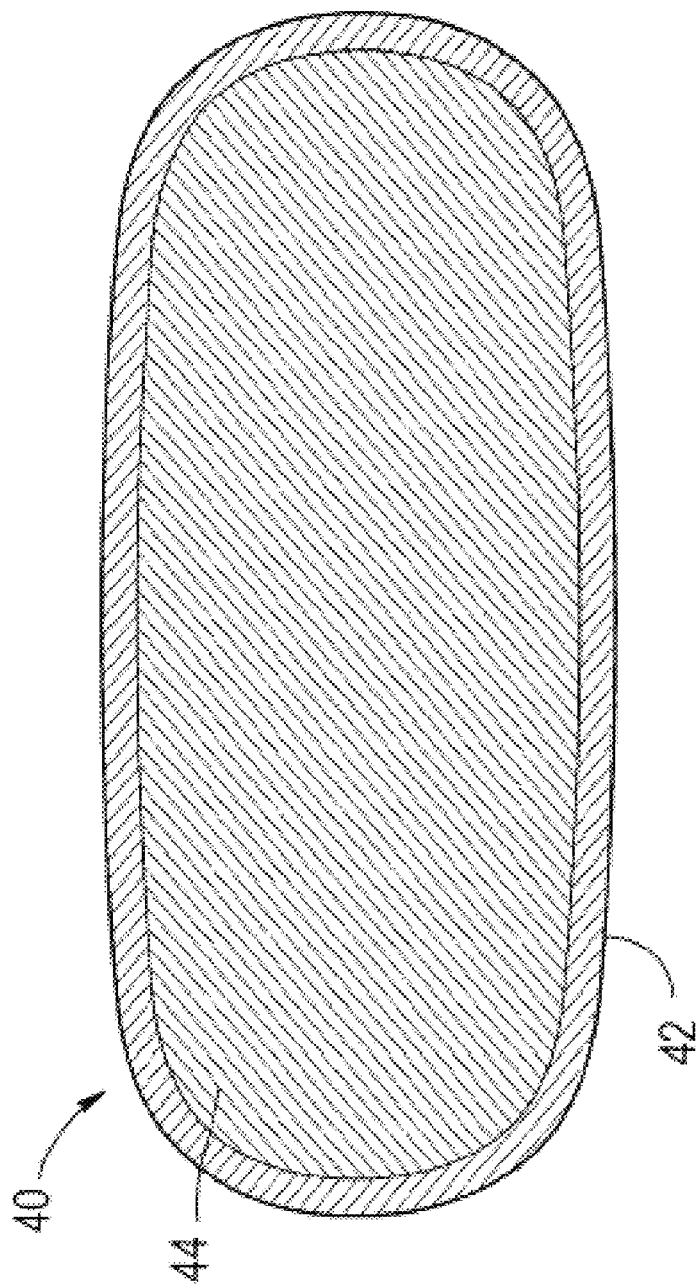
FIG. 44 is a cross-sectional view of a smokeless tobacco product embodiment, taken across the width of the product, showing an outer pouch filled with a smokeless tobacco composition of the invention.

Referring to FIG. 44, a representative snus type of tobacco product comprising one or more nicotine salts, co-crystals, or salt co-crystals according to the present disclosure is shown. In particular, FIG. 44 illustrates a smokeless tobacco product 40 having a water-permeable outer pouch 42 containing a smokeless tobacco composition 44. Any of the components of the tobacco product can comprise one or more nicotine salts, co-crystals, or salt co-crystals, according to the present disclosure (e.g., the interior or exterior of the pouch lining or a portion of the smokeless tobacco composition contained therein).

Other exemplary smokeless tobacco products into which the salts, co-crystals, and salt co-crystals described herein can be incorporated can have the form of a gum, lozenge, tablet, microtab, or other tablet-type product. See, for example, the types of nicotine-containing lozenges, lozenge formulations, lozenge formats and configurations, lozenge characteristics and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen; and U.S. Pat. No. 7,374,779; US Pat. Pub. Nos. 2013/0074855 and 2013/0078307 to Holton, Jr.; 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; and 2013/0312774 to Holton, Jr., which are all incorporated herein by reference.

One representative type of smokeless tobacco product comprising one or more of the nicotine salts, co-crystals, or salt co-crystals described herein is a lozenge, e.g., as substantially described in US Pat. App. Pub. Nos. 2013/0312774, 2013/0074856, and 2013/0074855, all to Holton, Jr., which are incorporated herein by reference. Such lozenges can comprise, in addition to one or more nicotine salts, co-crystals, or salt-co-crystals, a majority of one or more sugar alcohols (e.g., isomalt and maltitol syrup), e.g., in an amount of at least about 50% by weight, at least about 70% by weight, at least about 80% by weight, or at least about 90% by weight. Other ingredients of particular interest in such lozenge products include, but are not limited to, salts (e.g., NaCl), sweeteners (e.g., sucralose), and one or more flavorings.

The amount of nicotine salt, co-crystal, or salt co-crystal incorporated within a smokeless tobacco composition can vary and can be dependent, in part, on the specific type of smokeless tobacco composition. Clearly, the amount of a given nicotine salt, co-crystal, or salt co-crystal to be incorporated within a product will depend on the desired nicotine content of that product, and can be calculated based on the mass of the coformer and the stoichiometry of the salt, co-crystal, or salt co-crystal. Exemplary amounts include from about 0.1% by weight of the consumable material to about 10% by weight of the consumable or inhalable material. For example, for a lozenge, the amount of nicotine salt, co-crystal, or salt co-crystal is at least about 0.5%, generally at least about 1%, often at least about 1.5%, often at least about 2%, often at least about 2.5%, and frequently at least about 3% by weight of the product, e.g., about 0.5% to about 10%, including about 1% to about 5% by weight of the product. The amount of nicotine salt, co-crystal, or salt co-crystal can be determined based on the desired nicotine content in the lozenge.

Various other substances can be added to the smokeless tobacco compositions comprising the nicotine salts, co-crystals, or salt co-crystals of the present invention. For example, excipients such as fillers or carriers for active ingredients (e.g., calcium polycarbophil, microcrystalline cellulose, hydroxypropylcellulose, sodium carboxymethylcellulose, cornstarch, silicon dioxide, calcium carbonate, lactose, and starches including potato starch, maize starch, etc.), thickeners, film formers and binders (e.g., hydroxypropyl cellulose, hydroxypropyl methylcellulose, acacia, sodium alginate, gum arabic, lecithin, xanthan gum and gelatin), antiadherents (e.g., talc), glidants (e.g., colloidal silica), humectants (e.g., glycerin), preservatives and antioxidants (e.g., sodium benzoate and ascorbyl palmitate), surfactants (e.g., polysorbate 80), dyes or pigments (e.g., titanium dioxide or D&C Yellow No. 10), and lubricants or processing aids (e.g., calcium stearate or magnesium stearate) are added to the compositions in certain embodiments. Other exemplary types of ingredients include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethyl vanillin glucoside, mannose, galactose, lactose, and the like), artificial sweeteners (e.g., sucralose, saccharin, aspartame, acesulfame K, neotame and the like), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), effervescing materials such as certain acid/base combinations, oral care additives (e.g., thyme oil, eucalyptus oil, and zinc), preservatives (e.g., potassium sorbate, and the like), syrups (e.g., honey, high fructose corn syrup, and the like), and mixtures thereof. In certain embodiments, the smokeless tobacco composition can include lipid components that provide a meltable composition that melts (as opposed to merely dissolving) in the oral cavity, such as compositions set forth in US Pat. Pub. No. 2012/0037175 to Cantrell et al., which is incorporated by reference herein. Exemplary encapsulated additives that can be included within the smokeless tobacco products disclosed herein are described, for example, in WO 2010/132444 to Atchley, which has been previously incorporated by reference herein. See also, the smokeless tobacco ingredients set forth in US Pat. Pub. Nos. 2012/0055494 to Hunt et al. and 2012/0199145 to Byrd et al., which are incorporated by reference herein.

The manners and methods used to formulate and manufacture the smokeless tobacco product can vary. Ingredients, including the nicotine salts, co-crystals, or salt co-crystals described herein, can be combined and processed into the desired composition by techniques such as extrusion, compression, molding, spraying, and the like. It is noted that certain considerations noted above for electronic smoking articles are not relevant in the context of a smokeless tobacco product. For example, nicotine salts, co-crystals, or salt co-crystals that are useful in smokeless tobacco products need not transfer to aerosol form at a given temperature. In smokeless tobacco products, the main consideration is that the nicotine salt, co-crystal, or salt co-crystal contained therein can provide nicotine when the smokeless tobacco product is placed in the mouth of the user (i.e., at some point during residence of the smokeless tobacco product in the mouth of the user). Accordingly, certain nicotine salts, co-crystals, or salt co-crystals that are useful for one type of tobacco product may not be useful for others.

Figure 45:
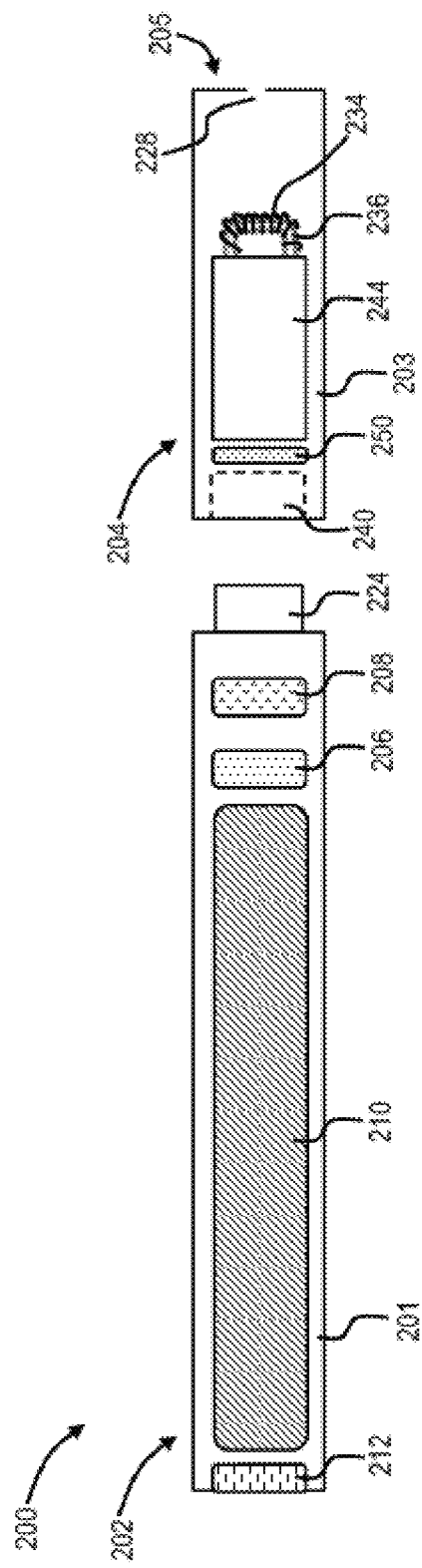
FIG. 45 is a cross-sectional view of an electronic smoking article, which can encompass a variety of combinations of components useful in forming an electronic aerosol delivery device.

In certain embodiments, the nicotine salts, co-crystals, and salt co-crystals provided according to the present disclosure are incorporated within electronic smoking articles. An exemplary embodiment of an electronic smoking article 200 incorporating a nicotine salt, co-crystal, or salt co-crystal according to the present disclosure is shown in FIG. 45. As illustrated therein, a control body 202 can be formed of a housing 201 that can include a control component 206, a flow sensor 208, a battery 210, and an LED 212. The electronic smoking article also may comprise a cartridge 204 that can be formed of a housing 203 enclosing a reservoir 244 that is in fluid communication with a transport element 236 adapted to wick or otherwise transport an aerosol precursor composition stored in the reservoir to a heater 234 (e.g., a resistive heating wire that may be coiled around at least a portion of the transport element). Exemplary reservoirs and transport elements are disclosed in US Pat. Pub. No. 2014/0261487 to Chapman et al, and exemplary heaters are disclosed in US Pat. Pub. No. 2014/0157583 to Ward et al., the disclosures of which are incorporated herein by reference in their entireties. An opening 228 may be present in the cartridge housing 203 at a mouthend 205 thereof to allow for egress of formed aerosol from the cartridge 204. Such components are representative of the components that may be present in a control body and/or cartridge and are not intended to limit the scope of components that are encompassed by the present disclosure.

The cartridge 204 may be adapted to engage the control body 202 through a press-fit engagement between the control body projection 224 and the cartridge receptacle 240. Such engagement can facilitate a stable connection between the control body 202 and the cartridge 204 as well as establish an electrical connection between the battery 210 and control component 206 in the control body and the heater 234 in the cartridge. Other types of connections (e.g., a screw thread connection) also are encompassed. The electronic smoking article 200 may be adapted for air intake, which may be provided in a coupler as described, for example, in US Pat. Pub. No. 2014/0261408 to DePiano et al., the disclosure of which is incorporated herein by reference in its entirety. The cartridge 204 also may include one or more electronic components 250, which may include an IC, a memory component, a sensor, or the like. The electronic component 250 may be adapted to communicate with the control component 206 so as to provide an input. See, for example, US Pat. Pub. Nos. 2014/0096781 to Sears et al. and 2014/0096782 to Ampolini et al., the disclosures of which are incorporated herein by reference in their entirety.

The electronic smoking article can encompass a variety of combinations of components useful in forming an electronic aerosol delivery device. Reference is made for example to the following: a reservoir and heater system for controllable delivery of multiple aerosolizable materials disclosed in US Pat. Pub. No. 2014/0000638 to Sebastian et al.; microheaters as disclosed in US Pat. Pub. No. 2014/0060554 to Collett et al.; carbon-based cartridges and components thereof, as disclosed US Pat. Pub. No. 2013/0255702 to Griffith, Jr. et al.; single-use cartridges as disclosed in US Pat. Pub. No. 2014/0060555 to Chang et al.; aerosol precursor transport elements, such as disclosed in US Pat. Pub. No. 2014/0209105 to Sears et al.; charging components, such as an adaptor disclosed in US Pat. Pub. No. 2014/0261495 to Novak, III et al.; vibration components, such as disclosed in US Pat. Pub. No. 2015/0020825 to Galloway et al.; and batteries, such as disclosed in U.S. Pat. Pub. No. 2010/0028766 to Peckerar et al.

Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLUR™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

In certain embodiments, the aerosol precursor comprises a nicotine salt, co-crystal, or salt co-crystal as disclosed herein. In one embodiment, the aerosol precursor composition can comprise, for example, a polyhydric alcohol (e.g., glycerin, propylene glycol, or a combination thereof), water, a nicotine salt, co-crystal, or salt co-crystal as described herein, and a flavorant (e.g., menthol). Exemplary flavoring agents include vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Flavoring agents also can include acidic or basic characteristics (e.g., organic acids, such as levulinic acid, succinic acid, and pyruvic acid). Representative types of aerosol precursor compositions are set forth in U.S. Pat. No. 4,793,365 to Sensabaugh, Jr. et al.; U.S. Pat. No. 5,101,839 to Jakob et al.; U.S. Pat. Pub. No. 2013/0008457 to Zheng et al.; and Chemical and Biological Studies on New Cigarette Prototypes that Heat Instead of Burn Tobacco, R. J. Reynolds Tobacco Company Monograph (1988). The disclosures of all of the foregoing documents are incorporated herein by reference in their entireties.

One or more acid components can be included within the aerosol precursor, e.g., to modify the sensory characteristics of the aerosol precursor and the aerosol produced therefrom. Organic acids particularly may be incorporated into the aerosol precursor to affect the flavor, sensation, and/or organoleptic properties of nicotine. Such organic acids can be included in the aerosol precursor with nicotine in varying amounts ranging from greater than equimolar to less than equimolar (based on total organic acid content) with the nicotine. A range of organic acids can be used in accordance with such embodiments, e.g., as set forth in Perfetti, *Beitrage Tabakforschung Int.*, 12, 43-54 (1983), which is incorporated herein by reference. Certain exemplary organic acids that may be useful include, but are not limited to, such acids as tartaric acid, ascorbic acid, fumaric acid, citric acid, malic acid, lactic acid, aspartic acid, salicylic acid, 4-amino salicylic acid, N-acetyl-4-aminosalicylic acid, p-toluenesulfonic acid, succinic acid, pyruvic acid, formic acid, acetic acid, propionic acid, isobutyric acid, butyric acid, alpha-methylbutyric acid, 2-ketobutyric acid, isovaleric acid, beta-methylvaleric acid, caproic acid, 2-furoic acid, phenylacetic acid, heptanoic acid, octanoic acid, nonanoic acid, oxalic acid, malonic acid, glycolic acid, levulinic acid, 4-aminobenzoic acid, 4-acetamidobenzoic acid, 3-hydroxybenzoic acid, 2,5-dihydroxybenzoic acid, 2,3-dihydroxybenzoic acid, 2,4-dihydroxybenzoic acid, 3,4-dihydroxybenzoic acid, vanillic acid, mucic acid, cyclamic acid, benzenesulfonic acid, 2-hydroxyethanesulfonic acid, 1-hydroxy-2-naphthoic acid, ketoglutaric acid, D-glucuronic acid, maleic acid, glutamic acid, L-pyroglutamic acid, nicotinic acid, isonicotinic acid, gallic acid, phthalic acid, mandelic acid, hippuric acid, cinnamic acid, adipic acid, orotic acid, sorbic acid, clofibric acid, tauric acid, and combinations of two or more such organic acids. By using a nicotine salt, co-crystal, or salt co-crystal in place of nicotine, it may be possible in certain embodiments to reduce and or eliminate the amount of acid advantageously incorporated within the aerosol precursor.

The amount of aerosol precursor composition that is used within the smoking article is such that the article exhibits acceptable sensory and organoleptic properties, and desirable performance characteristics. For example, it is highly preferred that sufficient aerosol precursor composition components, such as glycerin and/or propylene glycol, be employed in order to provide for the generation of a visible mainstream aerosol that in many regards resembles the appearance of tobacco smoke. Typically, the amount of aerosol-generating material incorporated into the smoking article is in the range of about 1.5 g or less, about 1 g or less, or about 0.5 g or less. The amount of aerosol precursor composition can be dependent upon factors such as the number of puffs desired per cartridge used with the smoking article. It is desirable for the aerosol-generating composition not to introduce significant degrees of unacceptable off-taste, filmy mouth-feel, or an overall sensory experience that is significantly different from that of a traditional type of cigarette that generates mainstream smoke by burning tobacco cut filler. The selection of the particular aerosol-generating material and reservoir material, the amounts of those components used, and the types of tobacco material used, can be altered in order to control the overall chemical composition of the mainstream aerosol produced by the smoking article.

Typically, the amount of nicotine incorporated into an aerosol precursor of an electronic smoking article is that amount sufficient to provide the desired amount of free nicotine in the aerosol produced therefrom. For example, the article may provide nicotine in an amount of about 0.01 mg to about 0.5 mg, about 0.05 mg to about 1 mg, about 0.08 mg to about 0.5 mg, about 0.1 mg to about 0.3 mg, or about 0.15 mg to about 0.25 mg per puff on the article. Accordingly, the amount of nicotine salt, co-crystal, or salt co-crystal incorporated into the aerosol precursor can be, for example, that amount sufficient to produce these amounts of nicotine when the article is used.

When the nicotine salts, co-crystals, or salt co-crystals described herein are used in electronic smoking articles, the temperature at which nicotine is released into aerosol form from the salt, co-crystal, or salt co-crystal is an important consideration. It is typically important that nicotine is released from the salt, co-crystal, or salt co-crystal (i.e., that the nicotine transfers to aerosol form) at the operating temperature of the electronic smoking articles. Although not intended to be limiting, exemplary operating temperatures of electronic smoking articles are within the range of about 100° C. to about 500° C. (e.g., about 120° C. to about 300° C.). Accordingly, selection of an appropriate nicotine salt, co-crystal, or salt co-crystal for incorporation into such products can depend, in part, on the characteristics of the bond between the nicotine and the coformer and the volatility of the salt, co-crystal, or salt co-crystal. For example, nicotine citrate may not be a good salt for an electronic smoking article because it is not sufficiently volatile.

Furthermore, in some embodiments, the temperature at which the coformer component (or components) is released from a nicotine salt, co-crystal, or salt co-crystal can be a relevant consideration. As it may not be advantageous for certain coformers (e.g., certain acids) to be present in the aerosol (and delivered to the user), it can be important to consider the temperature at which not only the nicotine, but also the coformer of the nicotine salt, co-crystal, or salt co-crystal transfers to aerosol form. In other embodiments, the coformer(s) of a given nicotine salt, co-crystal, or salt co-crystal may be desirably contained in the aerosol and desirably delivered to the user. In such cases, it may be advantageous to ensure that such coformer(s) are sufficiently volatile at the temperature of use of the electronic smoking article. Additionally, any degradation products produced via heating nicotine salts, co-crystals, or salt co-crystals to the relevant temperature (i.e., the typical operation temperature of an electronic smoking article) should also be evaluated and taken into consideration during product preparation and selection for a particular application. In particular, in certain embodiments, acid degradation products produced via heating nicotine salts, co-crystals, or salt co-crystals to the relevant temperature should be evaluated and taken into consideration.

Accordingly, in certain embodiments, following preparation of the nicotine salts, co-crystals, or salt co-crystals described herein, they are analyzed to evaluate whether the nicotine and/or coformer and/or degradation products thereof transfer from the aerosol precursor to the aerosol. Such analysis can be conducted, for example, by high performance liquid chromatography and/or gas chromatography of the condensate collected from the aerosol. Both the presence and amount of nicotine and/or coformer and/or degradation products thereof is evaluated to determine whether a given salt, co-crystal, or salt co-crystal is a good candidate for incorporation within an electronic smoking article.

In still further embodiments, nicotine salts, co-crystals, and/or salt co-crystals disclosed herein may be incorporated within pharmaceutical products. For example, a nicotine salt, co-crystal, or salt co-crystal can be used as a replacement for, or in addition to, the nicotine in nicotine-containing pharmaceutical products. Such products can be used for treatment of a wide variety of conditions, diseases, and disorders responsive to stimulation of one or more types of nicotinic acetylcholinergic receptors (nAChRs). The products can be used to treat those types of conditions, diseases, and disorders that have been reported to be treatable through the use or administration of nicotine as an agonist of nAChRs. As such, the products can be used to treat various CNS conditions, diseases, and disorders, and the compositions also can be used as smoking cessation aids (i.e., as components of NRT). The combined amount of nicotine present (including nicotine present as the salt, co-crystal, and/or salt co-crystal form and, optionally, any one or more other forms of nicotine) is preferably that amount effective to treat some symptoms of, or prevent occurrence of the symptoms of, a condition, disease, or disorder from which the subject or patient suffers. Exemplary conditions, diseases or disorders that can be treated include cognitive disorders such as Alzheimer's disease and attention deficit disorder, schizophrenia, Parkinson's disease, Tourette's syndrome, ulcerative colitis, dry eye disease, hypertension, depression, overactive bladder, obesity, seven year itch/scabies, and hemorrhoids. Such products may also find use as a treatment to reduce stress or pain and/or as a smoking cessation aid.

The shape of the pharmaceutical products can resemble a wide variety of pill, tablet, lozenge, capsule, caplet, pouch and gum types of products that traditionally have been employed for the administration of pharmaceutical types of products. The general nature of a representative composition can be soft or hard to the feel, or of intermediate softness or hardness; and as such, the composition can be considered to be malleable, flexible, chewy, resilient, brittle, or the like. Pharmaceutical products containing nicotine salts, co-crystals, or salt co-crystals as provided herein are not limited to oral products, and such compositions as creams (including salves, ointments, and pastes), liquids (e.g., sprays or enemas), and the like are also encompassed by the present invention as well. In addition, the nicotine salts, co-crystals, and salt co-crystals disclosed herein can also be incorporated within various devices for delivery, such as inhalers (e.g., metered dose inhalers, dry powder inhalers, and nebulizers). Pharmaceutical products according to the present invention can contain, in addition to a nicotine salt, co-crystal, and/or salt co-crystal as described herein, one or more pharmaceutically acceptable components, e.g., excipients (e.g., salts, sweeteners, fillers, flavorants, antiadherents, glidants, preservatives and antioxidants, surfactants, dyes or pigments, lubricants, and/or processing aids).

The application as written focuses on the incorporation of novel nicotine salts, co-crystals, and salt co-crystals. However, it is noted that, in some embodiments, known nicotine salts can be employed in compositions disclosed herein to provide novel compositions and/or novel products incorporating such compositions. For example, although not intended to be limiting, known salts such as nicotine L-malate (CAS RN 253180-13-1), nicotine 4-acetamidobenzoic acid salt (CAS RN 110441-65-1), nicotine 3-hydroxybenzoic acid (CAS RN 1644394-41-1, disclosed, for example, in Int. App. Pub. No. WO2015/006652), nicotine 2,5-dihydroxybenzoic acid (CAS RN 6012-21-1), nicotine 4-aminosalicylic acid salt (1-hydroxy-4-amino benzoic acid salt) (CAS RN 20334-41-2), nicotine salicylic acid salt (2-hydroxybenzoic acid salt) (CAS RN 29790-52-1), nicotine phthalic acid salt (1,2-benzene dicarboxylic acid salt) (CAS RN 88660-55-3), nicotine N-acetyl-4-aminosalicylic acid salt (N-acetyl-2-hydroxy-4-aminobenzoic acid salt) (CAS RN 900789-26-6), and/or nicotine di-L-(+)-tartrate dihydrate (CAS RN 6019-06-3) can be used in the compositions and products disclosed herein.

It is further noted that, although the application as written focuses on the formation of nicotine salts, co-crystals, and salt co-crystals and on the incorporation of such formed nicotine salts, co-crystals, and salt co-crystals into various products, it may be possible, in some embodiments, to form such nicotine salts, co-crystals, and salt co-crystals in situ. For example, nicotine can be combined with one or more coformers as broadly described herein, and optionally, other components (e.g., those types of components typically contained in the product to be formed), and a nicotine salt, co-crystal, or salt co-crystal is formed in situ. In other words, although it is often advantageous for reasons disclosed herein, isolation and/or purification of the nicotine salt, co-crystal, or salt co-crystal is not required in all embodiments prior to introduction into a product.

For example, in one embodiment, an aerosol precursor of an electronic smoking article can be prepared by mixing a nicotine salt, co-crystal, or salt co-crystal with desired aerosol precursor components (e.g., carriers and flavorants) or can be prepared by mixing nicotine, a coformer (e.g., an acid), and desired aerosol precursor components. See, for example, the methods of incorporating certain salts into aerosol devices in Int. App. Pub. No. WO2014/182736 to Ploom, Inc., which is incorporated herein by reference.

Aspects of the present invention are more fully illustrated by the following examples, which are set forth to illustrate certain aspects of the present invention and are not to be construed as limiting thereof.

EXPERIMENTAL

General
X-Ray Powder Diffraction (XRPD)

Some X-Ray Powder Diffraction patterns are collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate). The beam divergence, i.e., the effective size of the X-ray beam on the sample, is approximately 4 mm. A θ-θ continuous scan mode is employed with a sample-detector distance of 20 cm which gives an effective 2θ range of 3.2°-29.7°. Typically the sample is exposed to the X-ray beam for 120 seconds. The software used for data collection is GADDS for XP/2000 4.1.43 and the data are analyzed and presented using Diffrac Plus EVA v13.0.0.2 or v15.0.0.0.

Samples run under ambient conditions are prepared as flat plate specimens of powder, without grinding. Approximately 1-2 mg of the sample is lightly pressed on a glass slide to obtain a flat surface. Samples run under non-ambient conditions are mounted on a silicon wafer with heat-conducting compound. The sample is heated to the appropriate temperature at 20° C./min and subsequently held isothermally for 1 minute before data collection was initiated.

Some X-Ray Powder Diffraction patterns are collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analyzed and presented using Diffrac Plus EVA v15.0.0.0.

Samples are run under ambient conditions as flat plate specimens using powder as received. The sample was gently packed into a cavity cut into polished, zero-background (510) silicon wafer. The sample was rotated in its own plane during analysis. The details of the data collection are: Angular range: 2 to 42° 2θ; Step size: 0.05*2θ; and collection time: 0.5 s/step.

$^1$H Nuclear Magnetic Resonance ($^1$H NMR)

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Broker loaded experiments. For non-routine spectroscopy, data were acquired through the use of Topspin alone. Samples were prepared in DMSO-$d_6$, unless otherwise stated. Off-line analysis was carried out using ACD Spectrus Processor 2012.

Fourier Transform-Infra-Red (FTIR)

Data were collected on a Perkin-Elmer Spectrum One fitted with a universal Attenuated Total Reflectance (ATR) sampling accessory. The data were collected and analyzed using Spectrum v10.0.1 software.

Differential Scanning Calorimetry (DSC)

DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminum pan, was heated at 10° C./min from 25° C. to 300° C. A purge of dry nitrogen at 50 ml/min was maintained over the sample. The instrument control software was Advantage for Q Series v2.8.0.394 and Thermal Advantage v5.5.3 and the data were analyzed using Universal Analysis v4.5A.

Thermo-Gravimetric Analysis (TGA)

TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminum DSC pan and heated at 10° C./min from ambient temperature to 350° C. A nitrogen purge at 60 ml/min was maintained over the sample. The instrument control software was Advantage for Q Series v2.5.0.256 and Thermal Advantage v5.5.3 and the data were analyzed using Universal Analysis v4.5A.

Polarized Light Microscopy (PLM)

Samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarized light, coupled to a) false-color filter.

Scanning Electron Microscopy (SEM)

Data were collected on a Phenom Pro Scanning Electron Microscope. A small quantity of sample was mounted onto an aluminum stub using conducting double-sided adhesive tape. A thin layer of gold was applied using a sputter coater (20 mA, 120 s).

Water Determination by Karl Fischer Titration (KF)

The water content of each sample was measured on a Metrohm 874 Oven Sample Processor at 140° C. or 190° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. Data collection and analysis using Tiamo v2.2.

Gravimetric Vapor Sorption (GVS)

Sorption isotherms were obtained using a SMS DVS Intrinsic moisture sorption analyzer, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 ml/min The relative humidity was measured by a calibrated Rotronic probe (dynamic range of 1.0-100% RH), located near the sample. The weight change, (mass relaxation) of the sample as a function of % RH was constantly monitored by the microbalance (accuracy±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was carried out using Microsoft Excel using DVS Analysis Suite v6.2 (or 6.1 or 6.0).

TABLE 1

Method for SMS DVS Intrinsic experiments

| Parameter | Value |
| --- | --- |
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml/min) | 200 |
| Temperature (° C.) | 25 |
| Stability (° C./min) | 0.2 |
| Sorption Time (hours) | 6 hour time out |

The sample is recovered after completion of the isotherm and re-analyzed by XRPD.

Example 1

Salts of Nicotine with Orotic Acid

A screening experiment is first conducted to evaluate a solvent free method for the formation of a salt of orotic acid. Orotic acid (50 mg+/−1 mg) is weighed into a glass vial and (S)-Nicotine (2 molar equivalents) is dispensed into each vial, vials are stirred at 50° C. for 1 hour, cooled to 5° C. at 0.1° C./min, and stirred at 5° C. overnight. Upon the addition of nicotine, the material was observed to be a suspension and the material remained a suspension after 1 hour. After cooling, the material was observed to be a pink suspension. After stirring at 5° C. overnight, solids are sampled and characterized by XRPD. The XRPD analysis results indicate that the solid present in the vial includes a new crystalline phase form, indicative of the formation of an orotic acid salt.

Various screening experiments are next conducted to evaluate alternative (solvent-based) means for the preparation of orotic salts of nicotine, as the slurrying method in neat nicotine was found to be challenging for repetition on a larger scale.

Experiments are conducted to evaluate the preparation of an orotic salt via slow evaporation from various solvents. Orotic acid (50 mg+/−1 mg) is weighed into glass vials and the relevant solvent is added at 3, 10, and 20 volumes at 50° C. to try to form solutions of the orotic acid. Nicotine (1 molar equivalent) is added. The resulting mixtures are stirred at 50° C. for 1 hour, cooled to 5° C. at 0.1° C. per minute, and then stirred at 5° C. overnight. Solids are sampled and analyzed by XPRD; solids exhibiting new XRPD patterns are filtered and dried under vacuum overnight. See FIGS. 1 and 2.

Samples exhibiting XRPD patterns consistent with the acid/coformer and any samples in the form of oils/gums are matured (shaken in 8 hour cycles at 50° C./RT). Solutions are left to evaporate slowly at ambient conditions via loosened lids. Any resulting solids are sampled and analyzed by XRPD (see FIG. 3), and $^1$H NMR (see FIG. 4) with oils/gums being matured as above. Samples that remain solutions after anti-solvent addition are left to evaporate under ambient conditions. A summary of these solvent-mediated screens and the observations associated with each screen are provided in Table 2.

TABLE 2

Solvent-mediated screen for formation of salt from nicotine and orotic acid

| Solvent | Anti-solvent | Observations |
| --- | --- | --- |
| THF | n/a | Undissolved acid after addition of nicotine |
| | | Suspension after cooling to 5° C., XPRD indicates crystalline new pattern ("Pattern 1") |
| | | Material filtered to give solid |
| Water | n/a | Solution after addition of nicotine |
| | | Solution after 1 h at 50° C. |
| | | Solution after cooling to 5° C. |
| | | Solution after initial evaporating step |
| | | Gummy solid formed after further evaporation, crystalline new pattern by XRPD. |
| Ethanol | Methyl tert-butyl ether (TBME) | Suspension after addition of nicotine |
| | | Suspension after 1 h at 50° C. |
| | | Suspension after cooling to 5° C., XPRD at this stage indicates new pattern of weakly crystalline material. |
| | | Suspension after maturing for 1 week, XRPD indicates the material is crystalline ("Pattern 1") |
| MEK | n-heptane | Suspension after addition of nicotine |
| | | Suspension after 1 h at 50° C. |
| | | Suspension after cooling to 5° C., XPRD indicates a new pattern ("Pattern 1" and "Pattern 2" mixture). |
| | | Material filtered to give solid |
| IPA/water (80/20 volume) | n/a | Almost dissolved on addition of nicotine, |
| | | Solution after 1 h at 50° C. |
| | | Solution after cooling to 5° C. |
| | | Solution after evaporating |
| | | After further evaporation, XRPD is taken, indicating new pattern ("Pattern 2"). |
| Ethyl acetate | n-heptane | Undissolved acid after addition of nicotine |
| | | Suspension after 1 h at 50° C., |
| | | Suspension after cooling to 5° C., XPRD indicates crystalline new pattern ("Pattern 2") |
| | | Material filtered to give solid |

A further experiment is conducted to evaluate the preparation of an orotic salt via grinding. Orotic acid (50 mg+/−1 mg) is weighed into a glass vial and nicotine (1 molar equivalent) is added, giving a slurry. Two ball bearings (3 mm, stainless steel) are added to the resulting mixture and the sample is ground for 2 hours at 650 rpm in a Fritsch Pulverisette mill, giving a white solid. The material is analyzed by XPRD, indicating a crystalline pattern ("Pattern 2"). The solid is isolated from the grinding vial and triturated with n-heptane to remove excess nicotine.

In all, two different XRPD patterns were observed for the orotic acid salts (arbitrarily referred to herein as "Pattern 1" and "Pattern 2," depending on the method of preparation, as summarized below in Table 3. Table 3 further provides additional characterization data for the orotic acid salts.

TABLE 3

Data correlated to method of preparation of orotic acid salt

| Method of salt preparation | XRPD Pattern of solid | $^1$H NMR | TGA | DSC | Result |
|---|---|---|---|---|---|
| Formation in THF | Pattern 1 | Peak shifts, ratio nicotine:orotic acid 1:2.0, trace THF | 0.8 wt. % loss 25-160° C. 334 wt. % loss 180-280° C. See FIG. 5 | Broad endotherm onset 120° C. Broad endotherm onset 138° C. Sharp endotherm onset 240° C. See FIG. 5 | Stable bis salt |
| Formation in ethanol | Pattern 1 | Peak shifts, ratio nicotine:orotic acid 1:1.9, trace EtOH | 0.6 wt. % loss 25-180° C. 34.3 wt. % loss 180-280° C. See FIG. 6 | Broad endotherm onset 92° C. Broad endotherm onset 127° C. Broad endotherm onset 190° C. Sharp endotherm onset 239° C. See FIG. 6 | Stable bis salt |
| Neat nicotine | Pattern 2 | Peak shifts, ratio nicotine:orotic acid 1:1.3 | 1.7 wt. % loss 25-125° C. 19.2 wt. % loss 125-230° C. 26.7 wt. % loss 230-280° C. See FIG. 7 | Large broad endotherm onset 97° C. See FIG. 7 | Stable mono salt |
| Formation in water | Pattern 2 | Peak shifts, ratio nicotine:orotic acid 1:1.0 | 1.8 wt. % loss 25-130° C. 22.4 wt. % loss 130-240° C. 42.4 wt. % loss 240-305° C. See FIG. 8 | Large broad endotherm onset 106° C. See FIG. 8 | Stable mono salt |
| Grinding | Pattern 2 | Peak shifts, ratio nicotine:orotic acid 1:1.1 | 1.8 wt. % loss 25-125° C. 22.6 wt. % loss 125-210° C. 27.1 wt. % loss 210-290° C. See FIG. 9 | Large endotherm onset 97° C. Broad endotherm onset 157° C. See FIG. 9 | Stable mono salt |
| Formation in IPA | Pattern 2 | Peak shifts, ratio nicotine:orotic acid 1:0.9, trace IPA | 1.9 wt. % loss 25-125° C. 65.2 wt. % loss 125-300° C. See FIG. 10 | Large broad endotherm onset 106° C. See FIG. 10 | Stable mono salt |
| Formation in ethyl acetate | Pattern 2 | Peak shifts, ratio nicotine:orotic acid 1:1.2, trace EtOAc | 2.5 wt. % loss 25-125° C. 19.1 wt. % loss 125-200° C. 52.3 wt. % loss 200-325° C. See FIG. 11 | Large endotherm onset 105° C. Broad endotherm onset 138° C. Broad endotherm onset 167° C. See FIG. 11 | Stable mono salt |

TABLE 3-continued

Data correlated to method of preparation of orotic acid salt

| Method of salt preparation | XRPD Pattern of solid | 1H NMR | TGA | DSC | Result |
|---|---|---|---|---|---|
| Formation in MEK | Pattern 1 and 2 | Peak shifts, ratio nicotine:orotic acid 1:1.3, trace MEK | 16.8 wt. % loss 25-180° C. 30.6 wt. % loss 180-280° C. See FIG. 12 | Large endotherm onset 98° C. Broad endotherm onset 126° C. See FIG. 12 | Stable mono salt |

The orotate salts are prepared on a larger scale. A salt having Nicotine Orotate XRPD Pattern 1 ("Orotate Pattern 1") is prepared by suspending orotic acid (9.6 g, 0.062 moles) in THF (20 vols, 190 ml) and warming the mixture to 50° C. The resulting white suspension is left to stir for ca. 30 minutes. After this time, 0.5 equivalents of nicotine (5 ml, 0.031 moles) is added and the sample is stirred at 50° C. for 1 hour. The sample is stirred at 50° C. overnight and then cooled to 5° C. at 0.2° C./min and stirred at 5° C. for ~1 hour. A sample is analyzed by XRPD and was found to be consistent with Orotate Pattern 1. The sample is filtered through a glass frit, washed with THF, sucked dry, and then further dried under vacuum for 3 days at ambient temperature to give a fine white powder, 12.47 g=85.3 wt. % yield ("Salt A" in Table 4, below).

A salt having Nicotine Orotate XRPD Pattern 2 ("Orotate Pattern 2") is prepared by suspending orotic acid (4.8 g, 0.031 moles) in EtOAc (20 vols, 100 ml) and warming the mixture to 50° C. The resulting white suspension is left to stir for ca, 30 minutes. Nicotine, 1 equivalent (5 ml, 0.031 moles), is added and the sample is stirred at 50° C. for 1 hour. The sample is cooled to 5° C., at 0.1° C./min and stirred at 5° C. overnight. A sample is analyzed by XRPD and found to be mainly consistent with Orotate Pattern 2, although some material exhibiting Pattern 1 was present. See FIG. 23. An additional 10 ml (2 equivalents) nicotine is added to push the equilibrium towards the mono-salt, and the sample is left to stir at 5° C. for 3 days. After this time, the sample is analyzed by XRPD and found to be consistent with Pattern 2. The sample is filtered through a glass frit, washed with EtOAc, sucked dry, and then further dried under vacuum overnight at ambient temperature to give a fine white powder, 8.43 g=86.0 wt. % yield ("Salt B" in Table 4, below).

The resulting solids are analyzed by various techniques, as summarized in Table 4, below.

TABLE 4

Characterization Summary of Scaled-up Salts

| | Salt A (prepared in THF) | Salt B (prepared in EtOAc) |
|---|---|---|
| Appearance | Fine white powder | Fine white powder |
| Yield (dry) | 85.3 wt. % | 86.0 wt. % |
| XRPD damp | Consistent with Orotate Pattern 1 (see FIG. 15) | Consistent with Orotate Pattern 2 (see FIG. 23) |
| XRPD dry | Orotate Pattern 1 (see FIGS. 15 and 16) | Orotate Pattern 2 (see FIGS. 23 and 24) |
| 1H NMR | Peak shifts, trace THF, 2.0 equiv. acid (see FIG. 17) | Peak shifts, trace EtOAc, 1.0 equiv.. acid (see FIG. 25) |
| Karl Fischer | n/a | 2.7 wt. % water (0.5 mol. equiv.) |
| Optical microscopy | Birefringent, mix of agglomerates and primary particles, irregular or diamond shaped plates up to ~30 μm (see FIGS. 19(A) and 19(B)) | Birefringent, mainly agglomerates of tiny rounded irregular particles with some larger plate shaped primary particles, up to ~13 μm (see FIGS. 27(A) and 27(B)) |
| SEM | Loose agglomerates of plates and smaller irregular particles (see FIGS. 20(A) and 20(B)) | Rounded porous agglomerates of tiny particles (see FIGS. 28(A) and 28(B)) |
| TGA | No low temperature weight losses 31.5 wt. % loss 190-275° C. 39.6 wt. % loss 275-320° C. (see FIG. 21) | 2.0 wt. % loss 25-125° C., 7.2 wt. % loss 125-180° C., 13.5 wt. % loss 180-240° C. 48.3 wt. % loss 240-305° C. (see FIG. 29) |
| DSC | Sharp endotherm onset 239° C. (111.8 J/g) (see FIG. 21) | Broad endotherm (2 peaks) onset 102° C. (140.5 J/g) Broad endotherm onset 130° C. (23.0 J/g) Sharp endotherm onset 182° C. (6.1 J/g) Sharp endotherm onset 238° C. (62.7 J/g) (see FIG. 29) |

TABLE 4-continued

Characterization Summary of Scaled-up Salts

| | Salt A (prepared in THF) | Salt B (prepared in EtOAc) |
|---|---|---|
| GVS | Total weight change 0-90% RH = 0.8 wt. %, steady change in mass<br>XRPD of residue showed no change in form | Total weight change 0-90% RH = ~60 wt. %, stable until 80% RH then deliquesced<br>On desorption, moisture retained down to 60% RH<br>XRPD of residue showed mixture of mainly Orotate Pattern 2 with some Orotate Pattern 1 |
| Static stability 40° C./75% RH | No change (see FIG. 22) | Subtle changes, mainly Orotate Pattern 2, sticky material (see FIG. 30) |
| Static stability 25° C./96% RH | Subtle changes, mainly Orotate Pattern 1, runny material (see FIG. 22) | Sticky after 24 hours, deliquesced after 1 week (see FIG. 30) |

Based on the data obtained, Orotate Pattern 1 is understood to be a non-solvated bis-orotate complex. It is not clear how the orotic acid is bound to the nicotine. Although not intending to be limited by theory, it is believed the pKa values make it likely that one of the molecules of orotic acid is bound to the nicotine as a salt and the other is connected via hydrogen bonding rather than proton transfer (e.g., in the form of a salt-co-crystal). Specifically, the pKa values of orotic acid (5.85 and 8.95) suggest that in the (S)-nicotine bis-orotate crystal lattice, only 1 orotic acid molecule is ionized to form mono-protonated (S)-nicotine (protonation of the pyrrolidine nitrogen) in the salt. This would suggest that the $2^{nd}$ orotic acid molecule is held in the crystal lattice by hydrogen bonding rather than by proton transfer and ionization (protonation of the pyridine nitrogen in nicotine would not be predicted). Thus (S)-nicotine bis-orotate may be a salt/co-crystal hybrid form.

This form is thermally stable (melting at 239° C.) and is only slightly hygroscopic in the GVS experiment. However, longer exposure to high humidity (25° C./96% RH for 1 week) caused conversion to a runny material. Representative peak listings for the XPRD of nicotine orotate (Pattern 1, i.e., a bis-orotate salt-co-crystal) are provided in Table 5.

TABLE 5

Table of peak areas for Nicotine Orotate Pattern 1

| Peak | Angle 2-Theta ° | Intensity Count | Relative Intensity % |
|---|---|---|---|
| 1 | 8.8 | 5486 | 95.3 |
| 2 | 9.3 | 244 | 4.2 |
| 3 | 11.2 | 134 | 2.3 |
| 4 | 11.9 | 193 | 3.4 |
| 5 | 12.2 | 126 | 2.2 |
| 6 | 13.4 | 1806 | 31.4 |
| 7 | 14.2 | 924 | 16.1 |
| 8 | 15.6 | 101 | 1.8 |
| 9 | 16.5 | 840 | 14.6 |
| 10 | 17.7 | 3721 | 64.7 |
| 11 | 18.6 | 1621 | 28.2 |
| 12 | 19.8 | 1420 | 24.7 |
| 13 | 19.2 | 269 | 4.7 |
| 14 | 19.4 | 311 | 5.4 |
| 15 | 20.1 | 210 | 3.6 |
| 16 | 20.7 | 302 | 5.3 |
| 17 | 21.3 | 101 | 1.8 |
| 18 | 21.8 | 924 | 16.1 |
| 19 | 22.5 | 529 | 9.2 |
| 20 | 22.7 | 336 | 5.8 |
| 21 | 23.3 | 403 | 7.0 |
| 22 | 24.0 | 160 | 2.8 |
| 23 | 24.8 | 235 | 4.1 |
| 24 | 25.4 | 638 | 11.1 |
| 25 | 26.5 | 5754 | 100.0 |
| 26 | 27.5 | 420 | 7.3 |
| 27 | 27.7 | 428 | 7.4 |
| 28 | 28.4 | 756 | 13.1 |
| 29 | 29.3 | 2277 | 39.6 |
| 30 | 30.2 | 143 | 2.5 |
| 31 | 30.6 | 143 | 2.5 |
| 32 | 30.9 | 176 | 3.1 |
| 33 | 31.6 | 218 | 3.8 |
| 34 | 32.0 | 101 | 1.8 |
| 35 | 33.5 | 277 | 4.8 |
| 36 | 33.9 | 84 | 1.5 |
| 37 | 34.3 | 92.4 | 1.6 |
| 38 | 34.9 | 151 | 2.6 |
| 39 | 35.6 | 109 | 1.9 |
| 40 | 36.4 | 269 | 4.7 |
| 41 | 37.3 | 109 | 1.9 |
| 42 | 37.6 | 118 | 2.0 |
| 43 | 38.2 | 487 | 8.5 |
| 44 | 39.1 | 36.1 | 6.3 |

Orotate Pattern 2 is understood to be a mono-salt containing 0.5 mole eq. water, i.e. a mono-orotate hemi-hydrate. The (S)-nicotine mono-orotate hemi-hydrate exhibited complex behavior with an unusual DSC profile (mp 102° C.—$1^{st}$ onset of a broad endotherm, mp 130° C.—onset of broad exotherm (recrystallization), 182° C.—small endotherm (an unknown, but reproducible event) and 238° C.—sharp endotherm (mp of bis-orotate)). Orotate Patterns 1 and 2 have a complex relationship; during crystallization studies, Pattern 1 was observed to precipitate initially and then convert to Pattern 2 upon stirring at 5° C. or on addition of an excess of nicotine. Orotate Pattern 2 exhibits complex thermal behavior, so further characterization was carried out. Karl Fischer experiments showed that the sample contains 0.5 mole eq. water, which is lost by 140° C. (the first weight loss seen in the TGA). The second weight loss seen in the TGA is not caused by water loss (no additional water was detected by KF at 190° C.). See FIG. 29.

A variable temperature XRPD experiment showed the conversion of Orotate Pattern 2 to Pattern 1 on heating. The first endotherm seen in the DSC is the melt of Pattern 2, with the release of the water and the exotherm is the re-crystallization of Pattern 1, with associated loss of nicotine (second weight loss in the TGA). No change was seen in the diffractogram or visually at 180-200° C. so it is not clear what is causing this endotherm in the DSC (but repeat DSC experiments showed that it is reproducible). The final endotherm and associated weight loss is the dissociation of the mono-salt and release of the remainder of the nicotine to leave orotic acid. This was confirmed by $^1$H NMR analysis of the residue, which was consistent with orotic acid. Representative peak listings for the XPRD of nicotine orotate (Pattern 2, i.e., a mono orotate salt) are provided in Table 6, below.

TABLE 6

Table of peak areas for Nicotine Orotate Pattern 2

| Peak | Angle 2-Theta ° | Intensity Count | Relative Intensity % |
|---|---|---|---|
| 1 | 7.7 | 504 | 11.3 |
| 2 | 9.1 | 2219 | 49.8 |
| 3 | 9.8 | 698 | 15.7 |
| 4 | 11.9 | 269 | 6.0 |
| 5 | 12.5 | 328 | 7.4 |
| 6 | 13.1 | 92.5 | 2.1 |
| 7 | 14.7 | 2824 | 63.4 |
| 8 | 15.4 | 4455 | 100.0 |
| 9 | 15.9 | 311 | 7.0 |
| 10 | 17.3 | 4195 | 94.2 |
| 11 | 17.9 | 462 | 10.4 |
| 12 | 18.2 | 1219 | 27.4 |
| 13 | 18.6 | 714 | 16.0 |
| 14 | 19.3 | 757 | 17.0 |
| 15 | 19.7 | 933 | 20.9 |
| 16 | 21.3 | 378 | 8.5 |
| 17 | 22.1 | 353 | 7.9 |
| 18 | 23.4 | 580 | 13.0 |
| 19 | 25.0 | 1345 | 30.2 |
| 20 | 25.4 | 1875 | 42.1 |
| 21 | 26.3 | 925 | 20.8 |
| 22 | 26.6 | 328 | 7.4 |
| 23 | 27.0 | 2177 | 48.9 |
| 24 | 27.8 | 723 | 16.2 |
| 25 | 28.7 | 471 | 10.6 |
| 26 | 29.2 | 933 | 20.9 |
| 27 | 29.5 | 1261 | 28.3 |
| 28 | 30.4 | 109 | 2.5 |
| 29 | 31.3 | 395 | 8.9 |
| 30 | 32.1 | 193 | 4.3 |
| 31 | 33.3 | 269 | 6.0 |
| 32 | 34.9 | 210 | 4.7 |
| 33 | 36.3 | 160 | 3.6 |
| 34 | 37.4 | 429 | 9.6 |
| 35 | 37.6 | 168 | 3.8 |
| 36 | 38.5 | 370 | 8.3 |
| 37 | 39.2 | 168 | 3.8 |

Orotate Pattern 2 is not stable to exposure to high humidity; after 1 week at 40° C./75% RH the sample had become a sticky material (and shows subtle changes in the XRPD diffractogram) whilst after 1 week at 25° C./96% RH the sample had deliquesced. During the GVS experiment this form did not adsorb much water until 80% RH, where it deliquesced. On reducing the humidity, the water was lost by 60% RH with analysis of the residue showing that the sample had re-crystallized. This residue, however, contained some Pattern 1 material, suggesting that some of the nicotine was lost during the deliquescence and re-crystallization of the salt.

Example 2

Salt of Nicotine with Fumaric Acid

A screening experiment is first conducted to evaluate a solvent free method for the formation of a salt of fumaric acid. Orotic acid (50 mg+/−1 mg) is weighed into glass vials and (S)-Nicotine (2 molar equivalents) is dispensed into each vial, vials are stirred at 50° C. for 1 hour, cooled to 5° C. at 0.1° C./min, and stirred at 5° C. overnight. Upon the addition of nicotine, the material was observed to be a suspension and the material remained a suspension (with undissolved acid) after 1 hour. After cooling, the material was observed to be a solid brown solution. After stirring at 5° C. overnight, solids are sampled and characterized by XRPD. The XRPD analysis results indicate that the solid present in the vial comprises crystalline material, and peaks for fumaric acid as well as additional peaks are observed. The material is matured and after 1 week, the material is in the form of a brown oil/white solid. Again, XRPD analysis of this material indicates the presence of crystalline material, and peaks for fumaric acid as well as additional peaks are observed.

Various screening experiments are next conducted to evaluate alternative (solvent-based) means for the preparation of fumaric acid salts of nicotine. Experiments are conducted to evaluate the preparation of fumaric salt via slow evaporation from various solvents. Fumaric acid (50 mg+/−1 mg) is weighed into glass vials and the relevant solvent is added at 3, 10, and 20 volumes at 50° C. to try to form solutions of the fumaric acid. Nicotine (1 molar equivalent) is added. The resulting mixtures are stirred at 50° C. for 1 hour, cooled to 5° C. at 0.1° C. per minute, and then stirred at 5° C. overnight. Solids are sampled and analyzed by XPRD (see FIG. 31); solids exhibiting new XRPD patterns are filtered and dried under vacuum overnight.

Samples exhibiting XRPD patterns consistent with the acid/coformer and any samples in the form of oils/gums are matured (shaken in 8 hour cycles at 50° C./RT). Solutions are left to evaporate slowly at ambient conditions via loosened lids on the vials. Any resulting solids are sampled and analyzed by XRPD (see FIG. 32), with any oils/gums present at this stage being matured as described above. Samples that remain solutions after anti-solvent addition are left to evaporate under ambient conditions. A summary of these solvent-mediated screens and the observations associated with each screen are provided in Table 7 below.

TABLE 7

Solvent-mediated screen for formation of salt from nicotine and fumaric acid

| Solvent | Anti-solvent | Observations |
|---|---|---|
| THF | n/a | Solution after addition of nicotine |
| | | Solution after 1 h at 50° C. |
| | | Solution after cooling to 5° C. |
| | | Yellow oil after initial evaporating step |
| | | Oil matured - remained in oil form |
| | | No XRPD obtained |
| Water | n/a | Solution after addition of nicotine |
| | | Solution after 1 h at 50° C. |
| | | Solution after cooling to 5° C. |
| | | Solution after initial evaporating step |
| | | Oil formed after further evaporation |
| | | No XRPD obtained |

TABLE 7-continued

Solvent-mediated screen for formation
of salt from nicotine and fumaric acid

| Solvent | Anti-solvent | Observations |
|---|---|---|
| Ethanol | TBME | Solution after addition of nicotine<br>Solution after 1 h at 50° C.<br>Solution after cooling to 5° C.<br>Anti-solvent, TBME added, material remained a solution after addition of 600 μL TBME<br>Solution after initial evaporating step<br>Oil formed after further evaporation<br>No XRPD obtained |
| MEK | n-heptane | Suspension after addition of nicotine<br>Suspension after 1 h at 50° C.<br>Viscous oil after cooling to 5° C.<br>Material matured and remained in oil form<br>No XRPD obtained |
| IPA/water (80/20 volume) | n/a | Solution after addition of nicotine<br>Solution after 1 h at 50° C.<br>Solution after cooling to 5° C.<br>Solution after initial evaporating step<br>Oil formed after further evaporation<br>No XRPD obtained |
| Ethyl acetate | n-heptane | Partial dissolution after addition of nicotine<br>Gummy solid after 1 h at 50° C.,<br>Suspension/gum after cooling to 5° C., XRPD indicates crystalline pattern<br>Material filtered to give solid |

A further experiment is conducted to evaluate the preparation of a fumaric acid salt via grinding. Fumaric acid (50 mg+/−1 mg) is weighed into a glass vial and nicotine (1 molar equivalent) is added, giving a slurry. Two ball bearings (3 mm, stainless steel) are added to the resulting mixture and the sample is ground for 2 hours at 650 rpm in a Fritsch Pulverisette mill, giving a white paste. The material is analyzed by XPRD, indicating a new pattern, deliquescing. The solid is isolated from the grinding vial and filtered.

Overall, the neat nicotine screen gave a sticky solid (containing some acid), the grinding screen gave a crystalline solid, and the ethyl acetate/heptane screen gave a crystalline solid. Other methods provided an oil or solution. Two different XRPD patterns were observed for the fumaric acid salts (arbitrarily referred to herein as "Fumarate Pattern 1" and "Fumarate Pattern 2," depending on the method of preparation. Fumarate Pattern 1 was made by grinding and by preparation in ethyl acetate and is understood to contain 2 equivalents of fumaric acid (non-solvated) and deliquesced at 40° C./75% RH. Fumarate Pattern 2 was made in neat nicotine and is understood to be a non-solvated mono salt, and deliquesced at 40° C./75% RH. Table 8 further provides additional characterization data for the fumaric acid salts.

TABLE 8

Data correlated to method of preparation of fumaric acid salt

Figure 31:
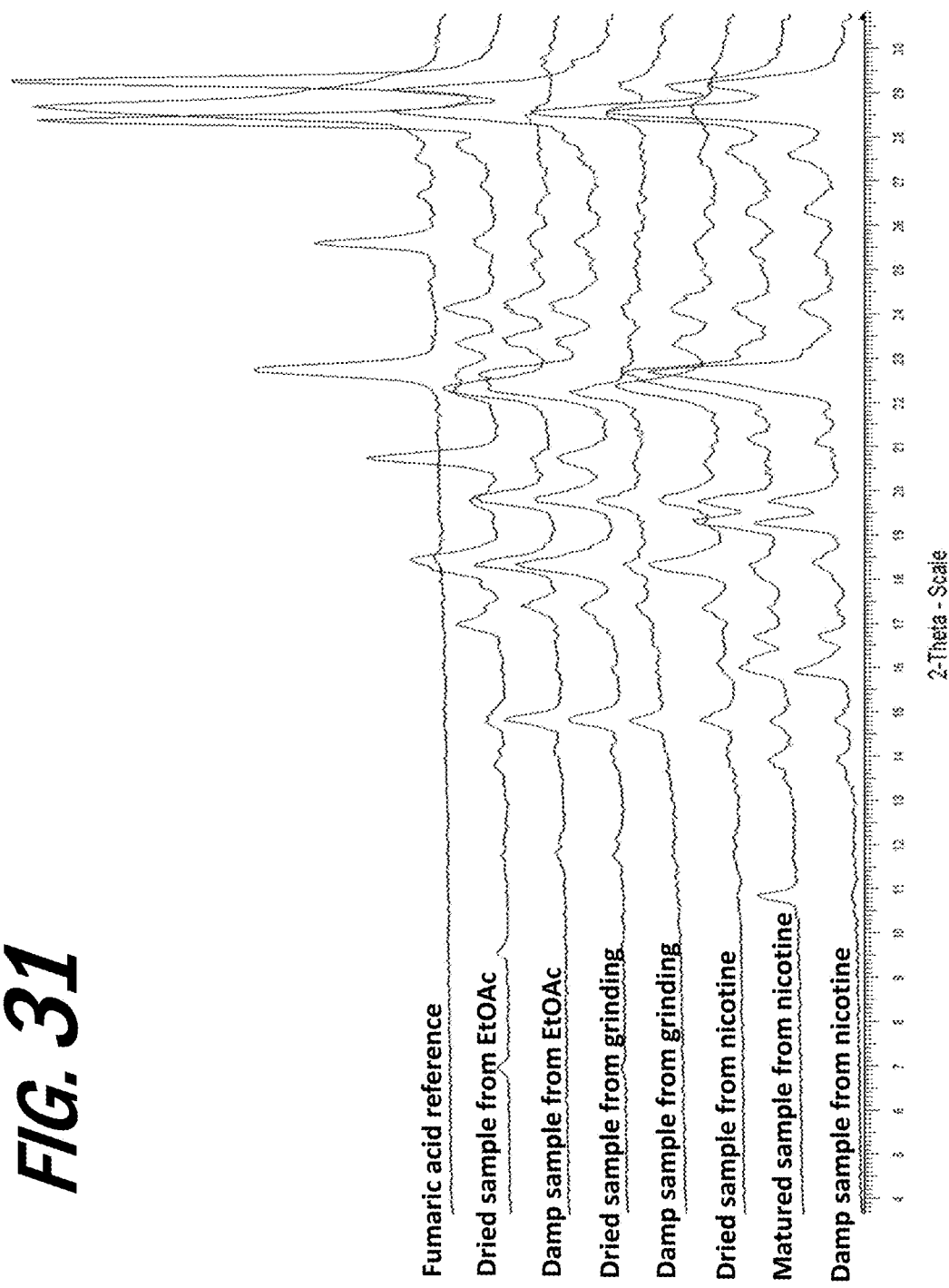
FIG. 31 provides XRPD diffractograms of materials prepared from nicotine and fumaric acid by various methods.
Figure 32:
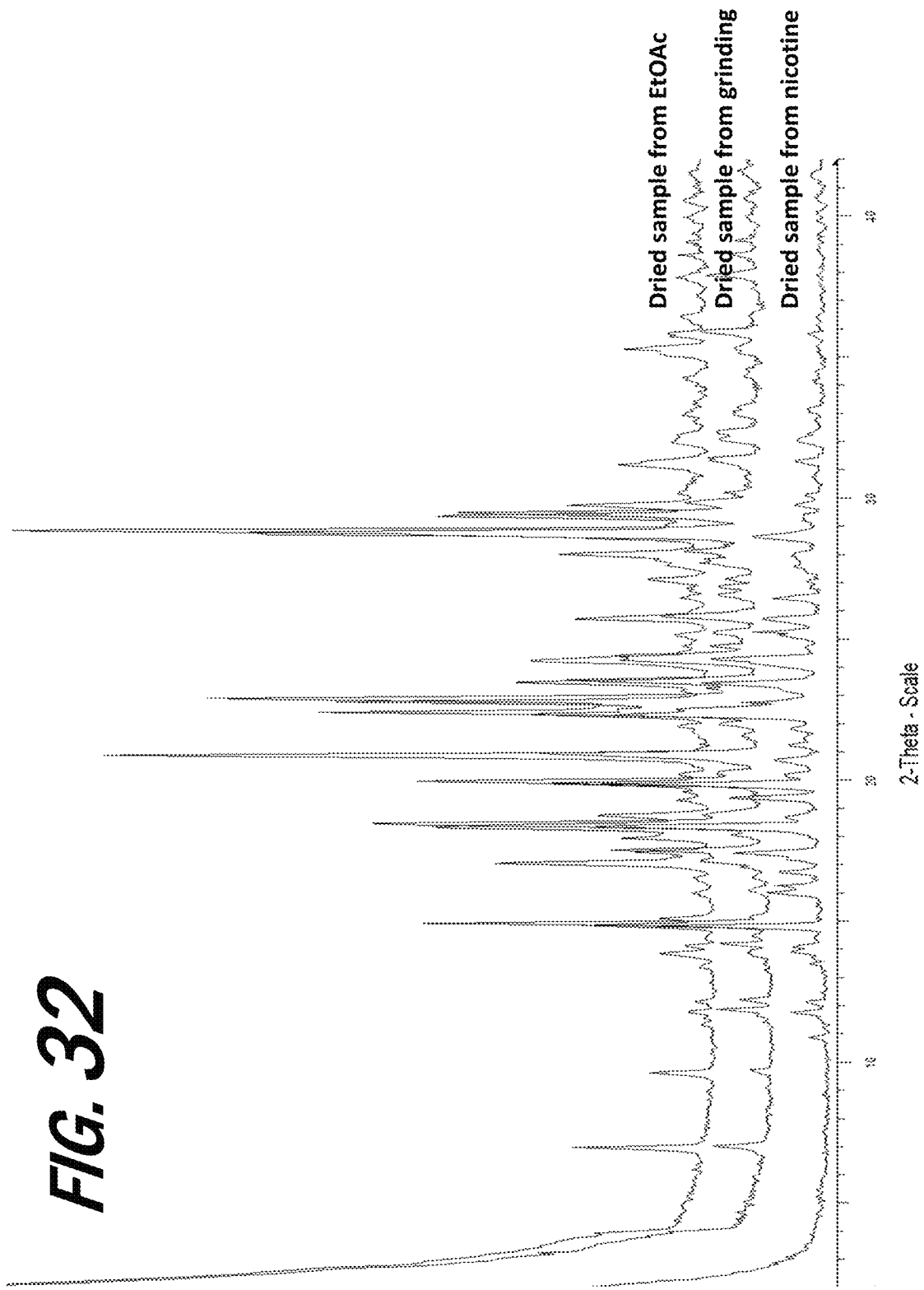
FIG. 32 provides high resolution XRPD diffractograms of solid materials recovered from nicotine and fumaric acid by various methods.
Figure 33:
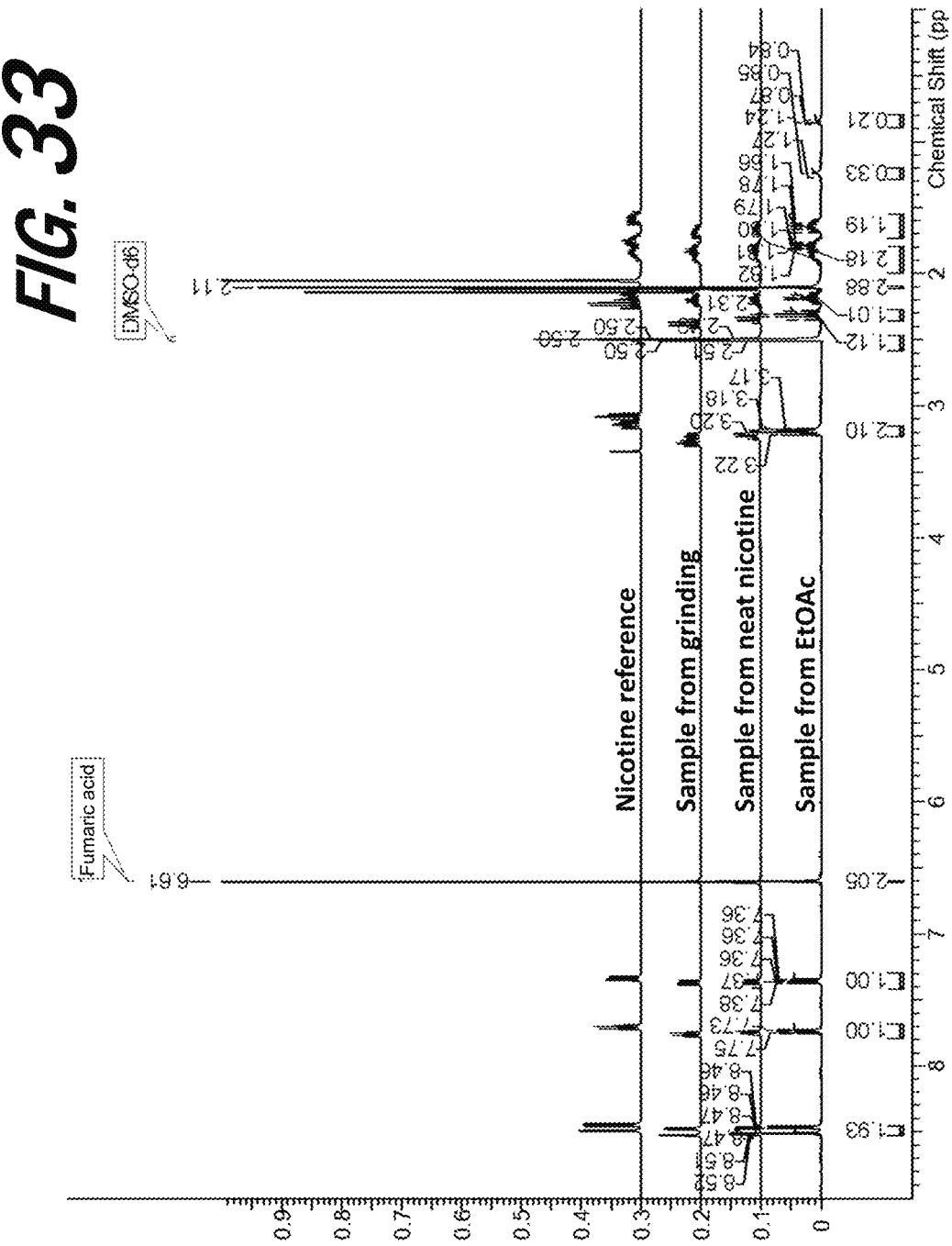
FIG. 33 provides $^1$H NMR spectra of materials prepared from nicotine and fumaric acid by various methods.
Figure 34:
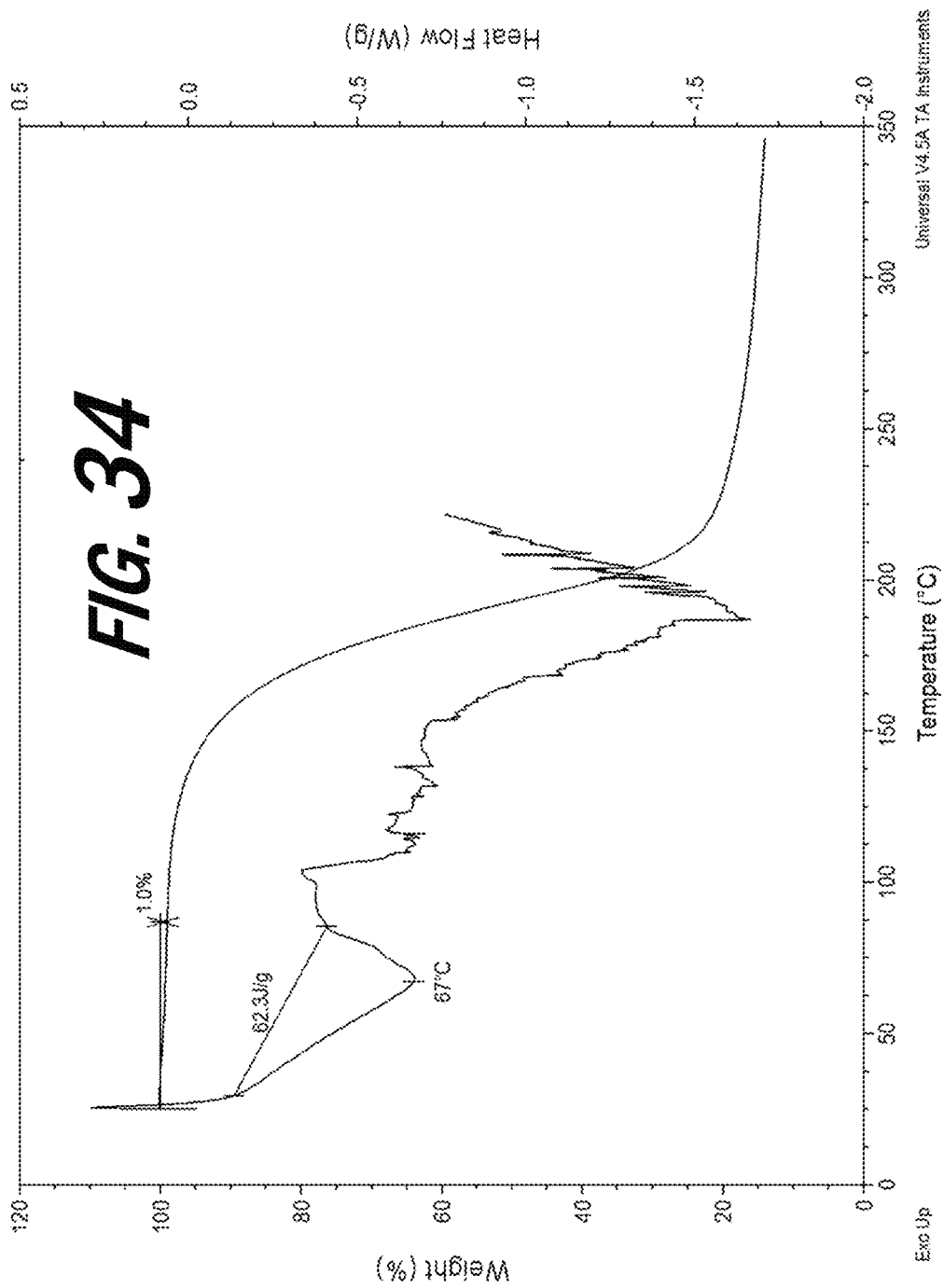
FIG. 34 provides an overlay of TGA and DSC thermograms for a material prepared from nicotine and fumaric acid in neat nicotine.
Figure 35:
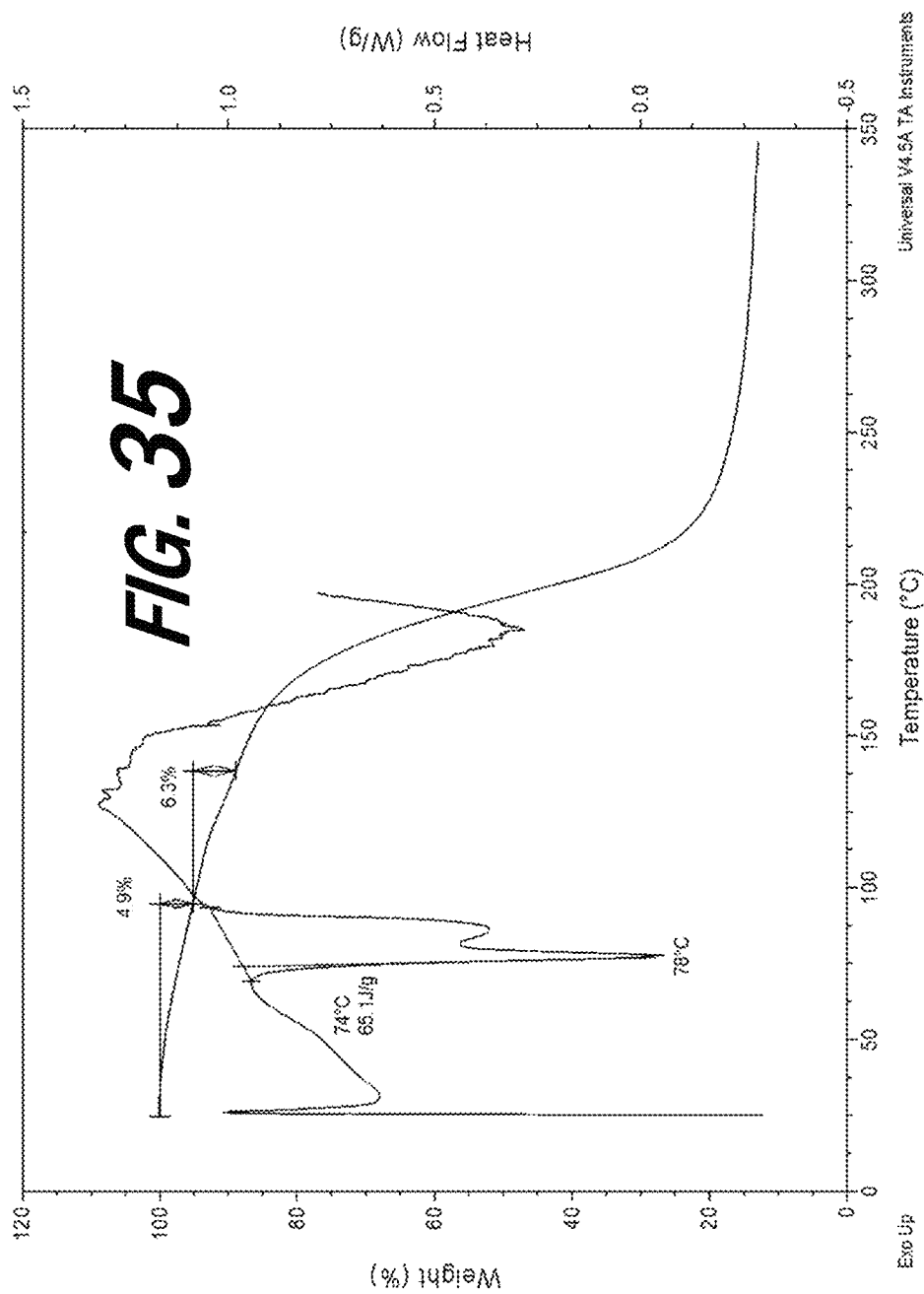
FIG. 35 provides an overlay of TGA and DSC thermograms for a material prepared from nicotine and fumaric acid by grinding.
Figure 36:
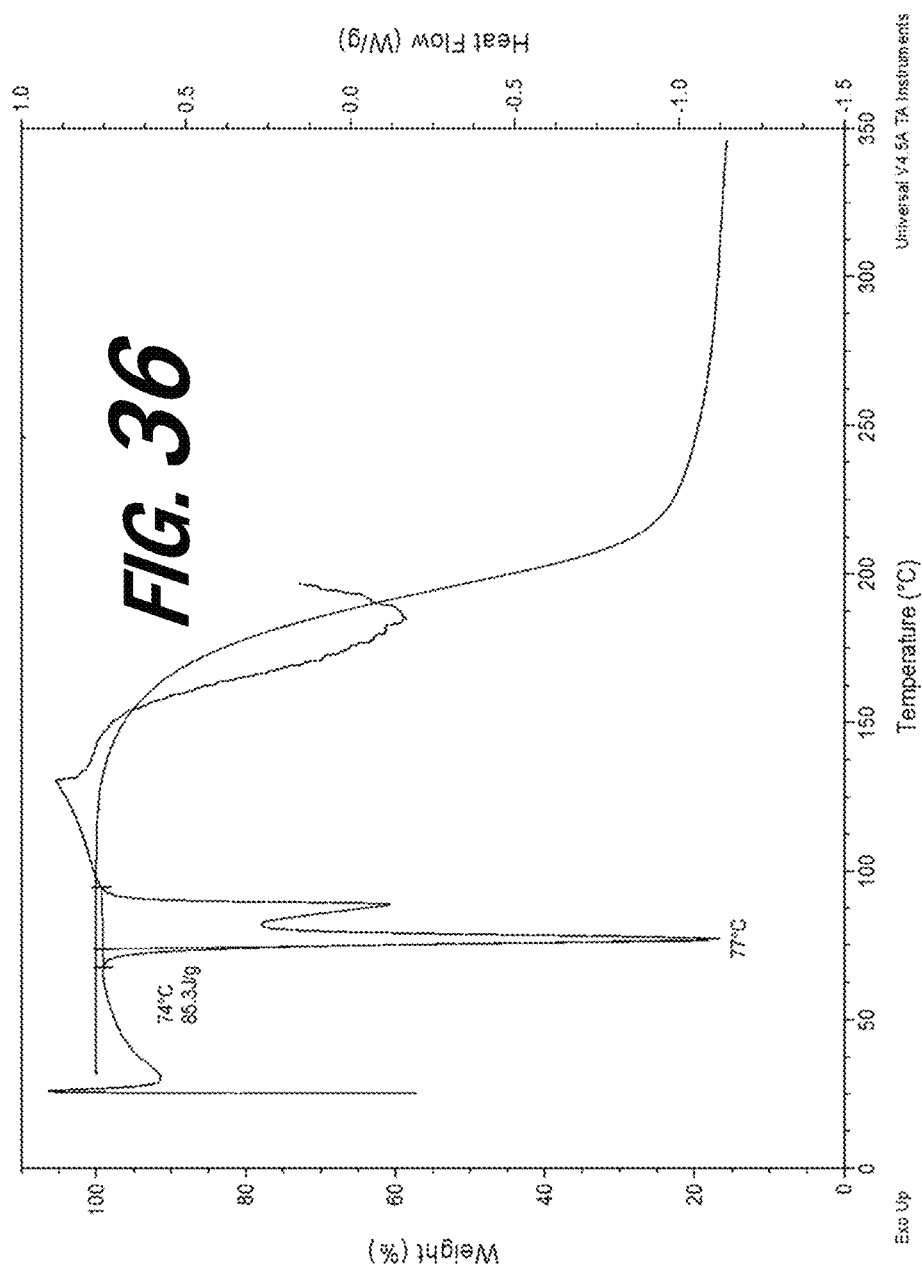
FIG. 36 provides an overlay of TGA and DSC thermograms for a material prepared from nicotine and fumaric acid in EtOAc.

| Method of salt preparation | XRPD Pattern of solid See FIGS. 31 and 32 | $^1$H NMR See FIG. 33 | TGA | DSC | Result |
|---|---|---|---|---|---|
| Formation in neat nicotine | Pattern 2 (damp sample), Pattern 1 (dry sample) | Peak shifts on acid, ratio nicotine:orotic acid 1:1.0 | 1.0 wt. % loss 25-80° C. Complete wt. loss from ~100° C. See FIG. 34 | Broad endotherm onset 25° C. See FIG. 34 | Deliquesced (1 day) Unstable mono salt |
| Grinding | Pattern 1 | Peak shifts on acid, ratio nicotine:fumaric acid 1:1.9 | 4.9 wt. % loss 25-90° C. 6.3 wt. % loss 90-140° C. Complete wt. loss ~150° C. See FIG. 35 | Endotherm (2 peaks) onset 74° C. See FIG. 35 | Deliquesced (1 day) Unstable bis salt (later shown to be a mono-salt) |
| Formation in ethyl acetate | Pattern 1 | Peak shifts on acid, ratio nicotine:fumaric acid 1:1.5 | No wt. loss prior to degradation from ~110° C. See FIG. 36 | Endotherm (2 peaks) onset 74° C. See FIG. 36 | Deliquesced (1 day) Unstable salt |

Figure 37:
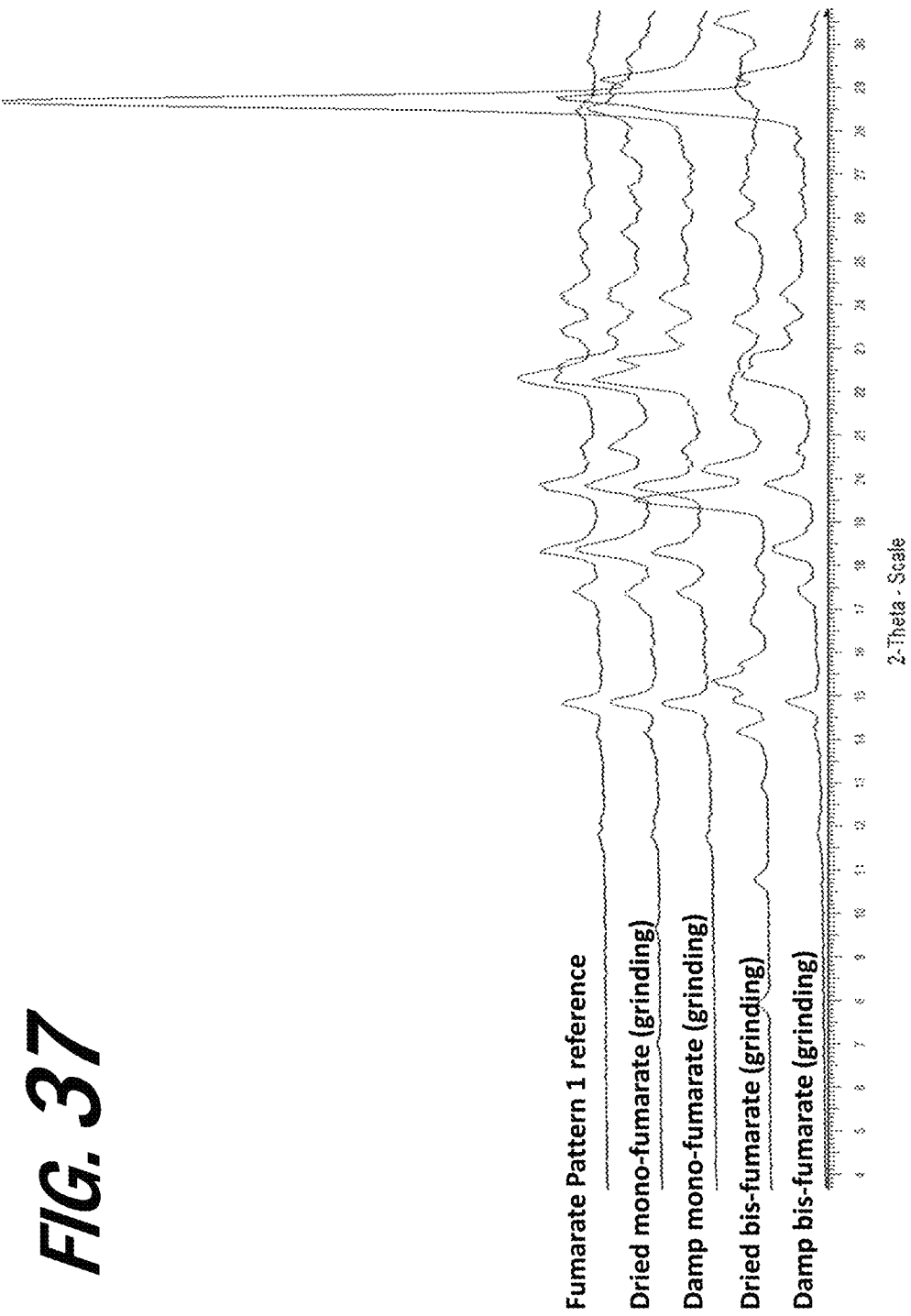
FIG. 37 provides XRPD diffractograms for nicotine fumarate salts obtained by grinding.
Figure 38:
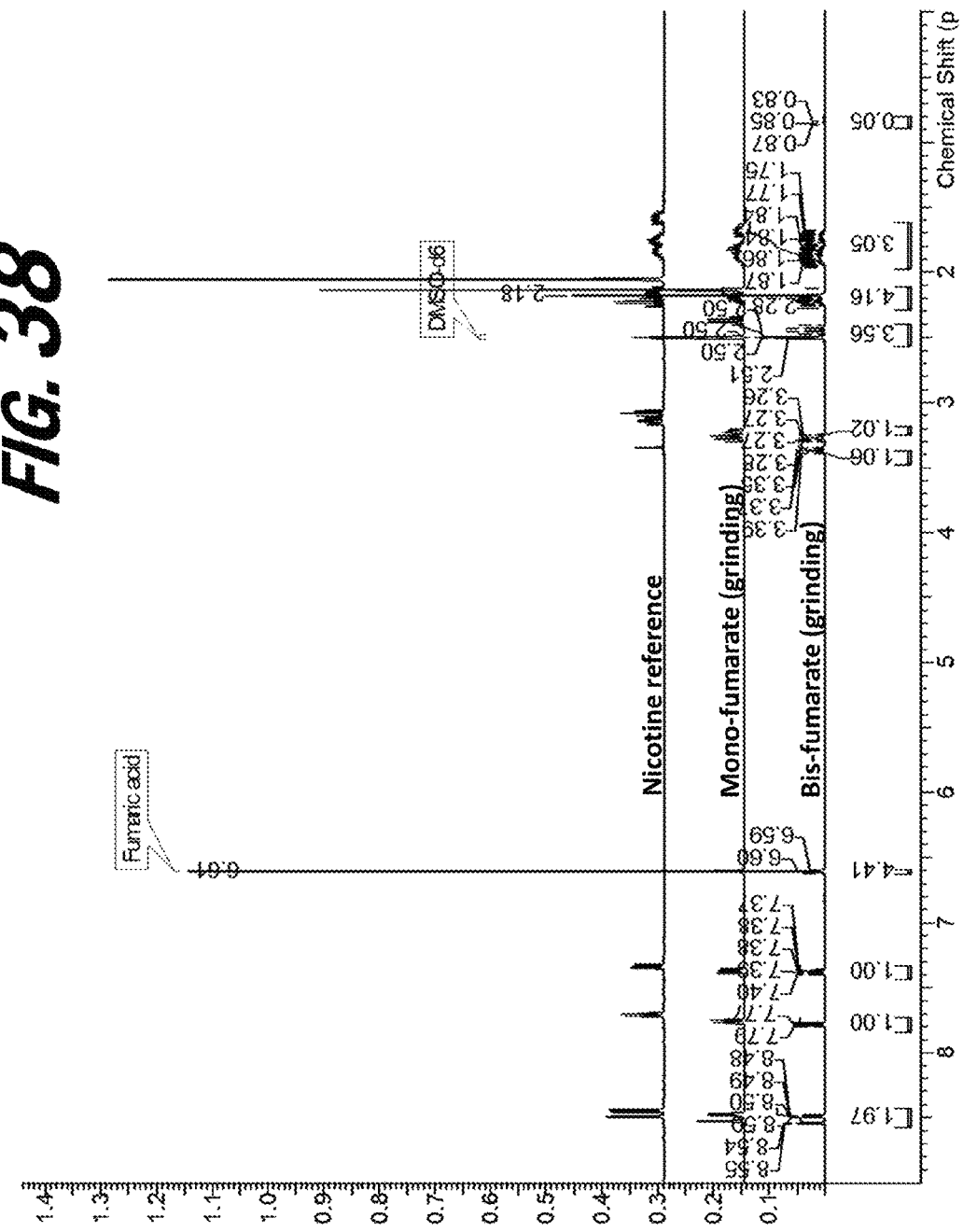
FIG. 38 provides $^1$H NMR spectra for the fumarate salts obtained by grinding.

Grinding experiments were carried out at mono- and bis-stoichiometry to confirm the stoichiometry of Pattern 1 (see FIGS. 37 and 38). Fumaric acid (60 mg) is weighed into vials and 0.5 or 1.0 equivs. Nicotine and 2 ball bearings (3 mm, stainless steel) are added. Samples are ground for 2 hours at 650 rpm in a Fritsch Pulverisette mill. Samples are triturated with hexane and dried under vacuum overnight prior to characterization. The material prepared with 0.5 equivalents nicotine was a wet solid after addition of nicotine, and a white solid after grinding, giving an XRPD consistent with Fumarate Pattern 1 (as compared with material prepared in EtOAc). The material prepared with 1 equivalent of nicotine was a paste after adding nicotine, and a white paste after grinding, giving an XRPD consistent with Fumarate Pattern 1. As such, results indicate that grinding experiments, carried out at mono- and bis-stoichiometries, both produced solids consistent with Fumarate Pattern 1, suggesting that Fumarate Pattern 1 is more likely to be a mono-salt.

Solvent-mediated experiments are next conducted using a range of anti-solvents to try to form a more homogeneous powdery solid that is easier to filter. Experiments are also carried out with 1 mole equivalent of nicotine to confirm the stoichiometry of this form. Fumaric acid (approximately 50 mg) is weighed into 2 ml vials and 1 or 2 mole eq. nicotine are added. Samples are left to stir at 50° C. for ~10 minutes and then anti-solvents are added to some of the experiments. Samples were stirred at 50° C. for 1 hour, then were cooled to 5° C. at 0.1° C./min. Samples are stirred at 5° C. overnight then filtered, air dried and analyzed by XRPD. Samples are filtered and dried under vacuum overnight prior to re-analysis by XRPD and stoichiometry is determined by $^1$H NMR.

to Pattern 1, an observation consistent with these two forms being polymorphs of a mono-salt. Fumarate Pattern 2 is formed in neat nicotine, forming a very hard gum that is not practical to isolate on a large scale. Pattern 2 samples that were filtered from neat nicotine and dried in a vacuum oven converted to a form similar to Fumarate Pattern 1 on drying. Although not intending to be limited by theory, it is believed that Fumarate Pattern 2 represents a metastable polymorph of the mono-fumarate salt.

TABLE 9

Preparation of fumaric acid salt in neat nicotine (with anti-solvent)

| Method of salt preparation | Observation on addition of solvent | Observation after cooling to 5° C. | XRPD (damp) | XRPD (dry), after filtering/ evaporation | $^1$H NMR |
|---|---|---|---|---|---|
| Neat nicotine | slurry | White solid (with brown liquid) | Fumarate Pattern 2 | Some changes, consistent with material prepared in EtOAc | Peak shifts, ratio nicotine:fumaric acid 1:1.1 |
| Neat nicotine/ TBME as anti-solvent | gum | White solid (white suspension and orange sticky layers) | Fumarate Pattern 1 | Some changes, consistent with material prepared in EtOAc | Peak shifts, ratio nicotine:fumaric acid 1:1.2 |
| Neat nicotine/ heptane as anti-solvent | gum | White solid (with white suspension and orange sticky layers) | Fumarate Pattern 1 | Some changes, consistent with material prepared in EtOAc | Peak shifts, ratio nicotine:fumaric acid 1:1.4 |
| Neat nicotine/ hexane as anti-solvent | Gum | White solid (with white suspension and orange sticky layers) | Fumarate Pattern 1 | Some changes, consistent with material prepared in EtOAc | Peak shifts, ratio nicotine:fumaric acid 1:1.2 |
| Neat nicotine/ THF as anti-solvent | Gum | Thick suspension | Fumarate Pattern 1 | Fumarate Pattern 1 | Peak shifts, ratio nicotine:fumaric acid 1:1.0 |
| Neat nicotine/ dichloromethane (DCM) as anti-solvent | Nearly dissolved | Solution | n/a | n/a | |
| Neat nicotine/ EtOAc as anti-solvent | Gum | White solid (with white suspension and orange sticky layers) | Fumarate Pattern 1 | Fumarate Pattern 1 | Peak shifts, ratio nicotine:fumaric acid 1:1.1 |
| Neat nicotine/ MEK as anti-solvent | Gum | Thick suspension | Fumarate Pattern 1 | Fumarate Pattern 1 | Peak shifts, ratio nicotine:fumaric acid 1:1.0 |
| Neat nicotine/ IPA as anti-solvent | Gum | Solution | n/a | n/a | |

Results show that Fumarate Pattern 1 was made from all of the experiments presented in Table 9 where an anti-solvent was used and where a solid was formed. It was determined that experiments using THF and MEK are preferred methods for producing Fumarate Pattern 1. It was only possible to make Fumarate Pattern 2 from neat nicotine, which resulted in sticky solids, which proved difficult to filter. Once dried, the Pattern 2 solids had converted to Pattern 1. Further analysis of the original Fumarate Pattern 2 sample, showed that this sample also converted to Fumarate Pattern 1 on drying.

Characterization results indicate that Fumarate Pattern 1 is a mono-salt and not a bis-salt as was previously thought. When using anti-solvent to wash away excess nicotine and to form a material amenable to filtration, Pattern 2 converts The fumarate salts are prepared on a larger scale. Fumaric acid (3.6 g, 0.031 moles) is added to nicotine (2 mole equivalents, 10 ml) and warmed to 50° C. The sample is stirred at 50° C. for 30 minutes, causing partial dissolution of the acid. THF (10 vols with respect to the acid, 40 ml) is added, forming a gummy precipitate and the sample is stirred at 50° C. for 1 hour. The sample is then cooled to 5° C. at 0.1° C./min and stirred at 5° C. overnight. A sample of the resulting white suspension is analyzed by XRPD and found to be consistent with Fumarate Pattern 1 (see FIG. 39). The sample is filtered through a glass frit, washed with THF, sucked dry and then further dried under vacuum for 3 days at ambient temperature to give a sticky, coarse, off-white powder, 4.68 g=54.6 wt. % yield.

The resulting solid is analyzed by various techniques, as summarized below in Table 10.

TABLE 10

Characterization Summary of Scaled-up Fumarate Salt

Figure 39:
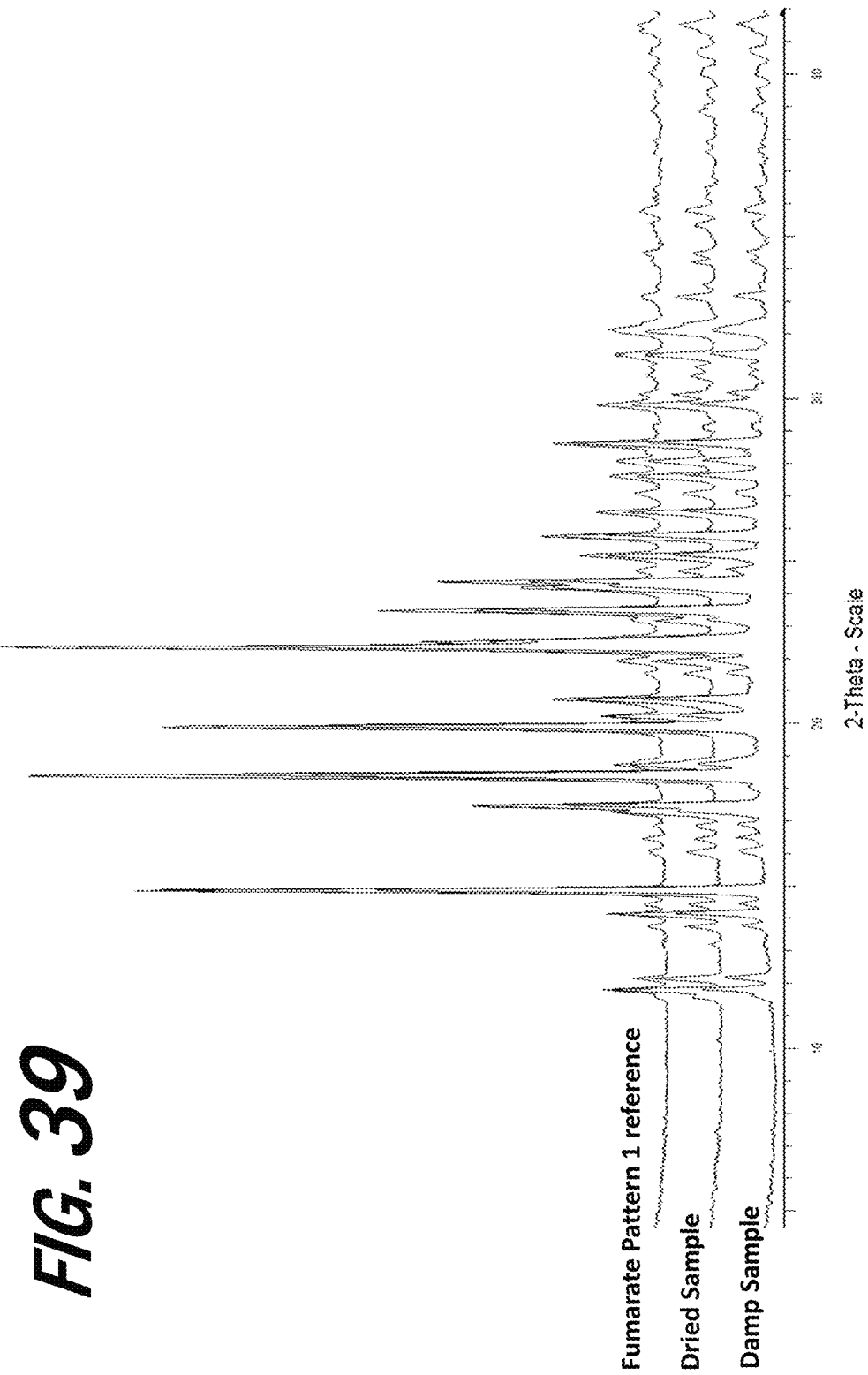
FIG. 39 provides high resolution XRPD diffractograms for scaled up nicotine fumarate salt (prepared in THF)
Figure 42:
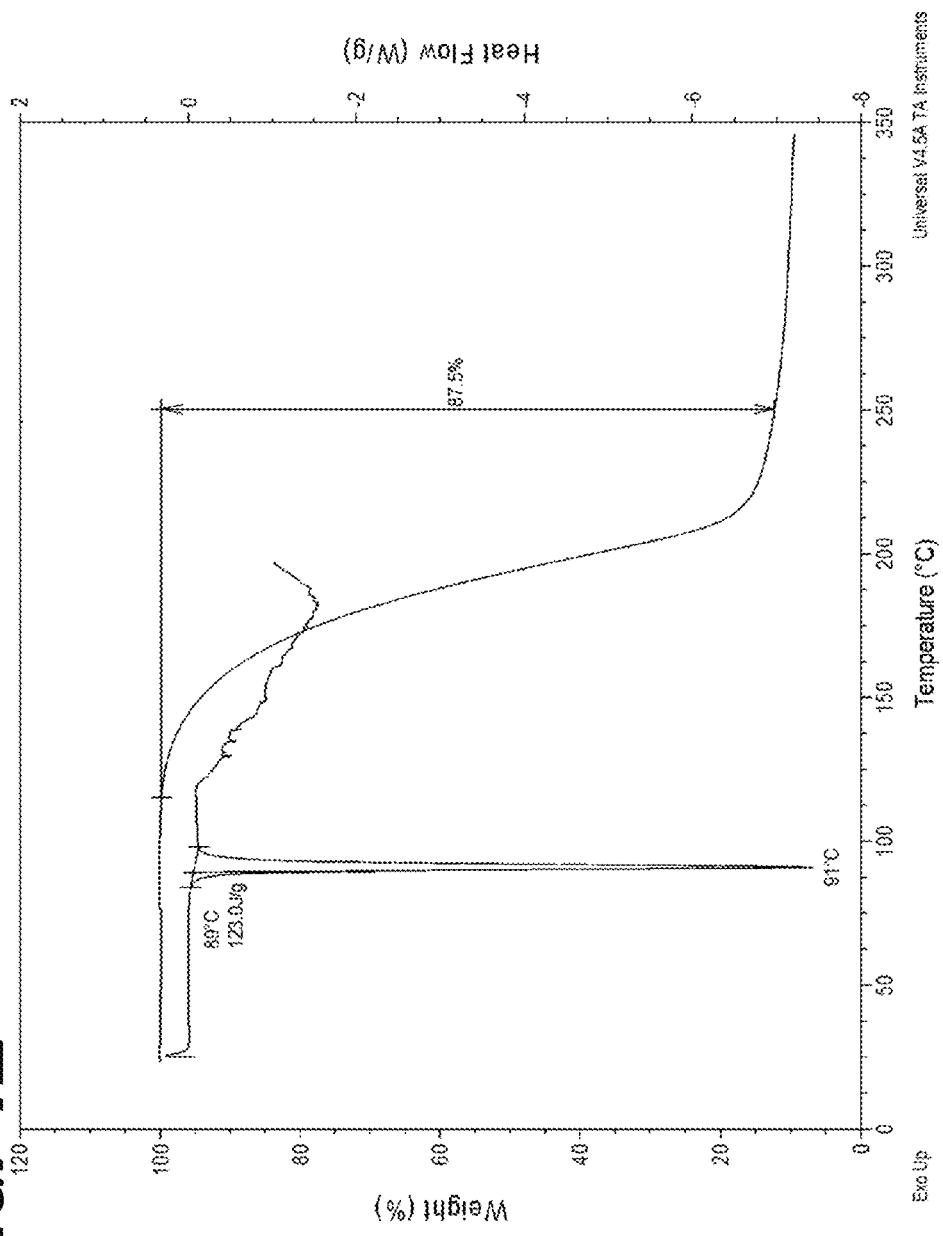
FIG. 42 provides an overlay of TGA and DSC thermograms for a scaled up material prepared from nicotine and fumaric acid in THF.

| | Fumarate salt (prepared in THF) |
|---|---|
| Appearance | Sticky, coarse white powder |
| Yield (dry) | 54.6 wt. % |
| XRPD damp | Fumarate Pattern 1 See FIG. 39 |
| XRPD dry | Fumarate Pattern 1 See FIG. 39 |
| $_1$H NMR | Peak shifts, no THF, 1.0 equiv. acid |
| Karl Fischer | n/a |
| Optical microscopy | Large agglomerates of particles, sticky material, not possible to disperse in oil See FIGS. 40(A) and 40(B) |
| SEM | Loose agglomerates of particles with a porous surface with cracks and indentations See FIGS. 41(A) and 41(B) |
| TGA | No low temperature weight losses Gross degradation after ~120° C. See FIG. 42 |
| DSC | Sharp endotherm onset 89° C. (123.0 J/g) See FIG. 42 |
| GVS | Total weight change 0-90% RH = 82 wt. %, sample deliquesces and remains a liquid Sample does not reach equilibrium on adsorption steps No hysteresis on desorption |
| Static stability 40° C./75% RH | Deliquesced after 24 hours |
| Static stability 25° C./96% RH | Deliquesced after 24 hours |

Representative peak listings for the XPRD of nicotine fumarate (Pattern 1, i.e., a non-solvated mono fumarate salt) are provided in Table 1, below.

TABLE 11

Table of peak areas for nicotine fumarate

| Peak | Angle 2-Theta ° | Intensity Count | Relative Intensity % |
|---|---|---|---|
| 1 | 11.6 | 148 | 3.7 |
| 2 | 11.8 | 491 | 12.4 |
| 3 | 12.2 | 337 | 8.5 |
| 4 | 13.8 | 189 | 4.8 |
| 5 | 14.1 | 621 | 15.7 |
| 6 | 14.4 | 189 | 4.8 |
| 7 | 14.9 | 2696 | 68.4 |
| 8 | 16.1 | 177 | 4.5 |
| 9 | 16.5 | 189 | 4.8 |
| 10 | 16.9 | 154 | 3.9 |
| 11 | 17.3 | 573 | 14.5 |
| 12 | 17.5 | 1395 | 35.4 |
| 13 | 18.0 | 76.9 | 1.9 |
| 14 | 18.4 | 3943 | 100.0 |
| 15 | 18.8 | 402 | 10.2 |
| 16 | 19.9 | 3175 | 80.5 |
| 17 | 20.2 | 514 | 13.0 |
| 18 | 20.8 | 845 | 21.4 |
| 19 | 21.5 | 160 | 4.0 |
| 20 | 22.0 | 296 | 7.5 |
| 21 | 22.4 | 3571 | 90.6 |
| 22 | 22.6 | 1507 | 38.2 |
| 23 | 23.2 | 290 | 7.3 |
| 24 | 23.5 | 1697 | 43.0 |
| 25 | 24.2 | 981 | 24.9 |
| 26 | 24.4 | 1413 | 35.8 |
| 27 | 24.7 | 189 | 4.8 |
| 28 | 25.2 | 579 | 14.7 |
| 29 | 25.8 | 1052 | 26.7 |
| 30 | 26.6 | 526 | 13.3 |
| 31 | 27.1 | 154 | 3.9 |
| 32 | 27.7 | 508 | 12.9 |
| 33 | 28.1 | 396 | 10.0 |
| 34 | 28.6 | 786 | 19.9 |
| 35 | 29.2 | 88.7 | 2.2 |
| 36 | 29.8 | 502 | 12.7 |
| 37 | 30.2 | 231 | 5.8 |
| 38 | 30.8 | 94.6 | 2.4 |
| 39 | 31.0 | 118 | 3.0 |
| 40 | 31.4 | 378 | 9.6 |
| 41 | 32.1 | 384 | 9.7 |
| 42 | 33.2 | 231 | 5.8 |
| 43 | 34.3 | 118 | 3.0 |
| 44 | 34.6 | 136 | 3.4 |
| 45 | 35.4 | 100 | 2.5 |
| 46 | 35.8 | 142 | 3.6 |
| 47 | 36.6 | 88.7 | 2.2 |
| 48 | 38.9 | 118 | 3.0 |
| 49 | 39.6 | 100 | 2.5 |
| 50 | 40.0 | 106 | 2.7 |
| 51 | 40.7 | 148 | 3.7 |
| 52 | 41.6 | 213 | 5.4 |

Fumarate Pattern 1 is understood to be a non-solvated mono-salt, which is prone to deliquescing at elevated humidity. This form is hygroscopic and needs to be protected from moisture as it is shown to constantly gain moisture from 0-90% RH (82% weight gain) in the GVS isotherm and deliquesces at elevated humidities (≥75% RH). Further, once it deliquesces, it does not re-crystallize when the humidity is reduced.

Example 3

Salts of Nicotine with L-Pyroglutamic Acid

Under most conditions studied (comparable to those described above with respect to attempts to prepare salts from nicotine and orotic acid and fumaric acid), mixtures of L-pyroglutamic acid and nicotine yielded oils or gums. However, in neat nicotine, some crystalline material is obtained.

Pyroglutamic acid (50 mg+/−1 mg) is weighed into a glass vial and (S)-Nicotine (2 molar equivalents) is dispensed into the vial, the vial is stirred at 50° C. for 1 hour, cooled to 5° C. at 0.1° C./min, and stirred at 5° C. overnight. Upon the addition of nicotine, the material was observed to be a suspension and the material remained a suspension (with undissolved acid) after 1 hour. After cooling, the material was observed to be a white solid. After stirring at 5° C. overnight, solids are sampled and characterized by XRPD. The XRPD analysis results indicate that the solid present in the vial is partially crystalline. This material was identified as a possible salt, but was very sticky/hygroscopic after drying. The material was determined to have a nicotine:acid ratio of 1:~4.5 and excess nicotine could not be washed away with n-heptane. The material deliquesced at ambient conditions. Attempts to mature the material resulted in the formation of a brown oil, which was not further analyzed.

Example 4

Pyrolysis Studies

The salts of Examples 1 and 2 (nicotine mono-fumarate, nicotine mono-orotate hemi-hydrate, and nicotine bis-orotate) decompose when exposed to 650° C., liberating mostly nicotine (97% peak areas).

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A bis-orotic acid salt-co-crystal of nicotine and orotic acid, characterized by an X-ray powder diffraction pattern having peaks at one or more of the following 2-theta diffraction angles: 8.8, 13.4, 17.7, 26.5, and 29.3.

2. The salt-co-crystal of claim 1, wherein at least about 50% of the salt-co-crystal is in crystalline form.

3. A pharmaceutical product comprising the salt-co-crystal of nicotine and orotic acid of claim 1 and one or more pharmaceutically acceptable excipients.

4. The pharmaceutical product of claim 3, in a form selected from the group consisting of a pill, tablet, lozenge, capsule, caplet, pouch, gum, inhaler, solution, and cream.

5. A method of preparing the salt-co-crystal of claim 1, comprising combining nicotine and orotic acid to form a solid and isolating the solid.

6. The method of claim 5, wherein the combining comprises mixing the nicotine and orotic acid in THF, ethanol, or a mixture thereof.

7. The pharmaceutical product of claim 3, wherein the one or more pharmaceutically acceptable excipients comprise isomalt.

* * * * *